US012692505B2

(12) United States Patent (10) Patent No.: US 12,692,505 B2
Nagase et al. (45) Date of Patent: Jul. 28, 2026

(54) METHOD FOR SECRETORY PRODUCTION OF PROTEIN

(71) Applicant: AJINOMOTO CO., INC., Tokyo (JP)

(72) Inventors: Yumi Nagase, Kanagawa (JP); Yoshihiko Matsuda, Kanagawa (JP)

(73) Assignee: AJINOMOTO CO., INC., Tokyo (JP)

( * ) Notice: Subject to any disclaimer, the term of this patent is extended or adjusted under 35 U.S.C. 154(b) by 1357 days.

(21) Appl. No.: 17/072,429

(22) Filed: Oct. 16, 2020

(65) Prior Publication Data

US 2021/0024941 A1 Jan. 28, 2021

Related U.S. Application Data

(63) Continuation of application No. PCT/JP2019/017100, filed on Apr. 22, 2019.

(30) Foreign Application Priority Data

Apr. 20, 2018 (JP) ................................. 2018-081138

(51) Int. Cl.
| *C12N 15/77* | (2006.01) |
| *C07K 14/34* | (2006.01) |
| *C12N 1/20* | (2026.01) |
| *C12N 9/16* | (2006.01) |
| *C12N 15/10* | (2006.01) |

(52) U.S. Cl.
CPC .............. *C12N 15/77* (2013.01); *C07K 14/34* (2013.01); *C12N 1/20* (2013.01); *C12N 9/16* (2013.01); *C12N 15/102* (2013.01); *C07K 2319/02* (2013.01)

(58) Field of Classification Search
CPC . C12N 15/77; C12N 1/20; C12N 9/16; C12N 15/102; C07K 14/34; C07K 2319/02
See application file for complete search history.

(56) References Cited

U.S. PATENT DOCUMENTS

| 4,965,197 | A | 10/1990 | Liebl et al. | |
| 6,027,920 | A | 2/2000 | Joliff et al. | |
| 2003/0082746 | A1 | 5/2003 | Kikuchi et al. | |
| 2004/0126847 | A1 | 7/2004 | Kikuchi et al. | |
| 2007/0184525 | A1 | 8/2007 | Date et al. | |
| 2010/0041107 | A1* | 2/2010 | Herold ................... | C12N 15/77 435/348 |
| 2014/0220637 | A1 | 8/2014 | Tsurui et al. | |
| 2014/0234901 | A1 | 8/2014 | Matsuda et al. | |
| 2018/0037918 | A1 | 2/2018 | Matsuda et al. | |
| 2019/0241621 | A1 | 8/2019 | Ito et al. | |
| 2019/0241622 | A1 | 8/2019 | Ito et al. | |

FOREIGN PATENT DOCUMENTS

| CN | 1934265 | A | 3/2007 | |
| DE | 102004035543 | A1 | 2/2006 | |
| JP | 6-502548 | A | 3/1994 | |
| JP | 11-169182 | A | 6/1999 | |
| JP | 4320769 | B2 | 6/2009 | |
| JP | 4362651 | B2 | 8/2009 | |
| JP | 4730302 | B2 | 7/2011 | |
| WO | WO2005/090589 | A2 | 9/2005 | |
| WO | WO2013/062029 | A1 | 5/2013 | |
| WO | WO2013/065772 | A1 | 5/2013 | |
| WO | WO2013/065869 | A1 | 5/2013 | |
| WO | WO2013/118544 | A1 | 8/2013 | |
| WO | WO-2016171224 | A1 * | 10/2016 | ............. C07K 14/34 |
| WO | WO2018/074578 | A1 | 4/2018 | |
| WO | WO2018/074579 | A1 | 4/2018 | |

OTHER PUBLICATIONS

Bott et al (Appl Microbiol Biotechnol (2012) 94:1131-1150) (Year: 2012).*
Bott, M., et al., "Two-component signal transduction in Corynebacterium glutamicum and other corynebacteria: on the way towards stimuli and targets," Appl. Microbiol. Biotechnol. 2012;94:1131-1150.
Ehira, S., et al., "Regulation of Corynebacterium glutamicum Heat Shock Response by the Extracytoplasmic-Function Sigma Factor SigH and Transcriptional Regulators HspR and HrcA," J. Bacteriol. 2009;191(9):2964-2972.
Hentschel, E., et al., "Phosphatase activity of the histidine kinases ensures pathway specificity of the ChrSA and HrrSA two-component systems in Corynebacterium glutamicum," Mol. Microbiol. 2014;92(6):1326-1342.
Simonen, M., et al., "Protein Secretion in Bacillus Species," Microbiol. Rev. 1993;57(1):109-137.
Cregg, J. M., et al., "Recent Advances in the Expression of Foreign Genes in Pichia pastoris," Bio/Technology 1993;11:905-910.
Christensen, T., et al., "High Level Expression of Recombinant Genes in Aspergillus Oryzae," Bio/Technology 1988;6:1419-1422.
Dunn-Coleman, N. S., et al., "Commercial Levels of Chymosin Production by Aspergillus," Bio/Technology 1991;9:976-981.
Liebl, W., et al., "Expression, Secretion, and Processing of Staphylococcal Nuclease by Corynebacterium glutamicum," J. Bacteriol. 1992;174(6):1854-1861.

(Continued)

*Primary Examiner* — Thomas J. Visone
*Assistant Examiner* — Georgiana C Reglas
(74) *Attorney, Agent, or Firm* — Cermak & McGowan LLP; Shelly Guest Cermak

(57) ABSTRACT

A novel technique for improving secretory production of a heterologous protein by coryneform bacteria may include a method for secretory production of a heterologous protein. A coryneform bacterium having an ability of secretory production of a heterologous protein and has been modified so as to have a combination of two or more features from among the features (A), (B), and (C) is cultured to produce the heterologous protein by secretory production: (A) the activity of a RegX3 protein is reduced as compared with a non-modified strain; (B) the activity of an HrrSA system is reduced as compared with a non-modified strain; and (C) the activity of an HrcA protein is reduced as compared with a non-modified strain.

19 Claims, 3 Drawing Sheets

Specification includes a Sequence Listing.

(56)     References Cited

OTHER PUBLICATIONS

Billman-Jacobe, H., et al., "Expression and Secretion of Heterologous Proteases by Corynebacterium glutamicum," Appl. Environmen. Microbiol. 1995;61(4):1610-1613.

Salim, K., et al., Heterologous Expression of the Mycobacterium tuberculosis Gene Encoding Antigen 85A in Corynebacterium glutamicum, Appl. Environmen. Microbiol. 1997;63(11):4392-4400.

Chaddock, A. M., et al., "A new type of signal peptide: central role of a twin-arginine motif in transfer signals for the delta pH-dependent thylakoidal protein translocase," The EMBO Journal 1995;14(12):2715-2722.

Hynds, P. J., et al., "The Sec-independent Twin-arginine Translocation System Can Transport Both Tightly Folded and Malfolded Proteins across the Thylakoid Membrane," J. Biol. Chem. 1998;273(52):34868-34874.

Kocan, M., et al., "Two-Component Systems of Corynebacterium glutamicum: Deletion Analysis and Involvement of the PhoS-PhoR System in the Phosphate Starvation Response," J. Bacteriol. 2006;188(2):724-732.

Woo, H. M., Regulatory and metabolic aspects of the phosphate starvation response of Corynebacterium glutamicum, URN (NBN): um:nbn:de:hbz:061-20100825-090114-5, Duesseldorf, 2010.

Frunzke, J., et al., "Control of Heme Homeostasis in Corynebacterium glutamicum by the Two-Component System HrrSA," J. Bacteriol. 2011;193(5):1212-1221.

Kolaj, O., et al., "Use of folding modulators to improve heterologous protein production in *Escherichia coli*," Microbial Cell Factories 2009;8(9):pp. 1-17.

International Search Report for PCT Patent App. No. PCT/JP2019/017100 (Jul. 9, 2019).

Office Action for Chinese Patent Application No. 201980026987.5 (Mar. 18, 2023) with English language translation thereof.

White, Dylan W. et al., "Mycobacterium tuberculosis Pst/SenX3-RegX3 Regulates Membrane Vesicle Production Independently of ESX-5 Activity," American Society for Microbiology, mBio, 2018; vol. 9, Issue 3, e00778-18.

Jing, Chen et al., "Study on that function of corynebacterium glutamicum PhoPR two-component system in response to hypoxia stress," Journal of Northeast Agricultural University, 2020; vol. 51, No. 5, pp. 24-31, with machine translation.

* cited by examiner

1,    Marker (XL-Ladder Broad, APRO science)

2,    YDK010::phoS(W302C)/pPK4

3,    YDK010::phoS(W302C)/pPK4_CspAss_N15

4,    YDK010::phoS(W302C)ΔregX3ΔhrcA/pPK4_CspAss_N15

5,    YDK010::phoS(W302C)ΔregX3ΔhrrA/pPK4_CspAss_N15

6,    YDK010::phoS(W302C)ΔhrrAΔhrcA/pPK4_CspAss_N15

7,    YDK010::phoS(W302C)ΔregX3ΔhrrAΔhrcA/pPK4_CspAss_N15

8,    Marker (XL-Ladder Broad, APRO science)

| 1, | Marker (XL-Ladder Broad, APRO science) |
| 2, | YDK010::phoS(W302C)/pPK4 |
| 3, | YDK010::phoS(W302C)/pPK4_CspB6Xa-LFABP |
| 4, | YDK010::phoS(W302C)ΔregX3ΔhrcA/pPK4_CspB6Xa-LFABP |
| 5, | YDK010::phoS(W302C)ΔregX3ΔhrrA/pPK4_CspB6Xa-LFABP |
| 6, | YDK010::phoS(W302C)ΔhrrAΔhrcA/pPK4_CspB6Xa-LFABP |
| 7, | YDK010::phoS(W302C)ΔregX3ΔhrrAΔhrcA/pPK4_CspB6Xa-LFABP |
| 8, | Marker (XL-Ladder Broad, APRO science) |

1,   Marker (XL-Ladder Broad, APRO science)

2,   YDK010::phoS(W302C)/pPK6

3,   YDK010::phoS(W302C)/pPK6_T_bFGF

4,   YDK010::phoS(W302C)ΔregX3ΔhrcA/pPK6_T_bFGF

5,   YDK010::phoS(W302C)ΔregX3ΔhrrA/pPK6_T_bFGF

6,   YDK010::phoS(W302C)ΔhrrAΔhrcA/pPK6_T_bFGF

7,   YDK010::phoS(W302C)ΔregX3ΔhrrAΔhrcA/pPK6_T_bFGF

8,   Marker (XL-Ladder Broad, APRO science)

SEQUENCE LISTING

```
<160> NUMBER OF SEQ ID NOS: 64

<210> SEQ ID NO 1
<211> LENGTH: 1458
<212> TYPE: DNA
<213> ORGANISM: Corynebacterium glutamicum

<400> SEQUENCE: 1
atggaaaacc cttatgtcgc tgcgctcgat gacgataaaa aagaagtcgg cgcaataaaa        60
gaagcagaaa aagaacctga aataggtccc atcagagctg ccggacgagc cataccgctg       120
cgcacccgca tcattttgat cgtggtgggt atcgccgggc ttggtttgct ggtcaacgcg       180
attgctgttt ccagcctcat gcgtgaagtt tcctataccc gcatggatca agagctagag       240
acctcgatgg ggacgtgggc gcataacgtt gagctgttta atttcgatgg cgtccgccaa       300
gggccaccca gcgattatta tgtggccaag gtttttcctg atggatccag cattattttc       360
```

-continued

```
aacgatgcac aatcggcacc caatctagct gaaaccacca tcggtactgg tccacacact      420
gtggatgctg ctagcggttc tgcctccaac actccgtggc gtgtgatggc ggaaaagaac      480
ggtgacatta tcaccgtggt gggtaaaagc atggggcgtg aaacaaacct gctgtaccga      540
ttggtgatgg tgcagatgat catcggcgcg ctgattctgg ttgctatttt gattacttca      600
ctcttcctag tcagacgctc gttgcggccg ttgagagaag ttgaagagac cgccaccagg      660
attgcgggcg gtgatttgga tcgacgtgtc ccgcagtggc caatgaccac agaagtcgga      720
cagctgtcga atgccctcaa tatcatgttg gagcagctcc aagcctcaat tctgaccgcc      780
cagcaaaaag aagctcagat gcgccgattc gttggcgacg cctcccacga gctccgcaca      840
ccactgacct ctgtgaaggg cttcaccgag ctgtattcat caggtgcaac agatgatgcc      900
aactgggtca tgtccaagat cggtggcgaa gcccaacgca tgagtgtgct tgtggaagac      960
ctcctgtcac tgacgcgtgc cgaaggccag caaatggaga agcaccgcgt tgacgtgctg     1020
gaactcgcat tggcagtacg cggatccatg cgagcagcct ggccagatcg caccgtcaac     1080
gtgtccaata agccgagtc cattccagtt gttgaaggcg acccaacccg cctccaccaa     1140
gttctcacca acctggttgc caacggactc aaccacggcg accggacgc ggaagtcagc     1200 attgagatca acaccgatgg gcaaaacgtg aggattctcg tggcagacaa cggtgtcgga     1260
atgtctgaag aagatgccca gcatatcttc gagcgtttct accgcgccga ttcctcccgc     1320
tcacgcgcat ccggcggatc gggcctcggc cttgcgatca cgaaatccct ggtcgaaggc     1380
cacggcggca cagtcaccgt cgacagcgtg caaggcgaag cacggtgtt cacgatcacc     1440 ttgccggcgg tttcttaa                                                  1458
```

```
<210> SEQ ID NO 2
<211> LENGTH: 485
<212> TYPE: PRT
<213> ORGANISM: Corynebacterium glutamicum

<400> SEQUENCE: 2

Met Glu Asn Pro Tyr Val Ala Ala Leu Asp Asp Asp Lys Lys Glu Val
1               5                   10                  15

Gly Ala Ile Lys Glu Ala Glu Lys Glu Pro Glu Ile Gly Pro Ile Arg
                20                  25                  30

Ala Ala Gly Arg Ala Ile Pro Leu Arg Thr Arg Ile Ile Leu Ile Val
            35                  40                  45

Val Gly Ile Ala Gly Leu Gly Leu Leu Val Asn Ala Ile Ala Val Ser
        50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
                100                 105                 110

Pro Asp Gly Ser Ser Ile Ile Phe Asn Asp Ala Gln Ser Ala Pro Asn
            115                 120                 125

Leu Ala Glu Thr Thr Ile Gly Thr Gly Pro His Thr Val Asp Ala Ala
        130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175
```

```
Leu Leu Tyr Arg Leu Val Met Val Gln Met Ile Ile Gly Ala Leu Ile
            180                 185                 190

Leu Val Ala Ile Leu Ile Thr Ser Leu Phe Leu Val Arg Arg Ser Leu
            195                 200                 205

Arg Pro Leu Arg Glu Val Glu Glu Thr Ala Thr Arg Ile Ala Gly Gly
            210                 215                 220

Asp Leu Asp Arg Arg Val Pro Gln Trp Pro Met Thr Thr Glu Val Gly
        225                 230                 235                 240

Gln Leu Ser Asn Ala Leu Asn Ile Met Leu Glu Gln Leu Gln Ala Ser
            245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
            275                 280                 285

Thr Glu Leu Tyr Ser Ser Gly Ala Thr Asp Asp Ala Asn Trp Val Met
            290                 295                 300

Ser Lys Ile Gly Gly Glu Ala Gln Arg Met Ser Val Leu Val Glu Asp
        305                 310                 315                 320

Leu Leu Ser Leu Thr Arg Ala Glu Gly Gln Gln Met Glu Lys His Arg
            325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
            355                 360                 365

Pro Val Val Glu Gly Asp Pro Thr Arg Leu His Gln Val Leu Thr Asn
            370                 375                 380

Leu Val Ala Asn Gly Leu Asn His Gly Gly Pro Asp Ala Glu Val Ser
        385                 390                 395                 400

Ile Glu Ile Asn Thr Asp Gly Gln Asn Val Arg Ile Leu Val Ala Asp
            405                 410                 415

Asn Gly Val Gly Met Ser Glu Glu Asp Ala Gln His Ile Phe Glu Arg
            420                 425                 430

Phe Tyr Arg Ala Asp Ser Ser Arg Ser Arg Ala Ser Gly Gly Ser Gly
            435                 440                 445

Leu Gly Leu Ala Ile Thr Lys Ser Leu Val Glu Gly His Gly Gly Thr
        450                 455                 460

Val Thr Val Asp Ser Val Gln Gly Glu Gly Thr Val Phe Thr Ile Thr
465                 470                 475                 480

Leu Pro Ala Val Ser
                485
```

```
<210> SEQ ID NO 3
<211> LENGTH: 485
<212> TYPE: PRT
<213> ORGANISM: Corynebacterium glutamicum

<400> SEQUENCE: 3
```

```
Met Glu Asn Pro Tyr Val Ala Ala Leu Asp Asp Glu Asn Gln Glu Val
1               5                   10                  15

Gly Val Lys Lys Glu Ala Glu Lys Glu Pro Glu Ile Gly Pro Ile Arg
            20                  25                  30

Ala Ala Gly Arg Ala Ile Pro Leu Arg Thr Arg Ile Ile Leu Ile Val
        35                  40                  45

Val Gly Ile Ala Gly Leu Gly Leu Leu Val Asn Ala Ile Ala Val Ser
```

-continued

```
            50                55                60

Ser Leu Met Arg Glu Val Ser Tyr Thr Arg Met Asp Gln Glu Leu Glu
65                  70                75                80

Thr Ser Met Gly Thr Trp Ala His Asn Val Glu Leu Phe Asn Phe Asp
                85                90                95

Gly Val Arg Gln Gly Pro Pro Ser Asp Tyr Tyr Val Ala Lys Val Phe
            100               105               110

Pro Asp Gly Ser Ser Ile Ile Phe Asn Asp Ala Gln Ser Ala Pro Asp
            115               120               125

Leu Ala Glu Thr Thr Ile Gly Thr Gly Pro His Thr Val Asp Ala Ala
            130               135               140

Ser Gly Ser Ala Ser Asn Thr Pro Trp Arg Val Met Ala Glu Lys Asn
145               150               155               160

Gly Asp Ile Ile Thr Val Val Gly Lys Ser Met Gly Arg Glu Thr Asn
                165               170               175

Leu Leu Tyr Arg Leu Val Met Val Gln Met Ile Ile Gly Ala Leu Ile
            180               185               190

Leu Val Ala Ile Leu Ile Thr Ser Leu Phe Leu Val Arg Arg Ser Leu
            195               200               205

Arg Pro Leu Arg Glu Val Glu Glu Thr Ala Thr Arg Ile Ala Gly Gly
            210               215               220

Asp Leu Asp Arg Arg Val Pro Gln Trp Pro Met Thr Thr Glu Val Gly
225               230               235               240

Gln Leu Ser Asn Ala Leu Asn Ile Met Leu Glu Gln Leu Gln Ala Ser
                245               250               255

Ile Leu Thr Ala Gln Gln Lys Glu Ala Gln Met Arg Arg Phe Val Gly
            260               265               270

Asp Ala Ser His Glu Leu Arg Thr Pro Leu Thr Ser Val Lys Gly Phe
            275               280               285

Thr Glu Leu Tyr Ser Ser Gly Ala Thr Asp Asp Ala Asn Trp Val Met
    290               295               300

Ser Lys Ile Gly Gly Glu Ala Gln Arg Met Ser Val Leu Val Glu Asp
305               310               315               320

Leu Leu Ser Leu Thr Arg Ala Glu Gly Gln Gln Met Glu Lys His Arg
                325               330               335

Val Asp Val Leu Glu Leu Ala Leu Ala Val Arg Gly Ser Met Arg Ala
            340               345               350

Ala Trp Pro Asp Arg Thr Val Asn Val Ser Asn Lys Ala Glu Ser Ile
            355               360               365

Pro Val Val Lys Gly Asp Pro Thr Arg Leu His Gln Val Leu Thr Asn
    370               375               380

Leu Val Ala Asn Gly Leu Asn His Gly Gly Pro Asp Ala Glu Val Ser
385               390               395               400

Ile Glu Ile Asn Thr Asp Gly Gln Asn Val Arg Ile Leu Val Ala Asp
                405               410               415

Asn Gly Val Gly Met Ser Glu Glu Asp Ala Gln His Ile Phe Glu Arg
            420               425               430

Phe Tyr Arg Ala Asp Ser Ser Arg Ser Arg Ala Ser Gly Gly Ser Gly
            435               440               445

Leu Gly Leu Ala Ile Thr Lys Ser Leu Val Glu Gly His Gly Gly Thr
    450               455               460

Val Thr Val Asp Ser Val Gln Gly Glu Gly Thr Val Phe Thr Ile Thr
465               470               475               480
```

```
Leu Pro Ala Val Ser
                485

<210> SEQ ID NO 4
<211> LENGTH: 485
<212> TYPE: PRT
<213> ORGANISM: Corynebacterium glutamicum

<400> SEQUENCE: 4

Met Glu Asn Pro Tyr Val Ala Ala Leu Asp Asp Glu Asn Gln Glu Val
1               5                   10                  15

Gly Val Lys Lys Glu Ala Glu Lys Glu Pro Glu Ile Gly Pro Ile Arg
                20                  25                  30

Ala Ala Gly Arg Ala Ile Pro Leu Arg Thr Arg Ile Ile Leu Ile Val
            35                  40                  45

Val Gly Ile Ala Gly Leu Gly Leu Leu Val Asn Ala Ile Ala Val Ser
        50                  55                  60

Ser Leu Met Arg Glu Val Ser Tyr Thr Arg Met Asp Gln Glu Leu Glu
65                  70                  75                  80

Thr Ser Met Gly Thr Trp Ala His Asn Val Glu Leu Phe Asn Phe Asp
                85                  90                  95

Gly Val Arg Gln Gly Pro Pro Ser Asp Tyr Tyr Val Ala Lys Val Phe
                100                 105                 110

Pro Asp Gly Ser Ser Ile Ile Phe Asn Asp Ala Gln Ser Ala Pro Asp
            115                 120                 125

Leu Ala Glu Thr Thr Ile Gly Thr Gly Pro His Thr Val Asp Ala Ala
        130                 135                 140

Ser Gly Ser Ala Ser Asn Thr Pro Trp Arg Val Met Ala Glu Lys Asn
145                 150                 155                 160

Gly Asp Ile Ile Thr Val Val Gly Lys Ser Met Gly Arg Glu Thr Asn
                165                 170                 175

Leu Leu Tyr Arg Leu Val Val Val Gln Met Ile Ile Gly Ala Leu Ile
            180                 185                 190

Leu Val Ala Ile Leu Ile Thr Ser Leu Phe Leu Val Arg Arg Ser Leu
        195                 200                 205

Arg Pro Leu Arg Glu Val Glu Glu Thr Ala Thr Arg Ile Ala Gly Gly
    210                 215                 220

Asp Leu Asp Arg Arg Val Pro Gln Trp Pro Met Thr Thr Glu Val Gly
225                 230                 235                 240

Gln Leu Ser Asn Ala Leu Asn Ile Met Leu Glu Gln Leu Gln Ala Ser
                245                 250                 255

Ile Leu Thr Ala Gln Gln Lys Glu Ala Gln Met Arg Arg Phe Val Gly
            260                 265                 270

Asp Ala Ser His Glu Leu Arg Thr Pro Leu Thr Ser Val Lys Gly Phe
        275                 280                 285

Thr Glu Leu Tyr Ser Ser Gly Ala Thr Asp Asp Ala Asn Trp Val Met
    290                 295                 300

Ser Lys Ile Gly Gly Glu Ala Gln Arg Met Ser Val Leu Val Glu Asp
305                 310                 315                 320

Leu Leu Ser Leu Thr Arg Ala Glu Gly Gln Gln Met Glu Lys His Arg
                325                 330                 335

Val Asp Val Leu Glu Leu Ala Leu Ala Val Arg Gly Ser Met Arg Ala
            340                 345                 350

Ala Trp Pro Asp Arg Thr Val Asn Val Ser Asn Lys Ala Glu Ser Ile
```

```
            355                 360                 365

Pro Val Val Glu Gly Asp Pro Thr Arg Leu His Gln Val Leu Thr Asn
    370                 375                 380

Leu Val Ala Asn Gly Leu Asn His Gly Gly Pro Asp Ala Glu Val Ser
385                 390                 395                 400

Ile Glu Ile Asn Thr Asp Gly Gln Asn Val Arg Ile Leu Val Ala Asp
                405                 410                 415

Asn Gly Val Gly Met Ser Glu Glu Asp Ala Gln His Ile Phe Glu Arg
                420                 425                 430

Phe Tyr Arg Ala Asp Ser Ser Arg Ser Arg Ala Ser Gly Gly Ser Gly
                435                 440                 445

Leu Gly Leu Ala Ile Thr Lys Ser Leu Val Glu Gly His Gly Gly Thr
    450                 455                 460

Val Thr Val Asp Ser Val Gln Gly Glu Gly Thr Val Phe Thr Ile Thr
465                 470                 475                 480

Leu Pro Ala Val Ser
                485

<210> SEQ ID NO 5
<211> LENGTH: 504
<212> TYPE: PRT
<213> ORGANISM: Corynebacterium callunae

<400> SEQUENCE: 5

Met Glu Asn Pro Tyr Val Ala Ala Leu Asp Lys Asn Ser Asn Phe Gly
1                   5                   10                  15

Ala Lys Asp Thr Asp Ser Ala Val Ser Asp Ser Thr Glu Val Ser Gln
                20                  25                  30

Asn Asn Asp Gly Ile Gly Thr Pro Ala Thr Ala Glu Pro Lys Val Gly
                35                  40                  45

Pro Ile Arg Thr Ala Gly Arg Ala Met Pro Leu Arg Thr Arg Ile Ile
    50                  55                  60

Leu Leu Val Val Gly Ile Ala Gly Leu Gly Leu Leu Val Asn Ala Val
65                  70                  75                  80

Ala Val Ser Ser Leu Met Arg Glu Val Ser Tyr Thr Arg Met Asp Gln
                85                  90                  95

Asp Leu Glu Ser Ala Met Gly Thr Trp Val Arg Asn Val Glu Leu Phe
                100                 105                 110

Asn Phe Asp Gly Val Arg Gln Gly Pro Pro Ser Asp Tyr Tyr Val Ala
                115                 120                 125

Lys Val Phe Pro Asp Gly Ser Ser Ile Ile Phe Asn Asp Ala Glu Ser
    130                 135                 140

Ala Pro Asp Leu Gly Gln Thr Thr Ile Gly Thr Gly Pro His Thr Val
145                 150                 155                 160

Glu Ala Ala Glu Gly Ser Ala Ser Ser Thr His Trp Arg Val Met Ala
                165                 170                 175

Ala Lys Asn Gly Asp Val Ile Thr Val Val Gly Lys Ser Met Gly Arg
                180                 185                 190

Glu Ser Thr Leu Leu Tyr Arg Leu Val Val Val Gln Met Val Ile Gly
                195                 200                 205

Val Leu Ile Leu Ile Ala Ile Leu Ile Gly Ser Phe Phe Leu Val Arg
    210                 215                 220

Arg Ser Leu Lys Pro Leu Arg Glu Val Glu Glu Thr Ala Ser Arg Ile
225                 230                 235                 240
```

-continued

Ala Gly Gly Glu Leu Asp Arg Arg Val Pro Gln Trp Pro Met Thr Thr
            245                 250                 255

Glu Val Gly Gln Leu Ala Asn Ala Leu Asn Ile Met Leu Glu Gln Leu
            260                 265                 270

Gln Thr Ser Ile Met Asn Ala Gln Gln Lys Glu Ala Gln Met Arg Arg
            275                 280                 285

Phe Val Gly Asp Ala Ser His Glu Leu Arg Thr Pro Leu Thr Ser Val
            290                 295                 300

Lys Gly Phe Thr Glu Leu Tyr Ser Ser Gly Ala Thr Gln Asp Ala Asp
305                 310                 315                 320

Trp Val Leu Ser Lys Ile Gly Gly Glu Ala Gln Arg Met Ser Val Leu
                325                 330                 335

Val Glu Asp Leu Leu Ser Leu Thr Arg Ala Glu Gly Gln Gln Met Glu
            340                 345                 350

Lys His Arg Val Asp Met Leu Glu Leu Ala Leu Ala Val Arg Gly Ser
            355                 360                 365

Leu Lys Ala Ala Trp Pro Asp Arg Thr Val Asn Val Ala Asn Arg Ser
        370                 375                 380

Glu Asn Ile Pro Val Val Glu Gly Asp Pro Thr Arg Leu His Gln Val
385                 390                 395                 400

Leu Thr Asn Leu Val Ala Asn Gly Leu Asn His Gly Gly Pro Glu Ala
                405                 410                 415

Glu Val Asn Ile Gln Val Glu Thr Ala Asp Asp Lys Val Lys Ile Leu
            420                 425                 430

Val Ile Asp Asn Gly Val Gly Met Ser Lys Glu Asp Ala Glu His Ile
            435                 440                 445

Phe Glu Arg Phe Tyr Arg Ala Asp Thr Ser Arg Ser Arg Ala Ser Gly
        450                 455                 460

Gly Ser Gly Leu Gly Leu Ala Ile Thr Lys Ser Leu Val Glu Gly His
465                 470                 475                 480

Gly Gly Thr Ile Thr Val Asp Ser Glu Leu Gly Lys Gly Thr Val Phe
                485                 490                 495

Ser Ile Ile Leu Pro Ala Ala Glu
            500

<210> SEQ ID NO 6
<211> LENGTH: 458
<212> TYPE: PRT
<213> ORGANISM: Corynebacterium crenatum

<400> SEQUENCE: 6

Ile Gly Pro Ile Arg Ala Ala Gly Arg Ala Ile Pro Leu Arg Thr Arg
1               5                   10                  15

Ile Ile Leu Ile Val Val Gly Ile Ala Gly Leu Gly Leu Leu Val Asn
            20                  25                  30

Ala Ile Ala Val Ser Ser Leu Met Arg Glu Val Ser Tyr Thr Arg Met
        35                  40                  45

Asp Gln Glu Leu Glu Thr Ser Met Gly Thr Trp Ala His Asn Val Glu
        50                  55                  60

Leu Phe Asn Phe Asp Gly Val Arg Gln Gly Pro Pro Ser Asp Tyr Tyr
65                  70                  75                  80

Val Ala Lys Val Phe Pro Asp Gly Ser Ser Ile Ile Phe Asn Asp Ala
                85                  90                  95

Gln Ser Ala Pro Asp Leu Ala Glu Thr Thr Ile Gly Thr Gly Pro His
            100                 105                 110

-continued

```
Thr Val Asp Ala Ala Ser Gly Ser Ala Ser Asn Thr Pro Trp Arg Val
        115                 120                 125

Met Ala Glu Lys Asn Gly Asp Ile Ile Thr Val Val Gly Lys Ser Met
        130                 135                 140

Gly Arg Glu Thr Asn Leu Leu Tyr Arg Leu Val Met Val Gln Met Ile
145                 150                 155                 160

Ile Gly Ala Leu Ile Leu Val Ala Ile Leu Ile Thr Ser Leu Phe Leu
                165                 170                 175

Val Arg Arg Ser Leu Arg Pro Leu Arg Glu Val Glu Glu Thr Ala Thr
                180                 185                 190

Arg Ile Ala Gly Gly Asp Leu Asp Arg Arg Val Pro Gln Trp Pro Met
        195                 200                 205

Thr Thr Glu Val Gly Gln Leu Ser Asn Ala Leu Asn Ile Met Leu Glu
        210                 215                 220

Gln Leu Gln Ala Ser Ile Leu Ser Ala Gln Gln Lys Glu Ala Gln Met
225                 230                 235                 240

Arg Arg Phe Val Gly Asp Ala Ser His Glu Leu Arg Thr Pro Leu Thr
                245                 250                 255

Ser Val Lys Gly Phe Thr Glu Leu Tyr Ser Ser Gly Ala Thr Asp Asp
                260                 265                 270

Ala Asn Trp Val Met Ser Lys Ile Gly Gly Glu Ala Gln Arg Met Ser
        275                 280                 285

Val Leu Val Glu Asp Leu Leu Ser Leu Thr Arg Ala Glu Gly Gln Gln
        290                 295                 300

Met Glu Lys His Arg Val Asp Val Leu Glu Leu Ala Leu Ala Val Arg
305                 310                 315                 320

Gly Ser Met Arg Ala Ala Trp Pro Asp Arg Thr Val Asn Val Ser Asn
                325                 330                 335

Lys Ala Ala Ser Ile Pro Val Val Glu Gly Asp Pro Thr Arg Leu His
                340                 345                 350

Gln Val Leu Thr Asn Leu Val Ala Asn Gly Leu Asn His Gly Gly Pro
        355                 360                 365

Asp Ala Glu Val Ser Ile Glu Ile Asn Thr Asp Gly Gln Asn Val Arg
        370                 375                 380

Ile Leu Val Ala Asp Asn Gly Val Gly Met Ser Glu Glu Asp Ala Gln
385                 390                 395                 400

His Ile Phe Glu Arg Phe Tyr Arg Ala Asp Ser Ser Arg Ser Arg Ala
                405                 410                 415

Ser Gly Gly Ser Gly Leu Gly Leu Ala Ile Thr Lys Ser Leu Val Glu
                420                 425                 430

Gly His Gly Gly Thr Val Thr Val Asp Ser Val Gln Gly Glu Gly Thr
        435                 440                 445

Val Phe Thr Ile Thr Leu Pro Ala Val Ser
        450                 455
```

```
<210> SEQ ID NO 7
<211> LENGTH: 471
<212> TYPE: PRT
<213> ORGANISM: Corynebacterium efficiens

<400> SEQUENCE: 7

Met Thr Ala Pro Glu Asn Pro His Ala Gln Val Thr Pro Val Gly Arg
1               5                   10                  15

Phe Arg Gln Ala Ala Arg Gly Val Pro Leu Arg Thr Arg Ile Ile Leu
```

-continued

```
                20                  25                  30

Leu Val Val Gly Ile Ala Gly Leu Gly Leu Leu Val Asn Ala Ile Ala
            35                  40                  45

Val Ser Ser Leu Met Arg Glu Val Ser Tyr Ser Arg Met Asp Gln Glu
        50                  55                  60

Leu Glu Ser Ala Met Asn Ser Trp Ala Gln Thr Ala Glu Leu Phe Gly
65                  70                  75                  80

Ser Ile Thr Leu Gly Pro Pro Ser Asp Tyr Tyr Val Val Arg Ile Phe
                85                  90                  95

Pro Asp Gly Ser His Met Val Phe Asn Gln Ser Asp Ser Ala Pro Asp
            100                 105                 110

Leu Gly Glu Thr Thr Ile Gly Ile Gly Pro His Thr Ala Ser Ala Ala
            115                 120                 125

Pro Gly Ser Ser Ser Ser Val Pro Trp Arg Val Ile Ala Ile Ser Asp
        130                 135                 140

Asn Gly Thr Ile Thr Val Val Gly Lys Ser Leu Ala Pro Glu Ser Met
145                 150                 155                 160

Leu Leu Tyr Arg Leu Val Ile Val Gln Leu Val Ile Gly Met Leu Ile
            165                 170                 175

Val Val Ala Ile Leu Leu Ser Ser Leu Tyr Leu Val Asn Arg Ser Leu
            180                 185                 190

Arg Pro Leu Arg Glu Val Glu Lys Thr Ala Lys Ser Ile Ala Gly Gly
            195                 200                 205

Asp Leu Asp Arg Arg Val Pro Gln Trp Pro Met Thr Thr Glu Val Gly
        210                 215                 220

Gln Leu Ala Asn Ala Leu Asn Ile Met Leu Glu Gln Leu Gln Ala Ser
225                 230                 235                 240

Ile Leu Ser Ala Gln Glu Lys Glu Ser Gln Met Arg Arg Phe Val Gly
            245                 250                 255

Asp Ala Ser His Glu Leu Arg Thr Pro Leu Thr Ser Val Lys Gly Tyr
            260                 265                 270

Ser Glu Leu Tyr His Ser Gly Ala Thr Arg Asp Ala Asp Trp Val Leu
            275                 280                 285

Ser Lys Ile Ser Gly Glu Ala Gln Arg Met Ser Val Leu Val Glu Asp
        290                 295                 300

Leu Leu Ser Leu Thr Arg Ala Glu Gly Gln Gln Met Glu Lys Arg Pro
305                 310                 315                 320

Val Asp Val Leu Glu Leu Ser Leu Ser Val Ala Ser Ser Met Arg Ala
            325                 330                 335

Ala Trp Pro Glu Arg Ser Ile Thr Val Val Asn Lys Thr Gly Ser Leu
            340                 345                 350

Pro Val Val Glu Gly Asp Ala Thr Arg Leu His Gln Val Leu Thr Asn
            355                 360                 365

Leu Val Asn Asn Gly Leu Asn His Gly Gly Pro Asp Ala Ser Val Glu
        370                 375                 380

Ile Glu Ile Ser Ala Glu Gly Gly Ser Val Leu Val Arg Val Val Asp
385                 390                 395                 400

Asp Gly Val Gly Met Thr Ala Glu Asp Ala Gln His Ile Phe Glu Arg
            405                 410                 415

Phe Tyr Arg Thr Asp Thr Ser Arg Ser Arg Ala Ser Gly Gly Ser Gly
            420                 425                 430

Leu Gly Leu Ala Ile Thr Lys Ser Leu Val Glu Gly His Arg Gly Thr
            435                 440                 445
```

-continued

```
Ile Thr Val Asp Ser Glu Val Gly Glu Gly Thr Val Phe Thr Ile Thr
    450                 455                 460

Leu Pro Ser Arg Met Glu Asp
465                 470

<210> SEQ ID NO 8
<211> LENGTH: 708
<212> TYPE: DNA
<213> ORGANISM: Corynebacterium glutamicum

<400> SEQUENCE: 8
atggacaacc agtctgacgg acaaatccgc gtactcgtcg ttgatgacga gccaaacatc      60
gtcgagctgc tcaccgtaag ccttaaattc caaggcttcg cagtgatgac cgccaacgat     120
ggcaatgaag ccctgaagat tgctcgtgag ttccgtccag acgcatacat cctcgatgtc     180
atgatgccag gaatggacgg cttcgagctg ctgaccaagc tgcgcggcga aggccttgac     240
agcccagttc tgtacctcac cgcaaaggat gccgtggagc accgcatcca cggcctgacc     300
atcggcgctg acgactacgt gaccaagcct ttctccctgg aagaagtaat cacccgcctg     360
cgcgtgattc ttcgtcgcgg tggagcagtt gaagaagaca cctcaacttc cctgcagtac     420
gcagacctca ccctcaacga tgaaacccac gaggtcacca aggctggcga actgatcgat     480
ctttccccaa ctgaattcaa cctcctgcgc tacctcatgc tcaacgctga agtggtgctg     540
tccaaggcaa agatcctgga taacgtgtgg cactacgatt ttggtggcga cggcaacgtc     600
gtggaatcct acatctccta cctgcgccgc aaggtggaca cccaggatcc gcagctaatt     660
cagactgttc gtggcgttgg atatgttctg cgcaccccac gtagctaa               708

<210> SEQ ID NO 9
<211> LENGTH: 235
<212> TYPE: PRT
<213> ORGANISM: Corynebacterium glutamicum

<400> SEQUENCE: 9

Met Asp Asn Gln Ser Asp Gly Gln Ile Arg Val Leu Val Val Asp Asp
1                 5                  10                  15

Glu Pro Asn Ile Val Glu Leu Leu Thr Val Ser Leu Lys Phe Gln Gly
                20                  25                  30

Phe Ala Val Met Thr Ala Asn Asp Gly Asn Glu Ala Leu Lys Ile Ala
            35                  40                  45

Arg Glu Phe Arg Pro Asp Ala Tyr Ile Leu Asp Val Met Met Pro Gly
        50                  55                  60

Met Asp Gly Phe Glu Leu Leu Thr Lys Leu Arg Gly Glu Gly Leu Asp
65                  70                  75                  80

Ser Pro Val Leu Tyr Leu Thr Ala Lys Asp Ala Val Glu His Arg Ile
                85                  90                  95

His Gly Leu Thr Ile Gly Ala Asp Asp Tyr Val Thr Lys Pro Phe Ser
            100                 105                 110

Leu Glu Glu Val Ile Thr Arg Leu Arg Val Ile Leu Arg Arg Gly Gly
        115                 120                 125

Ala Val Glu Glu Asp Thr Ser Thr Ser Leu Gln Tyr Ala Asp Leu Thr
    130                 135                 140

Leu Asn Asp Glu Thr His Glu Val Thr Lys Ala Gly Glu Leu Ile Asp
145                 150                 155                 160

Leu Ser Pro Thr Glu Phe Asn Leu Leu Arg Tyr Leu Met Leu Asn Ala
                165                 170                 175
```

-continued

Glu Val Val Leu Ser Lys Ala Lys Ile Leu Asp Asn Val Trp His Tyr
            180                 185                 190

Asp Phe Gly Gly Asp Gly Asn Val Val Glu Ser Tyr Ile Ser Tyr Leu
        195                 200                 205

Arg Arg Lys Val Asp Thr Gln Asp Pro Gln Leu Ile Gln Thr Val Arg
    210                 215                 220

Gly Val Gly Tyr Val Leu Arg Thr Pro Arg Ser
225                 230                 235

<210> SEQ ID NO 10
<211> LENGTH: 1500
<212> TYPE: DNA
<213> ORGANISM: Corynebacterium glutamicum

<400> SEQUENCE: 10
atgtttaaca accgtatccg cactgcagct ctcgctggtg caatcgcaat ctccaccgca          60
gcttccggcg tagctatccc agcattcgct caggagacca acccaacctt caacatcaac         120
aacggcttca acgatgctga tggatccacc atccagccag ttgagccagt taaccacacc         180
gaggaaaccc tccgcgacct gactgactcc accggcgctt acctggaaga gttccagtac         240
ggcaacgttg aggaaatcgt tgaagcatac ctgcaggttc aggcttccgc agacggattc         300
gatccttctg agcaggctgc ttacgaggct ttcgaggctg ctcgcgttcg tgcatcccag         360
gagctcgcgg cttccgctga gaccatcact aagacccgcg agtccgttgc ttacgcactc         420
aaggctgacc gcgaagctac cgcagctttc gaggcttacc tcagcgctct tcgtcaggtt         480
tcagtcatca cgatctgat cgctgatgct aacgccaaga caagactga ctttgcagag          540 atcgagctct acgatgttct ttacaccgac gccgacatct ctggcgatgc tccacttctt         600
gctcctgcat acaaggagct gaaggacctt caggctgagg ttgacgcaga cttcgagtgg         660
ttgggcgagt cgcaattga taacaatgaa gacaactacg tcattcgtac tcacatccct          720
gctgtagagg cactcaaggc agcgatcgat tcactggtcg acaccgttga gccacttcgt         780
gcagacgcta tcgctaagaa catcgaggct cagaagtctg acgttctggt tccccagctc         840
ttcctcgagc gtgcaactgc acagcgcgac accctgcgtg ttgtagaggc aatcttctct         900
acctctgctc gttacgttga actctacgag aacgtcgaga cgttaacgt tgagaacaag          960 acccttcgcc agcactactc ttccctgatc cctaacctct catcgcagc ggttggcaac         1020 atcaacgagc tcaacaatgc agatcaggct gcacgtgagc tcttcctcga ttgggacacc        1080
gacctcacca ccaacgatga ggacgaagct tactaccagg ctaagctcga cttcgctatc        1140
gagacctacg caaagatcct gatcaacggt gaagtttggc aggagccact cgcttacgtc        1200
cagaacctgg atgcaggcgc acgtcaggaa gcagctgacc gcgaagcaga gcgcgcagct        1260
gacgcagcat accgcgctga gcagctccgc atcgctcagg aagcagctga cgctcagaag        1320
gctctcgctg aggctcttgc taatgcaggc aacaacgaca cggtggcga caactcctcc         1380 gacgacaagg gaaccggttc ttccgacatc ggaacctggg gacctttcgc agcaattgca        1440
gctatcatcg cagcaatcgc agctatcttc ccattcctct ccggtatcgt taagttctaa        1500

<210> SEQ ID NO 11
<211> LENGTH: 499
<212> TYPE: PRT
<213> ORGANISM: Corynebacterium glutamicum

<400> SEQUENCE: 11

-continued

```
Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala Gln Glu
            20                  25                  30

Thr Asn Pro Thr Phe Asn Ile Asn Asn Gly Phe Asn Asp Ala Asp Gly
            35                  40                  45

Ser Thr Ile Gln Pro Val Glu Pro Val Asn His Thr Glu Glu Thr Leu
    50                  55                  60

Arg Asp Leu Thr Asp Ser Thr Gly Ala Tyr Leu Glu Glu Phe Gln Tyr
65                  70                  75                  80

Gly Asn Val Glu Glu Ile Val Glu Ala Tyr Leu Gln Val Gln Ala Ser
                85                  90                  95

Ala Asp Gly Phe Asp Pro Ser Glu Gln Ala Ala Tyr Glu Ala Phe Glu
                100                 105                 110

Ala Ala Arg Val Arg Ala Ser Gln Glu Leu Ala Ala Ser Ala Glu Thr
            115                 120                 125

Ile Thr Lys Thr Arg Glu Ser Val Ala Tyr Ala Leu Lys Ala Asp Arg
            130                 135                 140

Glu Ala Thr Ala Ala Phe Glu Ala Tyr Leu Ser Ala Leu Arg Gln Val
145                 150                 155                 160

Ser Val Ile Asn Asp Leu Ile Ala Asp Ala Asn Ala Lys Asn Lys Thr
                165                 170                 175

Asp Phe Ala Glu Ile Glu Leu Tyr Asp Val Leu Tyr Thr Asp Ala Asp
                180                 185                 190

Ile Ser Gly Asp Ala Pro Leu Leu Ala Pro Ala Tyr Lys Glu Leu Lys
                195                 200                 205

Asp Leu Gln Ala Glu Val Asp Ala Asp Phe Glu Trp Leu Gly Glu Phe
    210                 215                 220

Ala Ile Asp Asn Asn Glu Asp Asn Tyr Val Ile Arg Thr His Ile Pro
225                 230                 235                 240

Ala Val Glu Ala Leu Lys Ala Ala Ile Asp Ser Leu Val Asp Thr Val
                245                 250                 255

Glu Pro Leu Arg Ala Asp Ala Ile Ala Lys Asn Ile Glu Ala Gln Lys
                260                 265                 270

Ser Asp Val Leu Val Pro Gln Leu Phe Leu Glu Arg Ala Thr Ala Gln
            275                 280                 285

Arg Asp Thr Leu Arg Val Val Glu Ala Ile Phe Ser Thr Ser Ala Arg
    290                 295                 300

Tyr Val Glu Leu Tyr Glu Asn Val Glu Asn Val Asn Val Glu Asn Lys
305                 310                 315                 320

Thr Leu Arg Gln His Tyr Ser Ser Leu Ile Pro Asn Leu Phe Ile Ala
            325                 330                 335

Ala Val Gly Asn Ile Asn Glu Leu Asn Asn Ala Asp Gln Ala Ala Arg
            340                 345                 350

Glu Leu Phe Leu Asp Trp Asp Thr Asp Leu Thr Thr Asn Asp Glu Asp
            355                 360                 365

Glu Ala Tyr Tyr Gln Ala Lys Leu Asp Phe Ala Ile Glu Thr Tyr Ala
    370                 375                 380

Lys Ile Leu Ile Asn Gly Glu Val Trp Gln Glu Pro Leu Ala Tyr Val
385                 390                 395                 400

Gln Asn Leu Asp Ala Gly Ala Arg Gln Glu Ala Ala Asp Arg Glu Ala
                405                 410                 415

Glu Arg Ala Ala Asp Ala Ala Tyr Arg Ala Glu Gln Leu Arg Ile Ala
```

-continued

```
                  420              425              430

Gln Glu Ala Ala Asp Ala Gln Lys Ala Leu Ala Glu Ala Leu Ala Asn
            435              440              445

Ala Gly Asn Asn Asp Asn Gly Gly Asp Asn Ser Ser Asp Asp Lys Gly
        450              455              460

Thr Gly Ser Ser Asp Ile Gly Thr Trp Gly Pro Phe Ala Ala Ile Ala
465              470              475              480

Ala Ile Ile Ala Ala Ile Ala Ala Ile Phe Pro Phe Leu Ser Gly Ile
                485              490              495

Val Lys Phe

<210> SEQ ID NO 12
<211> LENGTH: 318
<212> TYPE: DNA
<213> ORGANISM: Corynebacterium glutamicum

<400> SEQUENCE: 12
atgtccctcg gaccatggga aattggaatc attgtcctgc tgatcatcgt gctgttcggc        60
gcgaagaagc tgcctgatgc agctcgttcc atcggccgtt ccatgcgcat cttcaagtct       120
gaagtcaaag aaatgaacaa ggacggcgat accccagaac aacagcagca gcctcagcag       180
cagattgcgc ccaaccagat cgaggctcct cagccaaact ttgagcagca ctaccaggga       240
cagcaggttc agcagcctca gaaccctcag acccctgact accgtcagaa ctacgaggat       300
ccaaaccgca cctcttaa                                                      318

<210> SEQ ID NO 13
<211> LENGTH: 105
<212> TYPE: PRT
<213> ORGANISM: Corynebacterium glutamicum

<400> SEQUENCE: 13

Met Ser Leu Gly Pro Trp Glu Ile Gly Ile Ile Val Leu Leu Ile Ile
1               5                10               15

Val Leu Phe Gly Ala Lys Lys Leu Pro Asp Ala Ala Arg Ser Ile Gly
            20               25               30

Arg Ser Met Arg Ile Phe Lys Ser Glu Val Lys Glu Met Asn Lys Asp
        35               40               45

Gly Asp Thr Pro Glu Gln Gln Gln Gln Pro Gln Gln Ile Ala Pro
    50               55               60

Asn Gln Ile Glu Ala Pro Gln Pro Asn Phe Glu Gln His Tyr Gln Gly
65               70               75               80

Gln Gln Val Gln Gln Pro Gln Asn Pro Gln Thr Pro Asp Tyr Arg Gln
                85               90               95

Asn Tyr Glu Asp Pro Asn Arg Thr Ser
            100              105

<210> SEQ ID NO 14
<211> LENGTH: 471
<212> TYPE: DNA
<213> ORGANISM: Corynebacterium glutamicum

<400> SEQUENCE: 14
atgttttcta gcgtgggttg gggagagatc ttcctcttag tcgttgtggg ccttgttgtc        60
atcggcccgg aacggttgcc tcgtttgatc caggacgcac gcgctgcgct gctcgctgca       120
cgtaccgcta tcgacaatgc aaagcagtcg ttggacagtg attttggttc ggaatttgat       180
```

```
gaaatccgaa agccactaac ccaggttgca cagtacagcc ggatgagccc caagacggcc        240
atcactaagg cgttatttga taatgattcc tcgttcctgg atgactttga tccaaagaag        300
atcatggccg aaggaacaga aggcgaagct cagcgcaaca agcaggcagc tgacaacaat        360
gcgaatgtgg tggaacgtcc agctgatggt tccaccgcac gcccaacgca aaacgatcca        420
aaagacggcc cgaattactc aggtggcgtc tcttggaccg atattattta g              471

<210> SEQ ID NO 15
<211> LENGTH: 156
<212> TYPE: PRT
<213> ORGANISM: Corynebacterium glutamicum

<400> SEQUENCE: 15

Met Phe Ser Ser Val Gly Trp Gly Glu Ile Phe Leu Leu Val Val Val
1               5                   10                  15

Gly Leu Val Val Ile Gly Pro Glu Arg Leu Pro Arg Leu Ile Gln Asp
            20                  25                  30

Ala Arg Ala Ala Leu Leu Ala Ala Arg Thr Ala Ile Asp Asn Ala Lys
        35                  40                  45

Gln Ser Leu Asp Ser Asp Phe Gly Ser Glu Phe Asp Glu Ile Arg Lys
    50                  55                  60

Pro Leu Thr Gln Val Ala Gln Tyr Ser Arg Met Ser Pro Lys Thr Ala
65                  70                  75                  80

Ile Thr Lys Ala Leu Phe Asp Asn Asp Ser Ser Phe Leu Asp Asp Phe
                85                  90                  95

Asp Pro Lys Lys Ile Met Ala Glu Gly Thr Glu Gly Glu Ala Gln Arg
            100                 105                 110

Asn Lys Gln Ala Ala Asp Asn Asn Ala Asn Val Val Glu Arg Pro Ala
        115                 120                 125

Asp Gly Ser Thr Ala Arg Pro Thr Gln Asn Asp Pro Lys Asp Gly Pro
    130                 135                 140

Asn Tyr Ser Gly Gly Val Ser Trp Thr Asp Ile Ile
145                 150                 155

<210> SEQ ID NO 16
<211> LENGTH: 945
<212> TYPE: DNA
<213> ORGANISM: Corynebacterium glutamicum

<400> SEQUENCE: 16
atgtccattg ttgagcacat caaagagttt cgacgccgac ttcttatcgc tctggcgggc         60
atcctcgtgg gcaccattat cggctttatt tggtacgatt tctcattttg gcagatcccc        120
actttgggcg agctgctgag ggatccgtac tgttctctgc ctgctgaatc ccgctgggcc        180
atgagcgact cagaggaatg tcgactgctc gcaaccggcc cgtttgatcc attcatgctt        240
cgccttaaag tagcggcgtt ggtgggtatg gttcttggct cacccgtgtg gctgagccag        300
ctgtggggct ttatcacccc aggtttgatg aagaatgagc gccgttacac cgcaatcttc        360
gtcacgattg ctgttgtgct gtttgtcggc ggtgctgttc ttgcgtactt cgtcgttgca        420
tatggtttgg agttcctcct taccattggt ggagacaccc aggcagcggc cctgactggt        480
gataagtact tcggattctt gctcgcgttg ttggcgattt tcggcgtgag cttcgaagtt        540
ccactggtga tcggcatgct caacattgtg ggtatcttgc cttacgatgc cattaaagat        600
aagcgacgca tgatcatcat gattttgttc gtgttcgctg ctttcatgac acccggccag        660
gatcctttca ccatgttggt gttggcgctt tcactcaccg ttctggtaga gcttgccctg        720
```

```
cagttctgtc gtttcaacga caaacgccgg gacaagaagc gcccagaatg gcttgatggc    780
gatgacctct ctgcatcacc actggatact tctgctggtg gagaagatgc tccaagccca    840
gtcgaaaccc cagaggcggt ggagccttcg cggatgctga acccaagtgg ggaggcgtcg    900
ataagctata aacccgggcg cgccgacttc ggtgacgtgc tctag                    945
```

```
<210> SEQ ID NO 17
<211> LENGTH: 314
<212> TYPE: PRT
<213> ORGANISM: Corynebacterium glutamicum

<400> SEQUENCE: 17

Met Ser Ile Val Glu His Ile Lys Glu Phe Arg Arg Arg Leu Leu Ile
1               5                   10                  15

Ala Leu Ala Gly Ile Leu Val Gly Thr Ile Ile Gly Phe Ile Trp Tyr
            20                  25                  30

Asp Phe Ser Phe Trp Gln Ile Pro Thr Leu Gly Glu Leu Leu Arg Asp
        35                  40                  45

Pro Tyr Cys Ser Leu Pro Ala Glu Ser Arg Trp Ala Met Ser Asp Ser
    50                  55                  60

Glu Glu Cys Arg Leu Leu Ala Thr Gly Pro Phe Asp Pro Phe Met Leu
65                  70                  75                  80

Arg Leu Lys Val Ala Ala Leu Val Gly Met Val Leu Gly Ser Pro Val
                85                  90                  95

Trp Leu Ser Gln Leu Trp Gly Phe Ile Thr Pro Gly Leu Met Lys Asn
            100                 105                 110

Glu Arg Arg Tyr Thr Ala Ile Phe Val Thr Ile Ala Val Val Leu Phe
            115                 120                 125

Val Gly Gly Ala Val Leu Ala Tyr Phe Val Val Ala Tyr Gly Leu Glu
        130                 135                 140

Phe Leu Leu Thr Ile Gly Gly Asp Thr Gln Ala Ala Ala Leu Thr Gly
145                 150                 155                 160

Asp Lys Tyr Phe Gly Phe Leu Leu Ala Leu Leu Ala Ile Phe Gly Val
                165                 170                 175

Ser Phe Glu Val Pro Leu Val Ile Gly Met Leu Asn Ile Val Gly Ile
            180                 185                 190

Leu Pro Tyr Asp Ala Ile Lys Asp Lys Arg Arg Met Ile Ile Met Ile
            195                 200                 205

Leu Phe Val Phe Ala Ala Phe Met Thr Pro Gly Gln Asp Pro Phe Thr
        210                 215                 220

Met Leu Val Leu Ala Leu Ser Leu Thr Val Leu Val Glu Leu Ala Leu
225                 230                 235                 240

Gln Phe Cys Arg Phe Asn Asp Lys Arg Arg Asp Lys Lys Arg Pro Glu
                245                 250                 255

Trp Leu Asp Gly Asp Asp Leu Ser Ala Ser Pro Leu Asp Thr Ser Ala
            260                 265                 270

Gly Gly Glu Asp Ala Pro Ser Pro Val Glu Thr Pro Glu Ala Val Glu
            275                 280                 285

Pro Ser Arg Met Leu Asn Pro Ser Gly Glu Ala Ser Ile Ser Tyr Lys
        290                 295                 300

Pro Gly Arg Ala Asp Phe Gly Asp Val Leu
305                 310
```

```
<210> SEQ ID NO 18
```

```
<211> LENGTH: 39
<212> TYPE: PRT
<213> ORGANISM: Escherichia coli

<400> SEQUENCE: 18

Met Asn Asn Asn Asp Leu Phe Gln Ala Ser Arg Arg Arg Phe Leu Ala
1               5                   10                  15

Gln Leu Gly Gly Leu Thr Val Ala Gly Met Leu Gly Pro Ser Leu Leu
            20                  25                  30

Thr Pro Arg Arg Ala Thr Ala
        35

<210> SEQ ID NO 19
<211> LENGTH: 27
<212> TYPE: PRT
<213> ORGANISM: Escherichia coli

<400> SEQUENCE: 19

Met Ser Leu Ser Arg Arg Gln Phe Ile Gln Ala Ser Gly Ile Ala Leu
1               5                   10                  15

Cys Ala Gly Ala Val Pro Leu Lys Ala Ser Ala
            20                  25

<210> SEQ ID NO 20
<211> LENGTH: 48
<212> TYPE: PRT
<213> ORGANISM: Bacillus subtilis

<400> SEQUENCE: 20

Met Ala Tyr Asp Ser Arg Phe Asp Glu Trp Val Gln Lys Leu Lys Glu
1               5                   10                  15

Glu Ser Phe Gln Asn Asn Thr Phe Asp Arg Arg Lys Phe Ile Gln Gly
            20                  25                  30

Ala Gly Lys Ile Ala Gly Leu Ser Leu Gly Leu Thr Ile Ala Gln Ser
        35                  40                  45

<210> SEQ ID NO 21
<211> LENGTH: 34
<212> TYPE: PRT
<213> ORGANISM: Bacillus subtilis

<400> SEQUENCE: 21

Met Lys Phe Val Lys Arg Arg Thr Thr Ala Leu Val Thr Thr Leu Met
1               5                   10                  15

Leu Ser Val Thr Ser Leu Phe Ala Leu Gln Pro Ser Ala Lys Ala Ala
            20                  25                  30

Glu His

<210> SEQ ID NO 22
<211> LENGTH: 30
<212> TYPE: PRT
<213> ORGANISM: Arthrobacter globiformis

<400> SEQUENCE: 22

Met Met Asn Leu Ser Arg Arg Thr Leu Leu Thr Thr Gly Ser Ala Ala
1               5                   10                  15

Thr Leu Ala Tyr Ala Leu Gly Met Ala Gly Ser Ala Gln Ala
            20                  25                  30

<210> SEQ ID NO 23
<211> LENGTH: 7
```

```
<212> TYPE: PRT
<213> ORGANISM: Artificial Sequence
<220> FEATURE:
<223> OTHER INFORMATION: Twin-Arginine Motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 23

Xaa Arg Arg Xaa Phe Leu Lys
1               5

<210> SEQ ID NO 24
<211> LENGTH: 5
<212> TYPE: PRT
<213> ORGANISM: Artificial Sequence
<220> FEATURE:
<223> OTHER INFORMATION: Twin-Arginine Motif
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (4)..(5)
<223> OTHER INFORMATION: Xaa can be any hydrophobic amino acid

<400> SEQUENCE: 24

Arg Arg Xaa Xaa Xaa
1               5

<210> SEQ ID NO 25
<211> LENGTH: 43
<212> TYPE: PRT
<213> ORGANISM: Corynebacterium glutamicum

<400> SEQUENCE: 25

Met Arg Asp Thr Ala Phe Arg Ser Ile Lys Ala Lys Ala Gln Ala Lys
1               5                   10                  15

Arg Arg Ser Leu Trp Ile Ala Ala Gly Ala Val Pro Thr Ala Ile Ala
            20                  25                  30

Leu Thr Met Ser Leu Ala Pro Met Ala Ser Ala
        35                  40

<210> SEQ ID NO 26
<211> LENGTH: 30
<212> TYPE: PRT
<213> ORGANISM: Corynebacterium glutamicum

<400> SEQUENCE: 26

Met Phe Asn Asn Arg Ile Arg Thr Ala Ala Leu Ala Gly Ala Ile Ala
1               5                   10                  15

Ile Ser Thr Ala Ala Ser Gly Val Ala Ile Pro Ala Phe Ala
            20                  25                  30

<210> SEQ ID NO 27
<211> LENGTH: 25
<212> TYPE: PRT
<213> ORGANISM: Corynebacterium stationis

<400> SEQUENCE: 27

Met Lys Arg Met Lys Ser Leu Ala Ala Ala Leu Thr Val Ala Gly Ala
```

-continued

```
1               5                       10                      15

Met Leu Ala Ala Pro Val Ala Thr Ala
            20                  25

<210> SEQ ID NO 28
<211> LENGTH: 469
<212> TYPE: PRT
<213> ORGANISM: Corynebacterium glutamicum

<400> SEQUENCE: 28

Gln Glu Thr Asn Pro Thr Phe Asn Ile Asn Asn Gly Phe Asn Asp Ala
1               5                       10                      15

Asp Gly Ser Thr Ile Gln Pro Val Glu Pro Val Asn His Thr Glu Glu
            20                  25                  30

Thr Leu Arg Asp Leu Thr Asp Ser Thr Gly Ala Tyr Leu Glu Glu Phe
        35                  40                  45

Gln Tyr Gly Asn Val Glu Glu Ile Val Glu Ala Tyr Leu Gln Val Gln
    50                  55                  60

Ala Ser Ala Asp Gly Phe Asp Pro Ser Glu Gln Ala Ala Tyr Glu Ala
65                  70                  75                  80

Phe Glu Ala Ala Arg Val Arg Ala Ser Gln Glu Leu Ala Ala Ser Ala
                85                  90                  95

Glu Thr Ile Thr Lys Thr Arg Glu Ser Val Ala Tyr Ala Leu Lys Ala
            100                 105                 110

Asp Arg Glu Ala Thr Ala Ala Phe Glu Ala Tyr Leu Ser Ala Leu Arg
        115                 120                 125

Gln Val Ser Val Ile Asn Asp Leu Ile Ala Asp Ala Asn Ala Lys Asn
    130                 135                 140

Lys Thr Asp Phe Ala Glu Ile Glu Leu Tyr Asp Val Leu Tyr Thr Asp
145                 150                 155                 160

Ala Asp Ile Ser Gly Asp Ala Pro Leu Leu Ala Pro Ala Tyr Lys Glu
                165                 170                 175

Leu Lys Asp Leu Gln Ala Glu Val Asp Ala Asp Phe Glu Trp Leu Gly
            180                 185                 190

Glu Phe Ala Ile Asp Asn Asn Glu Asp Asn Tyr Val Ile Arg Thr His
        195                 200                 205

Ile Pro Ala Val Glu Ala Leu Lys Ala Ala Ile Asp Ser Leu Val Asp
    210                 215                 220

Thr Val Glu Pro Leu Arg Ala Asp Ala Ile Ala Lys Asn Ile Glu Ala
225                 230                 235                 240

Gln Lys Ser Asp Val Leu Val Pro Gln Leu Phe Leu Glu Arg Ala Thr
                245                 250                 255

Ala Gln Arg Asp Thr Leu Arg Val Val Glu Ala Ile Phe Ser Thr Ser
            260                 265                 270

Ala Arg Tyr Val Glu Leu Tyr Glu Asn Val Glu Asn Val Asn Val Glu
        275                 280                 285

Asn Lys Thr Leu Arg Gln His Tyr Ser Ser Leu Ile Pro Asn Leu Phe
        290                 295                 300

Ile Ala Ala Val Gly Asn Ile Asn Glu Leu Asn Asn Ala Asp Gln Ala
305                 310                 315                 320

Ala Arg Glu Leu Phe Leu Asp Trp Asp Thr Asp Leu Thr Thr Asn Asp
                325                 330                 335

Glu Asp Glu Ala Tyr Tyr Gln Ala Lys Leu Asp Phe Ala Ile Glu Thr
            340                 345                 350
```

```
Tyr Ala Lys Ile Leu Ile Asn Gly Glu Val Trp Gln Glu Pro Leu Ala
        355                 360                 365

Tyr Val Gln Asn Leu Asp Ala Gly Ala Arg Gln Glu Ala Ala Asp Arg
        370                 375                 380

Glu Ala Glu Arg Ala Ala Asp Ala Ala Tyr Arg Ala Glu Gln Leu Arg
385                 390                 395                 400

Ile Ala Gln Glu Ala Ala Asp Ala Gln Lys Ala Leu Ala Glu Ala Leu
                405                 410                 415

Ala Asn Ala Gly Asn Asn Asp Asn Gly Gly Asp Asn Ser Ser Asp Asp
                420                 425                 430

Lys Gly Thr Gly Ser Ser Asp Ile Gly Thr Trp Gly Pro Phe Ala Ala
        435                 440                 445

Ile Ala Ala Ile Ile Ala Ala Ile Ala Ala Ile Phe Pro Phe Leu Ser
    450                 455                 460

Gly Ile Val Lys Phe
465

<210> SEQ ID NO 29
<211> LENGTH: 4
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala

<400> SEQUENCE: 29

Gln Glu Thr Xaa
1

<210> SEQ ID NO 30
<211> LENGTH: 5
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val

<400> SEQUENCE: 30

Gln Glu Thr Xaa Xaa
1               5

<210> SEQ ID NO 31
<211> LENGTH: 6
<212> TYPE: PRT
<213> ORGANISM: Corynebacterium glutamicum
<220> FEATURE:
<221> NAME/KEY: MISC_FEATURE
<222> LOCATION: (4)..(4)
<223> OTHER INFORMATION: Xaa is Asn, Gly, Thr, Pro, or Ala
<220> FEATURE:
<221> NAME/KEY: MISC_FEATURE
<222> LOCATION: (5)..(5)
<223> OTHER INFORMATION: Xaa is Pro, Thr, or Val
<220> FEATURE:
<221> NAME/KEY: MISC_FEATURE
<222> LOCATION: (6)..(6)
<223> OTHER INFORMATION: Xaa is Thr or Tyr

<400> SEQUENCE: 31

Gln Glu Thr Xaa Xaa Xaa
```

-continued

```
1               5

<210> SEQ ID NO 32
<211> LENGTH: 6
<212> TYPE: PRT
<213> ORGANISM: Corynebacterium glutamicum

<400> SEQUENCE: 32

Gln Glu Thr Asn Pro Thr
1               5

<210> SEQ ID NO 33
<211> LENGTH: 6
<212> TYPE: PRT
<213> ORGANISM: Corynebacterium glutamicum

<400> SEQUENCE: 33

Gln Glu Thr Gly Thr Tyr
1               5

<210> SEQ ID NO 34
<211> LENGTH: 6
<212> TYPE: PRT
<213> ORGANISM: Corynebacterium glutamicum

<400> SEQUENCE: 34

Gln Glu Thr Thr Val Thr
1               5

<210> SEQ ID NO 35
<211> LENGTH: 6
<212> TYPE: PRT
<213> ORGANISM: Corynebacterium glutamicum

<400> SEQUENCE: 35

Gln Glu Thr Pro Val Thr
1               5

<210> SEQ ID NO 36
<211> LENGTH: 6
<212> TYPE: PRT
<213> ORGANISM: Corynebacterium glutamicum

<400> SEQUENCE: 36

Gln Glu Thr Ala Val Thr
1               5

<210> SEQ ID NO 37
<211> LENGTH: 4
<212> TYPE: PRT
<213> ORGANISM: Artificial Sequence
<220> FEATURE:
<223> OTHER INFORMATION: Factor Xa

<400> SEQUENCE: 37

Ile Glu Gly Arg
1

<210> SEQ ID NO 38
<211> LENGTH: 6
<212> TYPE: PRT
<213> ORGANISM: Artificial Sequence
<220> FEATURE:
<223> OTHER INFORMATION: ProTEV

<400> SEQUENCE: 38
```

```
Glu Asn Leu Tyr Phe Gln
1               5

<210> SEQ ID NO 39
<211> LENGTH: 1161
<212> TYPE: DNA
<213> ORGANISM: Corynebacterium glutamicum

<400> SEQUENCE: 39
atgcgtcgcc acaagtccgc ggtcaccctg tccgaaaatc aggtcaccac ggtggggcag     60
gtcctccact tggcgattca aggctcccca acgggaatca cggttgtcga tcgcaccggc    120
gacgtcatct tatccaacgg ccgcgcccac gaattgggca tcgtccacga agatccgtc     180 gacggcaacg tttggcgcgt cgcccaggaa gccttccaag accaagaaac ccactcactc    240
gacgtccacc cagaccgcaa tccgcggcgc ccgggtagtc gcatcaccgc agtgcaggca    300
gtggtcaagc ctttaacgct tatcgacgat cgtttcgtga tcatctatgc ctccgacgaa    360
tccgaaaacg tgcgcatgga tcggcacgc cgagacttcg tcgcaaacgt ctcccacgaa     420
ctgaaaaccc ccgtcggcgg catggcactc ctcgcggaag ccctcatgga tcctccgac     480 gacccagaac aagtcgaata cttcggatcc aggctccacc gcgaagccca ccgcatggcc    540
gacatgatca cgaactgat ctcccttcc aaacttcagg gcgccgaacg actccctgat      600
atggaacccg tccaggctga cgacatcatc agcgaagcca tcgaacgcac ccaactcgcc    660
gccgacaacg ccaacatcga aatcattcgc ggcgaccgca ccggcgtttg ggtagaagcc    720
gatcgatccc tgctggtcac agccctggcg aacctgatca gcaatgcaat caactactca    780
ccaaaatcag tccccgtctc cgtttcacaa agcatccgaa acgacgtggt catgatccga    840
gtaaccgacc gcggcattgg catcgcaccc gaagaccaag gccgagtttt cgaaagattc    900
ttccgcgtcg acaaagcccg ctcccgccaa accggcggaa ctggccttgg cctcgcgata    960
gtcaaacatg tcatggccaa ccatggcggt agtattagtt tgtggtcacg tcctggaaca   1020
ggctccacat tcacacttga actccccgtt tatcacccag agtccaagga accggcagga   1080
tctaagcagg gacctagttt ggattccacct attcgtacga ctgcgtccaa agcatctggg   1140
cgccgaaagg aaaaatcatg a                                             1161

<210> SEQ ID NO 40
<211> LENGTH: 386
<212> TYPE: PRT
<213> ORGANISM: Corynebacterium glutamicum

<400> SEQUENCE: 40

Met Arg Arg His Lys Ser Ala Val Thr Leu Ser Glu Asn Gln Val Thr
1               5                  10                  15

Thr Val Gly Gln Val Leu His Leu Ala Ile Gln Gly Ser Pro Thr Gly
            20                  25                  30

Ile Thr Val Val Asp Arg Thr Gly Asp Val Ile Leu Ser Asn Gly Arg
        35                  40                  45

Ala His Glu Leu Gly Ile Val His Glu Arg Ser Val Asp Gly Asn Val
    50                  55                  60

Trp Arg Val Ala Gln Glu Ala Phe Gln Asp Gln Glu Thr His Ser Leu
65                  70                  75                  80

Asp Val His Pro Asp Arg Asn Pro Arg Arg Pro Gly Ser Arg Ile Thr
                85                  90                  95

Ala Val Gln Ala Val Val Lys Pro Leu Thr Leu Ile Asp Asp Arg Phe
```

```
            100              105              110
Val Ile Ile Tyr Ala Ser Asp Glu Ser Glu Asn Val Arg Met Glu Ser
            115              120              125

Ala Arg Arg Asp Phe Val Ala Asn Val Ser His Glu Leu Lys Thr Pro
    130              135              140

Val Gly Gly Met Ala Leu Leu Ala Glu Ala Leu Met Glu Ser Ser Asp
145              150              155              160

Asp Pro Glu Gln Val Glu Tyr Phe Gly Ser Arg Leu His Arg Glu Ala
                165              170              175

His Arg Met Ala Asp Met Ile Asn Glu Leu Ile Ser Leu Ser Lys Leu
            180              185              190

Gln Gly Ala Glu Arg Leu Pro Asp Met Glu Pro Val Gln Ala Asp Asp
            195              200              205

Ile Ile Ser Glu Ala Ile Glu Arg Thr Gln Leu Ala Ala Asp Asn Ala
    210              215              220

Asn Ile Glu Ile Ile Arg Gly Asp Arg Thr Gly Val Trp Val Glu Ala
225              230              235              240

Asp Arg Ser Leu Leu Val Thr Ala Leu Ala Asn Leu Ile Ser Asn Ala
            245              250              255

Ile Asn Tyr Ser Pro Lys Ser Val Pro Val Ser Val Ser Gln Ser Ile
            260              265              270

Arg Asn Asp Val Val Met Ile Arg Val Thr Asp Arg Gly Ile Gly Ile
            275              280              285

Ala Pro Glu Asp Gln Gly Arg Val Phe Glu Arg Phe Phe Arg Val Asp
    290              295              300

Lys Ala Arg Ser Arg Gln Thr Gly Gly Thr Gly Leu Gly Leu Ala Ile
305              310              315              320

Val Lys His Val Met Ala Asn His Gly Gly Ser Ile Ser Leu Trp Ser
            325              330              335

Arg Pro Gly Thr Gly Ser Thr Phe Thr Leu Glu Leu Pro Val Tyr His
            340              345              350

Pro Glu Ser Lys Glu Pro Ala Gly Ser Lys Gln Gly Pro Ser Leu Asp
            355              360              365

Ser Pro Ile Arg Thr Thr Ala Ser Lys Ala Ser Gly Arg Arg Lys Glu
    370              375              380

Lys Ser
385
```

```
<210> SEQ ID NO 41
<211> LENGTH: 699
<212> TYPE: DNA
<213> ORGANISM: Corynebacterium glutamicum

<400> SEQUENCE: 41
atgacgacaa tcctgatcgt tgaagatgag gaatcgttag cagatccttt ggcctttctt      60
cttcgcaaag aaggttttga caccatcatc gccggtgatg gcccaaccgc acttgtggag     120
ttcagtcgca acgaaatcga catcgtcctc ttagacctca tgctcccagg catgtctggc     180
accgacgtat gcaaagaact ccgcagcgta tccactgttc ccgtcatcat ggtcaccgcc     240
cgcgactccg agatcgacaa agttgttggc ctcgaactcg cgccgatga ttatgtaacc      300 aagccatatt cttcccgcga actcatcgcc cgcatccgcg ctgtcctgcg ccgacgcgga     360
gttactgaaa ccgaagccga agaattacca cttgacgatc aaatcctcga aggcggccgc     420
gtccgcatgg acgtcgattc ccacaccgtc accgtcggtg gcgaaccagt gagcatgcca     480
```

-continued

```
ctgaaggaat tcgaccttct ggagtacctc ctccgcaacg ccggccgagt cctcacccgc      540
ggacagctca tcgaccgaat ttggggcgca gattacgtcg gcgacaccaa aaccctcgac      600
gttcatgtca aaaggttgcg ttccaagatc gaagaagagc catctcgacc tcgttacctc      660
gtgaccgtgc gtggattggg ctacaaattc gagctgtag                             699
```

<210> SEQ ID NO 42
<211> LENGTH: 232
<212> TYPE: PRT
<213> ORGANISM: Corynebacterium glutamicum

<400> SEQUENCE: 42

```
Met Thr Thr Ile Leu Ile Val Glu Asp Glu Glu Ser Leu Ala Asp Pro
1               5                   10                  15

Leu Ala Phe Leu Leu Arg Lys Glu Gly Phe Asp Thr Ile Ile Ala Gly
            20                  25                  30

Asp Gly Pro Thr Ala Leu Val Glu Phe Ser Arg Asn Glu Ile Asp Ile
        35                  40                  45

Val Leu Leu Asp Leu Met Leu Pro Gly Met Ser Gly Thr Asp Val Cys
    50                  55                  60

Lys Glu Leu Arg Ser Val Ser Thr Val Pro Val Ile Met Val Thr Ala
65                  70                  75                  80

Arg Asp Ser Glu Ile Asp Lys Val Val Gly Leu Glu Leu Gly Ala Asp
                85                  90                  95

Asp Tyr Val Thr Lys Pro Tyr Ser Ser Arg Glu Leu Ile Ala Arg Ile
            100                 105                 110

Arg Ala Val Leu Arg Arg Arg Gly Val Thr Glu Thr Glu Ala Glu Glu
        115                 120                 125

Leu Pro Leu Asp Asp Gln Ile Leu Glu Gly Gly Arg Val Arg Met Asp
    130                 135                 140

Val Asp Ser His Thr Val Thr Val Gly Gly Glu Pro Val Ser Met Pro
145                 150                 155                 160

Leu Lys Glu Phe Asp Leu Leu Glu Tyr Leu Leu Arg Asn Ala Gly Arg
                165                 170                 175

Val Leu Thr Arg Gly Gln Leu Ile Asp Arg Ile Trp Gly Ala Asp Tyr
            180                 185                 190

Val Gly Asp Thr Lys Thr Leu Asp Val His Val Lys Arg Leu Arg Ser
        195                 200                 205

Lys Ile Glu Glu Glu Pro Ser Arg Pro Arg Tyr Leu Val Thr Val Arg
    210                 215                 220

Gly Leu Gly Tyr Lys Phe Glu Leu
225                 230
```

<210> SEQ ID NO 43
<211> LENGTH: 1335
<212> TYPE: DNA
<213> ORGANISM: Corynebacterium glutamicum

<400> SEQUENCE: 43

```
atgcagtcaa gcctagatcg tgtgtcggaa accggacgca atgagctcga tgttgaaacc       60
cttgtgaaga aggggaatca accgggcgcg atgagctatc gcaacagtat ccacattttg      120
acagcctcgc tgctggtcgt ggggttggga gcttccgccc gcctgacgct gccgatgttt      180
gcgctgtcgt gcgtgctgtt gtttgtgtgg ggttttctgt acttctatgg atcaaccaaa      240
cgcgtagatt tgagccacgg catgcagctg ggctggctgt ttgtgctgac gctggtgtgg      300
```

```
atttttatgg tgccgatcgt gcccgtgtcc atttatctgc tgttcccgct gttttttcctc      360 tatctacagg tgatgcctga cgtgagaggc attattgcga ttttgggtgc gacagcgatt      420
gcgattgcca gccagtattc cgtggggttg acctttggtg gtgtgatggg tccggtggtc      480
tctgcgatcg tgaccgtggc tattgattac gcgttccgca cgttgtggcg ggtgaataat      540
gaaaagcagg aattgattga tcagttgatt gaaactcgct cccagctggc ggtgacggaa      600
cgaaatgcgg gtatcgctgc ggaacgtcaa cgtattgcgc atgaaattca cgacacggtc      660
gcccagggac tctcctccat tcaaatgctg ctgcatgtct ctgaacagga gattctcgtt      720
gctgagatgg aagagaagcc aaaggaggcg atcgtgaaga agatgcgcct tgcccgacaa      780
acagcctccg acaatctcag tgaggctcgc gcgatgattg cggcgttgca accagcagcg      840
ctgtctaaaa cctccttgga agcagcactt caccgcgtca cagaaccgtt gttgggtatt      900
aattttgtga tttctgtcga cggtgatgtt cgccaactgc ccatgaaaac tgaagccacc      960
cttctgcgaa ttgctcaagg tgcgatcgga aatgtggcga acattcaga ggcgaaaaac      1020 tgccacgtga cactaaccta cgaagacaca gaagtacgcc ttgatgtggt tgatgacggt      1080
gtgggttttg agccttcgga agtgtccagt accccgctg gccttggcca tatcggctta      1140
accgcattgc agcagcgcgc gatggaattg cacggcgaag ttatagtgga atctgcatat      1200
gggcagggta ctgcggtatc tgcagcattg ccggtggagc caccagaggg gtttgtcggg      1260
gcgccggttt tggcagattc ggactcaagt gctacaggcg aggttgaact aagttctcca      1320
actgacgatg agtaa                                                        1335
```

<210> SEQ ID NO 44
<211> LENGTH: 444
<212> TYPE: PRT
<213> ORGANISM: Corynebacterium glutamicum

<400> SEQUENCE: 44

```
Met Gln Ser Ser Leu Asp Arg Val Ser Glu Thr Gly Arg Asn Glu Leu
1               5                   10                  15

Asp Val Glu Thr Leu Val Lys Lys Gly Asn Gln Pro Gly Ala Met Ser
            20                  25                  30

Tyr Arg Asn Ser Ile His Ile Leu Thr Ala Ser Leu Leu Val Val Gly
        35                  40                  45

Leu Gly Ala Ser Ala Arg Leu Thr Leu Pro Met Phe Ala Leu Ser Cys
    50                  55                  60

Val Leu Leu Phe Val Trp Gly Phe Leu Tyr Phe Tyr Gly Ser Thr Lys
65                  70                  75                  80

Arg Val Asp Leu Ser His Gly Met Gln Leu Gly Trp Leu Phe Val Leu
            85                  90                  95

Thr Leu Val Trp Ile Phe Met Val Pro Ile Val Pro Val Ser Ile Tyr
            100                 105                 110

Leu Leu Phe Pro Leu Phe Phe Leu Tyr Leu Gln Val Met Pro Asp Val
        115                 120                 125

Arg Gly Ile Ile Ala Ile Leu Gly Ala Thr Ala Ile Ala Ile Ala Ser
    130                 135                 140

Gln Tyr Ser Val Gly Leu Thr Phe Gly Gly Val Met Gly Pro Val Val
145                 150                 155                 160

Ser Ala Ile Val Thr Val Ala Ile Asp Tyr Ala Phe Arg Thr Leu Trp
                165                 170                 175

Arg Val Asn Asn Glu Lys Gln Glu Leu Ile Asp Gln Leu Ile Glu Thr
```

-continued

```
            180             185             190
Arg Ser Gln Leu Ala Val Thr Glu Arg Asn Ala Gly Ile Ala Ala Glu
        195             200             205
Arg Gln Arg Ile Ala His Glu Ile His Asp Thr Val Ala Gln Gly Leu
    210             215             220
Ser Ser Ile Gln Met Leu Leu His Val Ser Glu Gln Glu Ile Leu Val
225             230             235             240
Ala Glu Met Glu Glu Lys Pro Lys Glu Ala Ile Val Lys Lys Met Arg
            245             250             255
Leu Ala Arg Gln Thr Ala Ser Asp Asn Leu Ser Glu Ala Arg Ala Met
            260             265             270
Ile Ala Ala Leu Gln Pro Ala Ala Leu Ser Lys Thr Ser Leu Glu Ala
        275             280             285
Ala Leu His Arg Val Thr Glu Pro Leu Leu Gly Ile Asn Phe Val Ile
    290             295             300
Ser Val Asp Gly Asp Val Arg Gln Leu Pro Met Lys Thr Glu Ala Thr
305             310             315             320
Leu Leu Arg Ile Ala Gln Gly Ala Ile Gly Asn Val Ala Lys His Ser
            325             330             335
Glu Ala Lys Asn Cys His Val Thr Leu Thr Tyr Glu Asp Thr Glu Val
            340             345             350
Arg Leu Asp Val Val Asp Asp Gly Val Gly Phe Glu Pro Ser Glu Val
            355             360             365
Ser Ser Thr Pro Ala Gly Leu Gly His Ile Gly Leu Thr Ala Leu Gln
        370             375             380
Gln Arg Ala Met Glu Leu His Gly Glu Val Ile Val Glu Ser Ala Tyr
385             390             395             400
Gly Gln Gly Thr Ala Val Ser Ala Ala Leu Pro Val Glu Pro Pro Glu
            405             410             415
Gly Phe Val Gly Ala Pro Val Leu Ala Asp Ser Asp Ser Ser Ala Thr
            420             425             430
Gly Glu Val Glu Leu Ser Ser Pro Thr Asp Asp Glu
        435             440
```

```
<210> SEQ ID NO 45
<211> LENGTH: 639
<212> TYPE: DNA
<213> ORGANISM: Corynebacterium glutamicum

<400> SEQUENCE: 45
atgattcgcg tgctgcttgc tgatgaccac gaaatcgtga ggctcggact ccgggctgtg      60
ctggaaagcg ccgaggacat tgaagtggtg ggcgaagtct ccaccgccga aggtgcggtg     120
caggcagccc gagaaggcgg aatcgacgtc atcttgatgg acctccgatt cggccccggc     180
gtccaaggaa cccaggtatc caccggcgca gacgccaccg cagccatcaa gcgaaacatc     240
gataacccgc caaaagtcct ggttgtgacc aactacgaca ccgacacaga catcctcggc     300
gcaatcgaag ccggcgcact gggctacctg ctcaaagacg ccccaccgag cgaactcctg     360
gcagcagtac gatccgcagc agaaggtgac tccacactgt cacccatggt tgctaaccgc     420
ctgatgactc gcgtgcgaac ccccaaaacc tcactcaccc cacgcgagct ggaggttctc     480
aaactggtcg ccggcggttc ctccaaccgc gacattggcc gtatcctctt cctctcagaa     540
gccacgtgaa atcccacct cgtgcacatc tacgacaagc tcggcgtgcg gtcacgtacc     600
tccgctgtcg cagccgcacg tgagcagggg ctgctgtag     639
```

```
<210> SEQ ID NO 46
<211> LENGTH: 212
<212> TYPE: PRT
<213> ORGANISM: Corynebacterium glutamicum

<400> SEQUENCE: 46

Met Ile Arg Val Leu Leu Ala Asp Asp His Glu Ile Val Arg Leu Gly
1               5                   10                  15

Leu Arg Ala Val Leu Glu Ser Ala Glu Asp Ile Glu Val Val Gly Glu
                20                  25                  30

Val Ser Thr Ala Glu Gly Ala Val Gln Ala Ala Arg Glu Gly Gly Ile
            35                  40                  45

Asp Val Ile Leu Met Asp Leu Arg Phe Gly Pro Gly Val Gln Gly Thr
        50                  55                  60

Gln Val Ser Thr Gly Ala Asp Ala Thr Ala Ala Ile Lys Arg Asn Ile
65                  70                  75                  80

Asp Asn Pro Pro Lys Val Leu Val Val Thr Asn Tyr Asp Thr Asp Thr
                85                  90                  95

Asp Ile Leu Gly Ala Ile Glu Ala Gly Ala Leu Gly Tyr Leu Leu Lys
            100                 105                 110

Asp Ala Pro Pro Ser Glu Leu Leu Ala Ala Val Arg Ser Ala Ala Glu
        115                 120                 125

Gly Asp Ser Thr Leu Ser Pro Met Val Ala Asn Arg Leu Met Thr Arg
    130                 135                 140

Val Arg Thr Pro Lys Thr Ser Leu Thr Pro Arg Glu Leu Glu Val Leu
145                 150                 155                 160

Lys Leu Val Ala Gly Gly Ser Ser Asn Arg Asp Ile Gly Arg Ile Leu
                165                 170                 175

Phe Leu Ser Glu Ala Thr Val Lys Ser His Leu Val His Ile Tyr Asp
            180                 185                 190

Lys Leu Gly Val Arg Ser Arg Thr Ser Ala Val Ala Ala Ala Arg Glu
        195                 200                 205

Gln Gly Leu Leu
    210

<210> SEQ ID NO 47
<211> LENGTH: 1026
<212> TYPE: DNA
<213> ORGANISM: Corynebacterium glutamicum

<400> SEQUENCE: 47
gtgagtgcaa cagagaaacg tagatacgaa gtgttgcggg ccatcgtcgc tgattacatt      60
gcgtctcagg aacctgtcgg atcgaagtca ctcctcgagc gccataagct caacgtgagt     120
tctgcgacga tccgcaacga tatgtcggtg ctggaatccg atggctttat cgtccaggag     180
catgcaagtt ctggccgggt accaaccgaa aagggttacc gcctttttgt tgattccatc     240
catgacatca agccgctgtc gctggcggaa cggcgcgcta ttttgggctt ccttgaaggg     300
ggagtggact tagaggacgt gctgcgcagg tctgtgcagc tgttgtctca gctcacccat     360
caggctgccg tggtgcagct gcccaccttg aaaacagcgc gcgtgaagca ctgcgaggtg     420
gtgccgctgt cgccgatgcg cttgctgctg gtgctcatta ccgatactgg ccgtgtagat     480
cagcgcaacg tggaacttga ggaaccgctg cggcgcgaag aagttaatgt gctgcgcgat     540
ctgctcaacg gcgcgctagg ggagaaaacg ctgacggctg catcagatgc gctggaggag     600
```

```
ttggctcagc aagccccaac cgatattcgt gatgccatgc gccgctgctg cgatgtactg     660
gtgaacacgc ttgtcgatca accctctgac cgcctgatcc tcgccggcac ctcaaacctc     720
acccgcttaa gcagggaaac ctccgcgagc ctaccgatgg ttttagaagc cttggaagag     780
caggtggtca tgttgaaact gctgtccaat gtcactgatc ttgaccaagt gagcgtgcat     840
attggcggcg aaaatgaaga cattgagctg cgcagcgcaa cggtgattac caccggttac     900
ggctcccagg gcagcgcact gggcggattg ggggtggttg gccccaccta tatggactac     960
tcgggaacaa tttctaaggt gtccgccgtt gctaagtatg ttggtcgtgt gctcgctggc    1020
gaatag                                                              1026
```

<210> SEQ ID NO 48
<211> LENGTH: 341
<212> TYPE: PRT
<213> ORGANISM: Corynebacterium glutamicum

<400> SEQUENCE: 48

```
Met Ser Ala Thr Glu Lys Arg Arg Tyr Glu Val Leu Arg Ala Ile Val
1               5                   10                  15

Ala Asp Tyr Ile Ala Ser Gln Glu Pro Val Gly Ser Lys Ser Leu Leu
            20                  25                  30

Glu Arg His Lys Leu Asn Val Ser Ser Ala Thr Ile Arg Asn Asp Met
        35                  40                  45

Ser Val Leu Glu Ser Asp Gly Phe Ile Val Gln Glu His Ala Ser Ser
    50                  55                  60

Gly Arg Val Pro Thr Glu Lys Gly Tyr Arg Leu Phe Val Asp Ser Ile
65                  70                  75                  80

His Asp Ile Lys Pro Leu Ser Leu Ala Glu Arg Arg Ala Ile Leu Gly
                85                  90                  95

Phe Leu Glu Gly Gly Val Asp Leu Glu Asp Val Leu Arg Arg Ser Val
            100                 105                 110

Gln Leu Leu Ser Gln Leu Thr His Gln Ala Ala Val Val Gln Leu Pro
        115                 120                 125

Thr Leu Lys Thr Ala Arg Val Lys His Cys Glu Val Val Pro Leu Ser
    130                 135                 140

Pro Met Arg Leu Leu Leu Val Leu Ile Thr Asp Thr Gly Arg Val Asp
145                 150                 155                 160

Gln Arg Asn Val Glu Leu Glu Glu Pro Leu Ala Ala Glu Glu Val Asn
                165                 170                 175

Val Leu Arg Asp Leu Leu Asn Gly Ala Leu Gly Glu Lys Thr Leu Thr
            180                 185                 190

Ala Ala Ser Asp Ala Leu Glu Glu Leu Ala Gln Gln Ala Pro Thr Asp
        195                 200                 205

Ile Arg Asp Ala Met Arg Arg Cys Cys Asp Val Leu Val Asn Thr Leu
    210                 215                 220

Val Asp Gln Pro Ser Asp Arg Leu Ile Leu Ala Gly Thr Ser Asn Leu
225                 230                 235                 240

Thr Arg Leu Ser Arg Glu Thr Ser Ala Ser Leu Pro Met Val Leu Glu
                245                 250                 255

Ala Leu Glu Glu Gln Val Val Met Leu Lys Leu Leu Ser Asn Val Thr
            260                 265                 270

Asp Leu Asp Gln Val Ser Val His Ile Gly Gly Glu Asn Glu Asp Ile
        275                 280                 285

Glu Leu Arg Ser Ala Thr Val Ile Thr Thr Gly Tyr Gly Ser Gln Gly
```

```
            290                 295                 300

Ser Ala Leu Gly Gly Leu Gly Val Val Gly Pro Thr Tyr Met Asp Tyr
305                 310                 315                 320

Ser Gly Thr Ile Ser Lys Val Ser Ala Val Ala Lys Tyr Val Gly Arg
                    325                 330                 335

Val Leu Ala Gly Glu
            340
```

<210> SEQ ID NO 49
<211> LENGTH: 22
<212> TYPE: DNA
<213> ORGANISM: Artificial Sequence
<220> FEATURE:
<223> OTHER INFORMATION: primer

<400> SEQUENCE: 49
gaattgggca tcgtccacga aa                                                22

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
caacgatcag gattgtcgtc atg                                               23

<210> SEQ ID NO 51
<211> LENGTH: 45
<212> TYPE: DNA
<213> ORGANISM: Artificial Sequence
<220> FEATURE:
<223> OTHER INFORMATION: primer

<400> SEQUENCE: 51
catgacgaca atcctgatcg ttggcgtgga ttgggctaca aattc                       45

<210> SEQ ID NO 52
<211> LENGTH: 22
<212> TYPE: DNA
<213> ORGANISM: Artificial Sequence
<220> FEATURE:
<223> OTHER INFORMATION: primer

<400> SEQUENCE: 52
gctaattatg ggcatccaag gg                                                22

<210> SEQ ID NO 53
<211> LENGTH: 34
<212> TYPE: DNA
<213> ORGANISM: Artificial Sequence
<220> FEATURE:
<223> OTHER INFORMATION: primer

<400> SEQUENCE: 53
tcgagctcgg tacccccaaa aggaatcagg ccag                                   34

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
gacctagttc aaacacggga ggctgctgta gcg                                    33

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
tgtttgaact aggtccttcc                                                   20

<210> SEQ ID NO 56
<211> LENGTH: 33
<212> TYPE: DNA
<213> ORGANISM: Artificial Sequence
<220> FEATURE:
<223> OTHER INFORMATION: primer

<400> SEQUENCE: 56
ctctagagga tccccggttg acctttggtg gtg                                    33

<210> SEQ ID NO 57
<211> LENGTH: 21
<212> TYPE: DNA
<213> ORGANISM: Artificial Sequence
<220> FEATURE:
<223> OTHER INFORMATION: primer

<400> SEQUENCE: 57
catcattggg ctgagtacct g                                                 21

<210> SEQ ID NO 58
<211> LENGTH: 22
<212> TYPE: DNA
<213> ORGANISM: Artificial Sequence
<220> FEATURE:
<223> OTHER INFORMATION: primer

<400> SEQUENCE: 58
cgaatagctg cgggtatagt tg                                                22

<210> SEQ ID NO 59
<211> LENGTH: 44
<212> TYPE: DNA
<213> ORGANISM: Artificial Sequence
<220> FEATURE:
<223> OTHER INFORMATION: primer

<400> SEQUENCE: 59
caactatacc cgcagctatt cgtacgtttc tctgttgcac tcac                        44

<210> SEQ ID NO 60
<211> LENGTH: 21
<212> TYPE: DNA
<213> ORGANISM: Artificial Sequence
<220> FEATURE:
<223> OTHER INFORMATION: primer

<400> SEQUENCE: 60
gttgattggt gcggacggtt t                                                 21

<210> SEQ ID NO 61
<211> LENGTH: 117

<212> TYPE: PRT
<213> ORGANISM: Vicugna pacos

<400> SEQUENCE: 61

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Asp
            20                  25                  30

Ala Met Thr Trp Val Arg Gln Ala Pro Gly Lys Ala Leu Glu Trp Val
        35                  40                  45

Ser Ser Ile Thr Leu Leu Gly Gly Ile Pro Tyr Tyr Ser Asp Thr
    50                  55                  60

Val Lys Gly Arg Phe Thr Ile Ser Arg Asp Asn Thr Lys Asn Met Leu
65                  70                  75                  80

Tyr Leu Gln Met Asn Ser Leu Lys Pro Glu Asp Thr Ala Val Tyr Tyr
                85                  90                  95

Cys Ala Lys Gly Phe Lys Ser Asp Tyr Pro Arg Gly Gln Gly Thr Gln
            100                 105                 110

Val Thr Val Ser Ser
        115

<210> SEQ ID NO 62
<211> LENGTH: 354
<212> TYPE: DNA
<213> ORGANISM: Vicugna pacos

<400> SEQUENCE: 62
caggttcagc ttgtggaatc cggcggtggc ttggtgcagc ctggtggctc ccttcgcttg      60
tcttgcgcag cttccggctt caccttctcc aacgatgcaa tgacctgggt ccgtcaggca     120
cctggtaaag cgcttgagtg gtttcctct atcaccctgc tcggtggcgg tattccatac      180
tactctgata ccgtgaaggg ccgcttcacc atctcccgtg acaacaccaa aaacatgctg     240
tacctgcaga tgaactctct caagccagaa gataccgcag tctactactg tgctaagggt     300
ttcaaatccg actaccctcg cggtcagggc acccaggtga ccgtctcctc ttag           354

<210> SEQ ID NO 63
<211> LENGTH: 154
<212> TYPE: PRT
<213> ORGANISM: Homo sapiens

<400> SEQUENCE: 63

Ala Ala Gly Ser Ile Thr Thr Leu Pro Ala Leu Pro Glu Asp Gly Gly
1               5                   10                  15

Ser Gly Ala Phe Pro Pro Gly His Phe Lys Asp Pro Lys Arg Leu Tyr
            20                  25                  30

Cys Lys Asn Gly Gly Phe Phe Leu Arg Ile His Pro Asp Gly Arg Val
        35                  40                  45

Asp Gly Val Arg Glu Lys Ser Asp Pro His Ile Lys Leu Gln Leu Gln
    50                  55                  60

Ala Glu Glu Arg Gly Val Val Ser Ile Lys Gly Val Cys Ala Asn Arg
65                  70                  75                  80

Tyr Leu Ala Met Lys Glu Asp Gly Arg Leu Leu Ala Ser Lys Cys Val
                85                  90                  95

Thr Asp Glu Cys Phe Phe Phe Glu Arg Leu Glu Ser Asn Asn Tyr Asn
            100                 105                 110

Thr Tyr Arg Ser Arg Lys Tyr Thr Ser Trp Tyr Val Ala Leu Lys Arg

-continued

```
        115                  120                  125
Thr Gly Gln Tyr Lys Leu Gly Ser Lys Thr Gly Pro Gly Gln Lys Ala
    130                  135                  140

Ile Leu Phe Leu Pro Met Ser Ala Lys Ser
145                  150

<210> SEQ ID NO 64
<211> LENGTH: 465
<212> TYPE: DNA
<213> ORGANISM: Homo sapiens

<400> SEQUENCE: 64
gctgccggat ctattaccac gctcccggcg ctcccggaag acggtggaag cggcgccttc      60
ccacctggcc acttcaaaga cccgaaacgt ctgtattgta aaaatggcgg ttttttcctc     120
cgcatccacc cagatggtcg cgtcgatggt gtccgcgaaa agtccgaccc acacatcaag     180
ctgcaactgc aagcagagga acgtggcgtc gtgagcatca agggcgtgtg cgcaaaccgc     240
tatctggcca tgaaggagga tggtcgcctt cttgcatcca aatgcgtgac cgatgaatgc     300
ttcttctttg aacggctgga gtccaacaat tacaacacct accgctcccg caagtatacc     360
tcctggtatg tcgccctgaa acgcacggga caatataaac tgggttccaa gaccggtcct     420
ggccaaaagg cgattctttt cctcccaatg tccgcgaagt cttga                    465
```

METHOD FOR SECRETORY PRODUCTION OF PROTEIN

This application is a Continuation of, and claims priority under 35 U.S.C. § 120 to, International Application No. PCT/JP2019/017100, filed Apr. 22, 2019, and claims priority therethrough under 35 U.S.C. §§ 119, 365 to Japanese Patent Application No. 2018-081138, filed Apr. 20, 2018, the entireties of which are incorporated by reference herein. Also, the Sequence Listing filed electronically herewith is hereby incorporated by reference (File name: 2020-10-16T_US-615 Seq List; File size: 78,767 bytes; Date recorded: Oct. 16, 2020).

TECHNICAL FIELD

The present disclosure relates to methods for secretory production of a heterologous protein.

BACKGROUND

As secretory production of heterologous proteins by microorganisms, there have been reported secretory productions of heterologous proteins by a *Bacillus* bacterium (Microbiol. Rev., 57, 109-137 (1993)), methanol-assimilating yeast, *Pichia pastoris* (Biotechnol., 11, 905-910 (1993)), filamentous fungi of the genus *Aspergillus* (Biotechnol., 6, 1419-1422 (1988) and Biotechnol., 9, 976-981 (1991)), and so forth.

There are also attempted secretory productions of heterologous proteins by coryneform bacteria. As for secretory productions of heterologous proteins by coryneform bacteria, there have been reported secretion of a nuclease and a lipase by *Corynebacterium glutamicum* (henceforth also abbreviated as *C. glutamicum*) (U.S. Pat. No. 4,965,197, J. Bacteriol., 174, 1854-1861 (1992)), secretion of a protease such as subtilisin (Appl. Environ. Microbiol., 61, 1610-1613 (1995)), secretion of a protein using signal peptides of cell surface layer proteins PS1 and PS2 (also referred to as CspB) of coryneform bacteria (Japanese Patent Laid-open (Kohyo) No. 6-502548), secretion of a fibronectin-binding protein using the signal peptide of PS2 (CspB) (Appl. Environ. Microbiol., 63, 4392-4400 (1997)), secretion of protransglutaminase using signal peptides of PS2 (CspB) and SlpA (also referred to as CspA) (Japanese Patent No. 4320769), secretion of a protein using a variant type secretion system (Japanese Patent Laid-open (Kokai) No. 11-169182), secretion of a protransglutaminase by a variant strain (Japanese Patent No. 4362651), and so forth. In addition, as techniques for improving secretory production amounts of heterologous proteins by coryneform bacteria, there are known reducing the activity of a cell surface layer protein (WO2013/065869 and WO2013/065772), reducing the activity of a penicillin-binding protein (WO2013/065869), enhancing the expression of a gene encoding a metallopeptidase (WO2013/065772), introducing a mutation into a ribosomal protein S1 gene (WO2013/118544), expressing a heterologous protein with an amino acid sequence including Gln-Glu-Thr inserted between a signal peptide and the heterologous protein (WO2013/062029), and so forth.

A general protein secretion pathway is a pathway called "Sec system", which is widely present from prokaryotes to eukaryotes; however, a protein secretion pathway completely different from the Sec system has recently been found in thylakoid membranes of chloroplasts of plant cells (EMBO J., 14, 2715-2722 (1995)). This novel secretory pathway has been named "Tat system" (Twin-Arginine Translocation system) because an arginine-arginine sequence is commonly present in the signal sequence of a protein secreted thereby (EMBO J., 14, 2715-2722 (1995)). It is known that proteins are secreted by the Sec system in a state before forming a higher-order structure, while proteins are secreted by the Tat system through a cell membrane after forming a higher-order structure in the cell (J. Biol. Chem., 25; 273 (52), 34868-74 (1998)). Also for coryneform bacteria, secretory production of proteins utilizing a Tat-dependent signal peptide has been reported (WO2013/118544 and Japanese Patent No. 4730302).

As a system by which bacteria respond to various environmental changes inside and outside the cell, a signaling pathway called a "two-component regulatory system" is known. The two-component regulatory system is a regulatory system formed of two components: a sensor kinase that is responsible for sensing a stimulus of an environmental change, and a response regulator that is responsible for receiving a signal from the sensor kinase and regulating the expression of downstream genes. Specifically, when the sensor kinase senses a stimulus, a specific histidine residue thereof is autophosphorylated, a signal is transduced via transfer of the phosphate group to a specific aspartic acid residue of the response regulator, and the response regulator activated by phosphorylation regulates the expression of downstream genes as a transcription factor.

Knowledge concerning the two-component regulatory system of *C. glutamicum* is detailed in Appl. Microbiol. Biotechnol., 94, 1131-1150 (2012) etc. For *C. glutamicum*, at least 13 types of systems have been known as the two-component regulatory system. Specific examples of the two-component regulatory system include the PhoRS system, the SenX3-RegX3 system, and the HrrSA system.

The PhoRS system is formed of a sensor kinase PhoS protein and a response regulator PhoR protein. Analysis of a PhoRS-deficient strain revealed that the PhoRS system is a regulatory system that senses phosphate depletion in the environment and performs signal transduction (J. Bacteriol., 188, 724-732 (2006)).

The SenX3-RegX3 system is formed of a sensor kinase SenX3 protein and a response regulator RegX3 protein. Since no RegX3-deficient strain of *C. glutamicum* ATCC 13032 was able to be obtained, the SenX3-RegX3 system has been considered to be an essential system for the ATCC 13032 strain (Appl. Microbiol. Biotechnol., 94, 1131-1150 (2012) and Han Min Woo, Regulatory and metabolic aspects of the phosphate starvation response of *Corynebacterium glutamicum*, URN (NBN): urn:nbn:de:hbz:061-20100825-090114-5, Duesseldorf University Doctoral Dissertation (2010)). Meanwhile, analysis of a strain having an attenuated expression of the regX3 gene revealed that the SenX3-RegX3 system induces the expression of genes responding to depletion of inorganic phosphate and genes involved in biosynthesis of NAD$^+$ (Han Min Woo, Regulatory and metabolic aspects of the phosphate starvation response of *Corynebacterium glutamicum*, URN (NBN): urn:nbn:de:hbz:061-20100825-090114-5, Duesseldorf University Doctoral Dissertation (2010)).

However, the relationship between the SenX3-RegX3 system and secretory production of heterologous proteins is not known.

The HrrSA system is formed of a sensor kinase HrrS protein and a response regulator HrrA protein. Analysis of a HrrSA-deficient strain revealed that the HrrSA system, in the presence of haem, induces the expression of genes involved in degradation of haem and genes encoding haem-containing proteins in the respiratory chain, and represses the expression of genes involved in biosynthesis of haem, and hence, it is considered that the HrrSA system is involved in homeostasis of haem (J. Bacteriol., 193, 1212-1221 (2011)).

However, the relationship between the HrrSA system and secretory production of heterologous proteins is not known.

Any organisms express various proteins called heat-shock proteins in response to a sudden increase in temperature (heat-shock). Heat-shock proteins include molecular chaperones, which help folding of proteins, and proteases, which degrade misfolded proteins. GroEL, one of the molecular chaperones, forms a GroEL-GroES complex in combination with a cofactor GroES, and folding of proteins takes place inside the complex. Two copies of groEL gene, i.e., groEL1 gene (NCBI locus_tag CGBL_0106870) and groEL2 gene (NCBI locus_tag CGBL_0126550), and one copy of groES gene (NCBI locus_tag CGBL_0106860) are present in the genome of *Corynebacterium glutamicum* (GenBank Accession No. AP017557). It has been known that a transcription factor HrcA encoded by hrcA gene (NCBI locus_tag CGBL_0121890) suppresses transcription of groEL1, groEL2, and groES genes, and the transcription levels of groEL1, groEL2, and groES are increased in a strain deficient in the hrcA gene (J. Bacteriol., 191, 2964-2072 (2009)). In addition, it has been confirmed that coexpression of GroEL and GroES results in an increase in the yield and solubility of various heterologous proteins in *E. coli* (Microb. Cell. Fact., 8: 9 (2009)).

However, the relationship between HrcA, GroEL, or GroES and secretory production of heterologous proteins in coryneform bacteria is not known.

SUMMARY

One of numerous aspects of the subject matter of the present disclosure is a novel technique for improving secretory production of a heterologous protein by a coryneform bacterium, and thereby to provide a method for secretory production of a heterologous protein using a coryneform bacterium.

The inventors of the subject matter of the present disclosure conducted various researches in order to achieve the aforementioned aspect. As a result, they found that an ability of a coryneform bacterium to produce a heterologous protein by secretory production can be improved by modifying the coryneform bacterium so that the activity of two or more of RegX3 protein, HrrSA system, and HrcA protein are reduced.

The subject matter of the present disclosure can be thus embodied as follows.

A method for producing a heterologous protein comprising:

culturing a coryneform bacterium having a genetic construct for secretory expression of the heterologous protein; and collecting the heterologous protein produced by secretory production, wherein the coryneform bacterium has been modified to have a combination of two or more features selected from the features (A), (B), and (C):

(A) the activity of a RegX3 protein is reduced as compared with a non-modified strain;

(B) the activity of a HrrSA system is reduced as compared with a non-modified strain;

(C) the activity of a HrcA protein is reduced as compared with a non-modified strain, wherein the genetic construct comprises, in the direction from 5' to 3', a promoter sequence that functions in the coryneform bacterium, a nucleic acid sequence encoding a signal peptide that functions in the coryneform bacterium, and a nucleic acid sequence encoding the heterologous protein, and wherein the heterologous protein is expressed as a fusion protein with the signal peptide.

The method mentioned above, wherein the features (A), (B), and (C) are the features (A1), (B1), and (C1), respectively:

(A1) the number of molecules of the RegX3 protein per cell is reduced as compared with a non-modified strain;

(B1) the number of molecules of either one or both of a HrrS protein and a HrrA protein per cell is reduced as compared with a non-modified strain;

(C1) the number of molecules of the HrcA protein per cell is reduced as compared with a non-modified strain.

The method mentioned above, wherein the coryneform bacterium has a combination of the feature (A) and (B), a combination of the feature (A) and (C), or a combination of the feature (B) and (C).

The method mentioned above, wherein the coryneform bacterium has a combination of the feature (A), (B), and (C).

The method mentioned above, wherein the feature (B) is obtained by reducing the activity of at least one of an HrrS protein and an HrrA protein.

The method mentioned above, wherein the feature (B) is obtained by reducing at least the activity of the HrrA protein.

The method mentioned above, wherein the feature (B) is obtained by reducing the number of molecules of at least one of an HrrS protein and an HrrA protein per cell.

The method mentioned above, wherein the feature (B) is obtained by reducing at least the number of molecules of the HrrA protein per cell.

The method mentioned above, wherein the RegX3 protein is a protein defined in (a), (b), or (c):

(a) a protein comprising the amino acid sequence of SEQ ID NO: 42;

(b) a protein comprising the amino acid sequence of SEQ ID NO: 42, but which includes substitution, deletion, insertion, and/or addition of 1 to 10 amino acid residues, wherein said protein has a function as a response regulator of an SenX3-RegX3 system;

(c) a protein comprising an amino acid sequence showing an identity of 90% or higher to the amino acid sequence of SEQ ID NO: 42, wherein said protein has a function as a response regulator of a SenX3-RegX3 system.

The method mentioned above, wherein the HrrS protein is a protein defined in (a), (b), or (c):

(a) a protein comprising the amino acid sequence of SEQ ID NO: 44;

(b) a protein comprising the amino acid sequence of SEQ ID NO: 44, but which includes substitution, deletion, insertion, and/or addition of 1 to 10 amino acid residues, wherein said protein has a function as a sensor kinase of an HrrSA system;

(c) a protein comprising an amino acid sequence showing an identity of 90% or higher to the amino acid sequence of SEQ ID NO: 44, wherein said protein has a function as a sensor kinase of an HrrSA system.

The method mentioned above, wherein the HrrA protein is a protein defined in (a), (b), or (c):

(a) a protein comprising the amino acid sequence of SEQ ID NO: 46;

(b) a protein comprising the amino acid sequence of SEQ ID NO: 46, but which includes substitution, deletion, insertion, and/or addition of 1 to 10 amino acid residues, wherein said protein has a function as a response regulator of an HrrSA system;

(c) a protein comprising an amino acid sequence showing an identity of 90% or higher to the amino acid sequence of SEQ ID NO: 46, wherein said protein has a function as a response regulator of an HrrSA system.

The method mentioned above, wherein the HrcA protein is a protein defined in (a), (b), or (c):

(a) a protein comprising the amino acid sequence of SEQ ID NO: 48;

(b) a protein comprising the amino acid sequence of SEQ ID NO: 48, but which includes substitution, deletion, insertion, and/or addition of 1 to 10 amino acid residues, wherein said protein has a function as a transcription repressor of heat-shock proteins;

(c) a protein comprising an amino acid sequence showing an identity of 90% or higher to the amino acid sequence of SEQ ID NO: 48, wherein said protein has a function as a transcription repressor of heat-shock proteins.

The method mentioned above, wherein:

the feature (A) is obtained by reducing the expression of a regX3 gene, or by disrupting a regX3 gene;

the feature (B) is obtained by reducing the expression of an hrrS gene and/or an hrrA gene, or by disrupting an hrrS gene and/or an hrrA gene; and/or the feature (C) is obtained by reducing the expression of an hrcA gene, or by disrupting an hrcA gene.

The method mentioned above, wherein:

the feature (A) is obtained by deleting a regX3 gene;

the feature (B) is obtained by deleting an hrrS gene and/or an hrrA gene; and/or the feature (C) is obtained by deleting an hrcA gene.

The method mentioned above, wherein the coryneform bacterium has been further modified to harbor a phoS gene encoding a mutant PhoS protein.

The method mentioned above, wherein the mutation is a mutation of replacing an amino acid residue corresponding to the tryptophan residue at position 302 in SEQ ID NO: 2 with an amino acid residue other than aromatic amino acid and histidine residues in a wild-type PhoS protein.

The method mentioned above, wherein the amino acid residue other than aromatic amino acid and histidine residues is a lysine residue, alanine residue, valine residue, serine residue, cysteine residue, methionine residue, aspartic acid residue, or asparagine residue.

The method mentioned above, wherein the wild-type PhoS protein is a protein defined in (a), (b), or (c):

(a) a protein comprising any of the amino acid sequences of SEQ ID NOS: 2 to 7;

(b) a protein comprising any of the amino acid sequences of SEQ ID NOS: 2 to 7, but which includes substitution, deletion, insertion, and/or addition of 1 to 10 amino acid residues, wherein said protein has a function as a sensor kinase of a PhoRS system;

(c) a protein comprising an amino acid sequence showing an identity of 90% or higher to any of the amino acid sequences of SEQ ID NOS: 2 to 7, wherein said protein has a function as a sensor kinase of a PhoRS system.

The method mentioned above, wherein the signal peptide is a Tat-dependent signal peptide.

The method mentioned above, wherein the Tat-dependent signal peptide is a signal peptide selected from the group consisting of a TorA signal peptide, SufI signal peptide, PhoD signal peptide, LipA signal peptide, and IMD signal peptide.

The method mentioned above, wherein the coryneform bacterium has been further modified so that the expression of one or more genes selected from genes encoding a Tat secretion system is increased as compared with a non-modified strain.

The method mentioned above, wherein the genes encoding a Tat secretion system consists of a tatA gene, tatB gene, tatC gene, and tatE gene.

The method mentioned above, wherein the signal peptide is a Sec-dependent signal peptide.

The method mentioned above, wherein the Sec-dependent signal peptide is a signal peptide selected from the group consisting of a PS1 signal peptide, PS2 signal peptide, and SlpA signal peptide.

The method mentioned above, wherein the genetic construct further comprises a nucleic acid sequence encoding an amino acid sequence comprising Gln-Glu-Thr between the nucleic acid sequence encoding the signal peptide that functions in the coryneform bacterium and the nucleic acid sequence encoding the heterologous protein.

The method mentioned above, wherein the genetic construct further comprises a nucleic acid sequence encoding an amino acid sequence used for enzymatic digestion between the nucleic acid sequence encoding the amino acid sequence comprising Gln-Glu-Thr and the nucleic acid sequence encoding the heterologous protein.

The method mentioned above, wherein the coryneform bacterium is a bacterium belonging to the genus *Corynebacterium*.

The method mentioned above, wherein the coryneform bacterium is *Corynebacterium glutamicum*.

The method mentioned above, wherein the coryneform bacterium is a modified strain derived from *Corynebacterium glutamicum* AJ12036 (FERM BP-734) or a modified strain derived from *Corynebacterium glutamicum* ATCC 13869.

The method mentioned above, wherein the coryneform bacterium is a coryneform bacterium in which the number of molecules of a cell surface layer protein per cell is reduced as compared with a non-modified strain.

DETAILED DESCRIPTON

Figure 1:
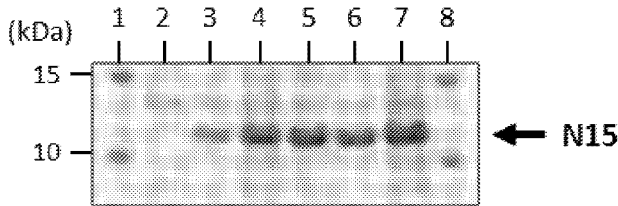
FIG. 1 is a photograph showing the results of SDS-PAGE observed upon expressing VHH antibody N15 (N15 fused with CspA signal sequence) in the *C. glutamicum* YDK010::phoS(W302C) strain and gene-deficient strains thereof.

Methods of the present disclosure include a method for producing a heterologous protein, the method including culturing a coryneform bacterium having a genetic construct for secretory expression of the heterologous protein, and collecting the heterologous protein produced by secretory production, wherein the coryneform bacterium has been modified so as to have a specific feature.

<1> Coryneform Bacterium Used for Methods of the Present Disclosure

The coryneform bacterium used for methods of the present disclosure is a coryneform bacterium having a genetic construct for secretory expression of a heterologous protein, which has been modified so as to have a specific feature. The coryneform bacterium used for methods of the present disclosure is also referred to as "bacterium of the present disclosure" or "coryneform bacterium of the present disclosure". Furthermore, the genetic construct for secretory expression of a heterologous protein harbored by the bacterium of the present disclosure is also referred to as "genetic construct used for the present disclosure".

<1-1> Coryneform Bacterium Having Ability of Secretory Production of Heterologous Protein The coryneform bacterium of the present disclosure has the genetic construct for secretory expression of a heterologous protein (genetic construct used for methods of the present disclosure), and therefore has an ability of secretory production of the heterologous protein.

In the present disclosure, the expression that a protein is "secreted" means that the protein is transported out of a bacterial cell (extracellularly transported). Examples of a position outside of a bacterial cell (outside of a cell) include a medium and a cell surface layer. That is, molecules of the secreted protein may be present, for example, in the medium, in the cell surface layer, or in both the medium and the cell surface layer. That is, the expression that a protein is "secreted" is not limited to cases where all the molecules of the protein eventually exist in the medium in completely free forms, and also include, for example, cases where all the molecules of the protein exist in the cell surface layer, and cases where a part of the molecules of the protein exists in the medium and the remaining part of the molecules of the protein exists in the cell surface layer.

That is, in the present disclosure, the term "ability to produce a heterologous protein by secretory production" refers to an ability of the bacterium of the present disclosure to secrete the heterologous protein into a medium and/or a cell surface layer, and accumulate it there to such an extent that the heterologous protein can be collected from the medium and/or the cell surface layer, when the bacterium is cultured in the medium. The accumulation amount may be, for example, in terms of the accumulation amount in the medium, 10 µg/L or more, 1 mg/L or more, 100 mg/L or more, or 1 g/L or more. Also, the accumulation amount may be, for example, in terms of the accumulation amount in the cell surface layer, such an amount that if the heterologous protein in the cell surface layer is collected and suspended in a liquid of the same volume as the medium, the concentration of the heterologous protein in the suspension is 10 µg/L or more, 1 mg/L or more, or 100 mg/L or more. In addition, in the present disclosure, the term "protein" to be produced by secretory production refers to a concept also including those called peptide, such as oligopeptides and polypeptides.

In the present disclosure, the term "heterologous protein" refers to an exogenous protein relative to a coryneform bacterium that expresses and secretes that protein. The heterologous protein may be, for example, a protein derived from a microorganism, a protein derived from a plant, a protein derived from an animal, a protein derived from a virus, or even a protein of which the amino acid sequence is artificially designed. The heterologous protein may particularly be a derived from human. The heterologous protein may be a monomeric protein or a multimeric protein. The term "multimeric protein" refers to a protein that may exist as a multimer formed of two or more subunits. In the multimer, the subunits may be linked by covalent bonds such as disulfide bonds, linked by non-covalent bonds such as hydrogen bonds and hydrophobic interaction, or linked by a combination thereof. The multimer may include one or more intermolecular disulfide bonds. The multimer may be a homo-multimer formed of a single kind of subunit, or may be a hetero-multimer formed of two or more kinds of subunits. In the case where the multimeric protein is a hetero-multimer, it is sufficient that at least one subunit selected from the subunits constituting the hetero-multimer is a heterologous protein. That is, all the subunits may be heterologous, or only a part of subunits may be heterologous. Although the heterologous protein may be a secretory protein in nature, or may be a non-secretory protein in nature, it is preferably a secretory protein in nature. Furthermore, the heterologous protein may be a Tat-dependent secretory protein in nature, or may be a Sec-dependent secretory protein in nature. Specific examples of the "heterologous protein" will be described elsewhere herein.

The heterologous protein to be produced may be formed of a single kind of protein, or two or more kinds of proteins. Moreover, when the heterologous protein is a hetero-multimer, only one kind of subunit may be produced, or two or more kinds of subunits may be produced. That is, the term "secretory production of a heterologous protein" includes secretory production of all the subunits constituting an objective heterologous protein, as well as secretory production of only a part of the subunits constituting an objective heterologous protein.

Coryneform bacteria are aerobic gram-positive bacilli. Examples of the coryneform bacteria include *Corynebacterium* bacteria, *Brevibacterium* bacteria, *Microbacterium* bacteria, and so forth. Advantages of use of the coryneform bacteria include that they inherently secrete an extremely small amount of proteins out of cells compared with fungi, yeasts, *Bacillus* bacteria, etc., which are conventionally used for secretory production of proteins, and therefore the purification process of a heterologous protein produced by secretory production is expected to be simplified or eliminated, that they can grow well in a simple medium containing a saccharide, ammonia, mineral salts, etc., and therefore they are excellent in view of cost of medium, culture method, and culture productivity, and so forth.

Specific examples of coryneform bacteria include the following species:

*Corynebacterium acetoacidophilum*
*Corynebacterium acetoglutamicum*
*Corynebacterium alkanolyticum*
*Corynebacterium callunae*
*Corynebacterium crenatum*
*Corynebacterium glutamicum*
*Corynebacterium lilium*
*Corynebacterium melassecola*
*Corynebacterium thermoaminogenes* (*Corynebacterium efficiens*)
*Corynebacterium herculis*
*Brevibacterium divaricatum* (*Corynebacterium glutamicum*)
*Brevibacterium flavum* (*Corynebacterium glutamicum*)
*Brevibacterium immariophilum*
*Brevibacterium lactofermentum* (*Corynebacterium glutamicum*)
*Brevibacterium roseum*
*Brevibacterium saccharolyticum*
*Brevibacterium thiogenitalis*

*Corynebacterium ammoniagenes (Corynebacterium sta-*
*tionis)*
*Brevibacterium album*
*Brevibacterium cerinum*
*Microbacterium ammoniaphilum*

Specific examples of coryneform bacteria include the
following strains:
*Corynebacterium acetoacidophilum* ATCC 13870
*Corynebacterium acetoglutamicum* ATCC 15806
*Corynebacterium alkanolyticum* ATCC 21511
*Corynebacterium callunae* ATCC 15991
*Corynebacterium crenatum* AS1.542
*Corynebacterium glutamicum* ATCC 13020, ATCC
13032, ATCC 13060, ATCC 13869, FERM BP-734
*Corynebacterium lilium* ATCC 15990
*Corynebacterium melassecola* ATCC 17965
*Corynebacterium thermoaminogenes (Corynebacterium*
*efficiens)* AJ12340 (FERM BP-1539)
*Corynebacterium herculis* ATCC 13868
*Brevibacterium divaricatum (Corynebacterium glutami-*
*cum)* ATCC 14020
*Brevibacterium flavum (Corynebacterium glutamicum)*
ATCC 13826, ATCC 14067, AJ12418 (FERM
BP-2205)
*Brevibacterium immariophilum* ATCC 14068
*Brevibacterium lactofermentum (Corynebacterium gluta-*
*micum)* ATCC 13869
*Brevibacterium roseum* ATCC 13825
*Brevibacterium saccharolyticum* ATCC 14066
*Brevibacterium thiogenitalis* ATCC 19240
*Corynebacterium ammoniagenes (Corynebacterium sta-*
*tionis)* ATCC 6871, ATCC 6872
*Brevibacterium album* ATCC 15111
*Brevibacterium cerinum* ATCC 15112
*Microbacterium ammoniaphilum* ATCC 15354

The *Corynebacterium* bacteria include bacteria that had
previously been classified into the genus *Brevibacterium*,
but are presently united into the genus *Corynebacterium*
(Int. J. Syst. Bacteriol., 41, 255 (1991)). Moreover, *Coryne-*
*bacterium stationis* includes bacteria that had previously
been classified as *Corynebacterium ammoniagenes*, but are
presently re-classified into *Corynebacterium stationis* on the
basis of nucleotide sequence analysis of 16S rRNA etc. (Int.
J. Syst. Evol. Microbiol., 60, 874-879 (2010)).

These strains are available from, for example, the Ameri-
can Type Culture Collection (Address: P.O. Box 1549,
Manassas, VA 20108, United States of America). That is,
registration numbers are assigned to the respective strains,
and the strains can be ordered by using these registration
numbers (refer to www.atcc.org). The registration numbers
of the strains are listed in the catalogue of the American Type
Culture Collection. These strains can also be obtained from,
for example, the depositories at which the strains were
deposited.

In particular, the *Corynebacterium glutamicum (C. glu-*
*tamicum)* AJ12036 strain (FERM BP-734), which was iso-
lated as a streptomycin (Sm) resistant mutant strain from a
wild-type strain *C. glutamicum* ATCC 13869, is predicted to
have a mutation in a gene responsible for a function involved
in secretion of proteins, and shows an extremely high
secretory production ability for proteins as high as about 2
to 3 times in terms of accumulation amount of proteins under
optimum culture conditions, compared with the parent strain
(wild-type strain), and therefore it is preferred as a host
bacterium (WO 02/081694). The AJ12036 strain was origi-
nally deposited at the Fermentation Research Institute,
Agency of Industrial Science and Technology (currently, independent administrative agency, National Institute of
Technology and Evaluation, International Patent Organism
Depositary, #120, 2-5-8 Kazusakamatari, Kisarazu-shi,
Chiba-ken, 292-0818, Japan) on Mar. 26, 1984, as an
international deposit, and assigned an accession number of
FERM BP-734.

*Corynebacterium thermoaminogenes* AJ12340 (FERM
BP-1539) was originally deposited at the Fermentation
Research Institute, Agency of Industrial Science and Tech-
nology (currently, independent administrative agency,
National Institute of Technology and Evaluation, Interna-
tional Patent Organism Depositary, #120, 2-5-8 Kazusaka-
matari, Kisarazu-shi, Chiba-ken, 292-0818, Japan) on Mar.
13, 1987, as an international deposit, and assigned an
accession number of FERM BP-1539. *Brevibacterium fla-*
*vum* AJ12418 (FERM BP-2205) was originally deposited at
the Fermentation Research Institute, Agency of Industrial
Science and Technology (currently, independent administra-
tive agency, National Institute of Technology and Evalua-
tion, International Patent Organism Depositary, #120, 2-5-8
Kazusakamatari, Kisarazu-shi, Chiba-ken, 292-0818, Japan)
on Dec. 24, 1988, as an international deposit, and assigned
an accession number of FERM BP-2205.

Moreover, a strain having an enhanced ability to produce
a protein by secretory production may be selected from such
a coryneform bacterium as mentioned above as a parent
strain by using a mutagenesis method or a genetic recom-
bination method, and used as a host. For example, after a
parent strain is treated with ultraviolet irradiation or a
chemical mutation agent such as N-methyl-N'-nitrosogua-
nidine, a strain having an enhanced ability to produce a
protein by secretory production can be selected.

Furthermore, if a strain obtained by modifying such a
strain as mentioned above so that it does not produce a cell
surface layer protein is used as a host, purification of the
heterologous protein secreted in the medium or on the cell
surface layer becomes easy, and therefore it is particularly
preferred. Such modification can be carried out by introduc-
ing a mutation into the coding region of the cell surface layer
protein or an expression control region thereof, on the
chromosome by mutagenesis or genetic recombination.
Examples of coryneform bacterium modified so that it does
not produce a cell surface layer protein include the *C.*
*glutamicum* YDK010 strain (WO 2004/029254), which is a
cell surface layer protein PS2 deficient strain of the *C.*
*glutamicum* AJ12036 strain (FERM BP-734).

A coryneform bacterium having an ability of secretory
production of a heterologous protein can be obtained by
introducing the genetic construct used for methods of the
present disclosure into such a coryneform bacterium as
described above so as to make the bacterium harbor the
genetic construct. That is, the bacterium of the present
disclosure may be, for example, a modified strain derived
from such a coryneform bacterium as described above. The
bacterium of the present disclosure may be, specifically, for
example, a modified strain derived from *C. glutamicum*
AJ12036 (FERM BP-734) or a modified strain derived from
*C. glutamicum* ATCC 13869. A modified strain derived from
*C. glutamicum* AJ12036 (FERM BP-734) also falls within a
modified strain derived from *C. glutamicum* ATCC 13869.
The genetic construct used for methods of the present
disclosure and methods for introduction of the same will be
described later.

<1-2> Specific Feature

The bacterium of the present disclosure has been modified
to have the specific feature. By modifying a coryneform
bacterium to have the specific feature, an ability of the bacterium to produce a heterologous protein by secretory production can be improved, that is, secretory production of a heterologous protein by the bacterium can be increased.

The bacterium of the present disclosure can be obtained by modifying a coryneform bacterium having an ability of secretory production of a heterologous protein to have the specific feature. The bacterium of the present disclosure can also be obtained by modifying a coryneform bacterium to have the specific feature, and then imparting an ability of secretory production of a heterologous protein thereto. In the present disclosure, modifications for constructing the bacterium of the present disclosure can be performed in any order. A strain to be used for constructing the bacterium of the present disclosure and before being modified so as to have the specific feature may or may not be able to produce a heterologous protein, on the assumption that the strain has the genetic construct for secretory expression of the heterologous protein. That is, the bacterium of the present disclosure may also be, for example, a bacterium that has acquired an ability of secretory production of a heterologous protein due to being modified so as to have the specific feature. Specifically, for example, the bacterium of the present disclosure may also be a bacterium obtained from a strain that is not able to produce a heterologous protein by secretory production even when it has the genetic construct for secretory expression of the heterologous protein before it is modified so as to have the specific feature, which came to be able to produce the heterologous protein by secretory production due to being modified to have the specific feature.

The phrase "specific feature" refers to a combination of two or more features selected from (A), (B), and (C), shown below:

(A) the activity of a RegX3 protein is reduced;

(B) the activity of an HrrSA system is reduced;

(C) the activity of an HrcA protein is reduced.

In the features (A) to (C), each activity is reduced as compared with a non-modified strain.

The specific feature may be specifically a combination of the feature (A) and (B), a combination of the feature (A) and (C), a combination of the feature (B) and (C), or a combination of the feature (A), (B), and (C). That is, the bacterium of the present disclosure may have a combination of the feature (A) and (B), a combination of the feature (A) and (C), or a combination of the feature (B) and (C). The bacterium of the present disclosure may also have a combination of the feature (A), (B), and (C). In other words, the bacterium of the present disclosure may have a combination of the feature (A) and (B), and may further have the feature (C). The bacterium of the present disclosure may also have a combination of the feature (A) and (C), and may further have the feature (B). The bacterium of the present disclosure may also have a combination of the feature (B) and (C), and may further have the feature (A).

<1-2-1> Decrease in the Activity of RegX3 Protein

Hereinafter, the RegX3 protein and the regX3 gene encoding it will be explained. The RegX3 protein is a response regulator of the SenX3-RegX3 system. The SenX3-RegX3 system is one of two-component regulatory systems, and induces a response against an environmental stimulus. The SenX3-RegX3 system is formed of a sensor kinase SenX3 encoded by a senX3 gene and a response regulator RegX3 encoded by a regX3 gene.

The nucleotide sequences of regX3 genes possessed by coryneform bacteria and the amino acid sequences of RegX3 proteins encoded by them can be obtained from, for example, public databases such as NCBI (National Center for Biotechnology Information). The nucleotide sequence of the regX3 gene of *C. glutamicum* ATCC 13869 is shown as SEQ ID NO: 41, and the amino acid sequence of the RegX3 protein encoded by this gene is shown as SEQ ID NO: 42. That is, the regX3 gene may be, for example, a gene having the nucleotide sequence shown as SEQ ID NO: 41. Also, the RegX3 protein may be, for example, a protein having the amino acid sequence shown as SEQ ID NO: 42. The expression "having a (nucleotide or amino acid) sequence" means "including the (nucleotide or amino acid) sequence" unless otherwise stated, and also includes cases of "formed of the (nucleotide or amino acid) sequence".

The regX3 gene may be a variant of any of the regX3 genes exemplified above (such as a gene having the nucleotide sequence shown as SEQ ID NO: 41), so long as the original function thereof is maintained. Similarly, the RegX3 protein may be a variant of any of the RegX3 proteins exemplified above (such as a protein having the amino acid sequence shown as SEQ ID NO: 42), so long as the original function thereof is maintained. Such a variant is also referred to as a "conservative variant". In the present disclosure, the term "regX3 gene" includes not only the regX3 genes exemplified above, but also includes conservative variants thereof. Similarly, the term "RegX3 protein" includes not only the RegX3 proteins exemplified above, but also includes conservative variants thereof. Examples of the conservative variants include, for example, homologues and artificially modified versions of the regX3 genes and RegX3 proteins exemplified above.

The expression "the original function is maintained" means that a variant of a gene or protein has a function (such as activity or property) corresponding to the function (such as activity or property) of the original gene or protein. That is, the expression "the original function is maintained" used for the regX3 gene may mean that a variant of the gene encodes a protein that maintains the original function (i.e., a RegX3 protein). Furthermore, the expression "the original function is maintained" used for the RegX3 protein may mean that a variant of the protein has a function as a RegX3 protein (such as a function of a protein having the amino acid sequence shown as SEQ ID NO: 42). Furthermore, the expression "the original function is maintained" used for the RegX3 protein may also mean that a variant of the protein has a function as a response regulator of the SenX3-RegX3 system. That is, the term "function as a RegX3 protein" may specifically refer to a function as a response regulator of the SenX3-RegX3 system. The term "function as a response regulator of the SenX3-RegX3 system" may specifically refer to a function of inducing a response against an environmental stimulus in combination with a sensor kinase SenX3 protein. The term "function as a response regulator of the SenX3-RegX3 system" may more specifically refer to a function of being activated via transfer of phosphate group from the SenX3 protein that sensed an environmental stimulus to be autophosphorylated, and regulating (e.g., inducing or repressing) the expression of genes. Examples of the SenX3 protein include the SenX3 protein inherently possessed by the bacterium of the present disclosure. The nucleotide sequence of the senX3 gene of *C. glutamicum* ATCC 13869 is shown as SEQ ID NO: 39, and the amino acid sequence of the SenX3 protein encoded by this gene is shown as SEQ ID NO: 40. Examples of the genes of which the expression is induced by the SenX3-RegX3 system include genes responding to depletion of inorganic phosphate (such as pstSCAB, ugpAEBC, phoC, and ushA genes) and genes involved in biosynthesis of $NAD^+$ (such as ndnR-nadA-nadC-nadS operon genes).

Whether or not a variant of the RegX3 protein has a function as a response regulator of the SenX3-RegX3 system can be confirmed by, for example, reducing the activity of the variant in a coryneform bacterium, and confirming whether or not the expression of genes of which the expression is induced by the SenX3-RegX3 system is reduced. Whether or not a variant of the RegX3 protein has a function as a response regulator of the SenX3-RegX3 system can also be confirmed by, for example, introducing a gene encoding the variant into a regX3-gene-deletion strain of a coryneform bacterium, and confirming whether or not the expression of genes of which the expression is induced by the SenX3-RegX3 system is increased. As the regX3-gene-deletion strain of a coryneform bacterium, for example, a regX3-gene-deletion strain of *C. glutamicum* YDK010 can be used.

Hereinafter, examples of the conservative variants will be explained.

Homologues of the regX3 genes and homologues of the RegX3 proteins can be easily obtained from public databases by, for example, BLAST search or FASTA search using any of the nucleotide sequences of the regX3 genes exemplified above or any of the amino acid sequences of the RegX3 proteins exemplified above as a query sequence. Furthermore, homologues of the regX3 genes can be obtained by, for example, PCR using a chromosome of coryneform bacteria as the template, and oligonucleotides prepared on the basis of any of the nucleotide sequences of these known regX3 genes as primers.

The regX3 gene may be a gene encoding a protein having any of the amino acid sequences of the RegX3 proteins exemplified above (such as the amino acid sequence shown as SEQ ID NO: 42), but which includes substitution, deletion, insertion, and/or addition of one or several amino acid residues at one or several positions, so long as the original function thereof is maintained. Although the number meant by the term "one or several" mentioned above may differ depending on the positions of amino acid residues in the three-dimensional structure of the protein or the types of amino acid residues, specifically, it is, for example, 1 to 50, 1 to 40, 1 to 30, 1 to 20, 1 to 10, 1 to 5, or 1 to 3.

The aforementioned substitution, deletion, insertion, and/or addition of one or several amino acid residues is a conservative mutation that maintains the normal function of the protein. Typical examples of the conservative mutation are conservative substitutions. The conservative substitution is a mutation wherein substitution takes place mutually among Phe, Trp, and Tyr, if the substitution site is an aromatic amino acid; among Leu, Ile, and Val, if it is a hydrophobic amino acid; between Gln and Asn, if it is a polar amino acid; among Lys, Arg, and His, if it is a basic amino acid; between Asp and Glu, if it is an acidic amino acid; and between Ser and Thr, if it is an amino acid having a hydroxyl group. Examples of substitutions considered as conservative substitutions include, specifically, substitution of Ser or Thr for Ala, substitution of Gln, His, or Lys for Arg, substitution of Glu, Gln, Lys, His, or Asp for Asn, substitution of Asn, Glu, or Gln for Asp, substitution of Ser or Ala for Cys, substitution of Asn, Glu, Lys, His, Asp, or Arg for Gln, substitution of Gly, Asn, Gln, Lys, or Asp for Glu, substitution of Pro for Gly, substitution of Asn, Lys, Gln, Arg, or Tyr for His, substitution of Leu, Met, Val, or Phe for Ile, substitution of Ile, Met, Val, or Phe for Leu, substitution of Asn, Glu, Gln, His, or Arg for Lys, substitution of Ile, Leu, Val, or Phe for Met, substitution of Trp, Tyr, Met, Ile, or Leu for Phe, substitution of Thr or Ala for Ser, substitution of Ser or Ala for Thr, substitution of Phe or Tyr for Trp, substitution of His, Phe, or Trp for Tyr, and substitution of Met, Ile, or Leu for Val. Furthermore, such substitution, deletion, insertion, or addition of amino acid residues as mentioned above includes a naturally occurring mutation due to an individual difference, or a difference of species of the bacterium from which the gene is derived (mutant or variant).

The regX3 gene may also be a gene encoding a protein having an amino acid sequence showing an identity of, for example, 80% or more, 90% or more, 95% or more, 97% or more, or 99% or more, to the total amino acid sequence of any of the amino acid sequences of the RegX3 proteins exemplified above (such as the amino acid sequence shown as SEQ ID NO: 42), so long as the original function thereof is maintained.

The regX3 gene may also be DNA that is able to hybridize under stringent conditions with a complementary sequence of any of the nucleotide sequences of the regX3 genes exemplified above (such as the nucleotide sequence shown as SEQ ID NO: 41), or with a probe that can be prepared from the complementary sequence, so long as the original function thereof is maintained. The term "stringent conditions" refers to conditions under which a so-called specific hybrid is formed, and a non-specific hybrid is not formed. Examples of the stringent conditions include those under which highly identical DNAs hybridize to each other, for example, DNAs not less than 80% identical, not less than 90% identical, not less than 95% identical, not less than 97% identical, or not less than 99% identical, hybridize to each other, and DNAs less identical than the above do not hybridize to each other, or conditions of washing of typical Southern hybridization, i.e., conditions of washing once, or 2 or 3 times, at a salt concentration and temperature corresponding to 1×SSC, 0.1% SDS at 60° C., 0.1×SSC, 0.1% SDS at 60° C., or 0.1×SSC, 0.1% SDS at 68° C.

The probe may be, for example, a part of a sequence that is complementary to the gene as described above. Such a probe can be prepared by PCR using oligonucleotides prepared on the basis of the nucleotide sequences of known genes as primers and a DNA fragment containing any of these nucleotide sequences as a template. As the probe, for example, a DNA fragment having a length of about 300 bp can be used. In such a case, the washing conditions of the hybridization may be, for example, 50° C., 2×SSC and 0.1% SDS.

Furthermore, the regX3 gene may be a gene having a nucleotide sequence corresponding to any of the nucleotide sequences of the regX3 genes exemplified above or conservative variants thereof in which any codon(s) is/are replaced with respective equivalent codon(s).

The term "identity" between amino acid sequences means an identity between the amino acid sequences calculated by blastp with default scoring parameters (i.e., Matrix, BLOSUM62; Gap Costs, Existence=11, Extension=1; Compositional Adjustments, Conditional compositional score matrix adjustment), unless otherwise stated. The term "identity" between nucleotide sequences means an identity between the nucleotide sequences calculated by blastn with default scoring parameters (i.e., Match/Mismatch Scores=1,−2; Gap Costs=Linear), unless otherwise stated.

The aforementioned descriptions concerning variants of the genes and proteins can also be applied similarly to any proteins such as SenX3 protein, HrrSA proteins, HrcA protein, PhoRS proteins, cell surface layer protein, Tat secretion system, and heterologous proteins to be produced by secretory production in the present disclosure, and genes encoding them.

The phrase "the activity of RegX3 protein is reduced" may mean that the function of the response regulator of the SenX3-RegX3 system is reduced. Hence, a reduction in the activity of RegX3 protein can be measured by, specifically, for example, using a reduction in the expression of genes of which the expression is induced by the SenX3-RegX3 system as an index. Also, the phrase "the activity of RegX3 protein is reduced" may particularly mean that the number of molecules of the RegX3 protein per cell is reduced. Methods for reducing the activity of a protein such as the RegX3 protein will be explained later. The activity of RegX3 protein can be reduced by, for example, reducing the expression of a gene encoding the protein (regX3 gene), or by disrupting the regX3 gene. Furthermore, in a two-component regulatory system, when a sensor kinase senses a stimulus, a specific histidine residue thereof is autophosphorylated, and a signal is transduced via transfer of the phosphate group to a specific aspartic acid residue of a response regulator. Hence, the activity of RegX3 protein can also be reduced by, for example, replacing or deleting the aspartic acid residue of the RegX3 protein, to which the phosphate group is transferred from the autophosphorylated histidine residue of the SenX3 protein. This aspartic acid residue is the aspartic acid residue at position 52 (D52) of the RegX3 protein. The term "D52 of the RegX3 protein" specifically means the aspartic acid residue corresponding to D52 of SEQ ID NO: 42. The descriptions concerning the position of the "amino acid residue at position X of the wild-type PhoS protein" described later can be applied similarly to the position of the "D52 of the RegX3 protein" in any chosen RegX3 protein. This aspartic acid residue may be replaced or deleted solely or in combination with a surrounding region. That is, for example, only this aspartic acid residue may be replaced or deleted, or a region including this aspartic acid residue may be replaced or deleted.

The RegX3 protein can be essential depending on the type of the coryneform bacterium. For example, it has been indicated that the RegX3 protein is essential in *C. glutamicum* ATCC 13032. When the RegX3 protein is essential in the bacterium of the present disclosure, the activity of the RegX3 protein can remain as required. For example, the activity of the RegX3 protein inherently possessed by the bacterium of the present disclosure may partially remain. Also, for example, the activity of the RegX3 protein inherently possessed by the bacterium of the present disclosure may be completely eliminated, and the activity of the RegX3 protein may be separately imparted at a level lower than that of the RegX3 protein inherently possessed by the bacterium of the present disclosure. The activity of RegX3 protein may remain at a level of, for example, 1% or more, 5% or more, 10% or more, 15% or more, 20% or more, 30% or more, or 50% or more, of that of a non-modified strain. Similarly, the expression amount of the regX3 gene may remain at a level of, for example, 1% or more, 5% or more, 10% or more, 15% or more, 20% or more, 30% or more, or 50% or more, of that of a non-modified strain. Similarly, the amount of the RegX3 protein (such as the number of molecules of the protein per cell) remain at a level of, for example, 1% or more, 5% or more, 10% or more, 15% or more, 20% or more, 30% or more, or 50% or more, of that of a non-modified strain.

<1-2-2> Decrease in the Activity of HrrSA System

Hereinafter, the HrrSA system and genes encoding it will be explained. The HrrSA system is one of two-component regulatory systems, and induces a response against an environmental stimulus such as the presence of haem. The HrrSA system is formed of a sensor kinase HrrS encoded by a hrrS gene and a response regulator HrrA encoded by a hrrA gene. The hrrS gene and the hrrA gene are also collectively referred to as "hrrSA genes". The HrrS (HrrS protein) and the HrrA (HrrA protein) are also collectively referred to as "HrrSA proteins".

The nucleotide sequences of hrrSA genes possessed by coryneform bacteria and the amino acid sequences of HrrSA proteins encoded by them can be obtained from, for example, public databases such as NCBI (National Center for Biotechnology Information). The nucleotide sequence of the hrrS gene of *C. glutamicum* ATCC 13869 is shown as SEQ ID NO: 43, and the amino acid sequence of the HrrS protein encoded by this gene is shown as SEQ ID NO: 44. The nucleotide sequence of the hrrA gene of *C. glutamicum* ATCC 13869 is shown as SEQ ID NO: 45, and the amino acid sequence of the HrrA protein encoded by this gene is shown as SEQ ID NO: 46. That is, the hrrSA genes may be, for example, genes having the nucleotide sequences shown as SEQ ID NOS: 43 and 45, respectively. Also, the HrrSA proteins may be, for example, proteins having the amino acid sequences shown as SEQ ID NOS: 44 and 46, respectively.

The hrrSA genes each may be a variant of any of the hrrSA genes exemplified above (such as a gene having the nucleotide sequence shown as SEQ ID NO: 43 or 45), so long as the original function thereof is maintained. Similarly, the HrrSA proteins each may be a variant of any of the HrrSA proteins exemplified above (such as a protein having the amino acid sequence shown as SEQ ID NO: 44 or 46), so long as the original function thereof is maintained. That is, the term "hrrSA genes" includes not only the hrrSA genes exemplified above, but also includes conservative variants thereof. Similarly, the term "HrrSA proteins" includes not only the HrrSA proteins exemplified above, but also includes conservative variants thereof. The aforementioned descriptions concerning conservative variants of the regX3 gene and the RegX3 protein can also be applied similarly to the hrrSA genes and the HrrSA proteins. For example, the hrrSA genes may each be a gene encoding a protein having any of the aforementioned amino acid sequences, but which includes substitution, deletion, insertion, and/or addition of one or several amino acid residues at one or several positions, so long as the original function thereof is maintained.

The expression "the original function is maintained" used for each of the hrrSA genes may mean that a variant of the gene encodes a protein that maintains the original function (i.e., each of HrrSA proteins). Furthermore, the expression "the original function is maintained" used for each of the HrrSA proteins may mean that a variant of the protein has a function as each of HrrSA proteins (such as a function of a protein having the amino acid sequence shown as SEQ ID NO: 44 or 46). Furthermore, the expression "the original function is maintained" used for the HrrS protein may also mean that a variant of the protein has a function as a sensor kinase of the HrrSA system. Furthermore, the expression "the original function is maintained" used for the HrrA protein may also mean that a variant of the protein has a function as a response regulator of the HrrSA system. That is, the term "function as HrrSA proteins" may specifically refer to a function as a sensor kinase of the HrrSA system and a function as a response regulator of the HrrSA system, respectively. The term "function as a sensor kinase of the HrrSA system" may specifically refer to a function of inducing a response against an environmental stimulus in combination with a response regulator HrrA protein. The term "function as a sensor kinase of the HrrSA system" may more specifically refer to a function of sensing an environmental stimulus to be autophosphorylated, and activating the HrrA protein via transfer of phosphate group. The term "function as a response regulator of the HrrSA system" may specifically refer to a function of inducing a response against an environmental stimulus in combination with a sensor kinase HrrS protein. The term "function as a response regulator of the HrrSA system" may more specifically refer to a function of being activated via transfer of phosphate group from the HrrS protein that sensed an environmental stimulus to be autophosphorylated, and regulating (e.g., inducing or repressing) the expression of genes. Examples of the genes of which the expression is induced by the HrrSA system include genes involved in degradation of haem (such as hmuO gene) and genes encoding haem-containing proteins in the respiratory chain (such as ctaE-qcrCAB operon genes and ctaD gene). Examples of the genes of which the expression is repressed by the HrrSA system include genes involved in biosynthesis of haem (such as hemE-hemY-hemL-cg0519-ccsX-ccdA-resB-resC operon genes, hemA-hemC operon genes, and hemH gene).

Whether or not a variant of the HrrSA proteins has a function as a sensor kinase or a response regulator of the HrrSA system can be confirmed by, for example, reducing the activity of the variant in a coryneform bacterium, and confirming whether or not the expression of genes of which the expression is induced or repressed by the HrrSA system is reduced or increased in the presence of haem. Whether or not a variant of the HrrS protein has a function as a sensor kinase of the HrrSA system can also be confirmed by, for example, introducing a gene encoding the variant into an hrrS-gene-deletion strain of a coryneform bacterium, and confirming whether or not the expression of genes of which the expression is induced or repressed by the HrrSA system is increased or reduced in the presence of haem. Whether or not a variant of the HrrA protein has a function as a response regulator of the HrrSA system can also be confirmed by, for example, introducing a gene encoding the variant into an hrrA-gene-deletion strain of a coryneform bacterium, and confirming whether or not the expression of genes of which the expression is induced or repressed by the HrrSA system is increased or reduced in the presence of haem. As the hrrS-gene- or hrrA-gene-deletion strain of a coryneform bacterium, for example, an hrrS-gene- or hrrA-gene-deletion strain of C. glutamicum YDK010 or a hrrS-gene- or hrrA-gene-deletion strain of C. glutamicum ATCC 13032 can be used.

The phrase "the activity of HrrSA system is reduced" may mean that the degree of a response against an environmental stimulus induced via the HrrSA system is reduced. The activity of HrrSA system can be reduced by, for example, reducing the activity of HrrS protein and/or HrrA protein (i.e., either one or both of HrrS protein and HrrA protein). That is, the phrase "the activity of HrrSA system is reduced" may also mean that the activity of the HrrS protein and/or the HrrA protein is reduced. In the present disclosure, for example, at least the activity of the HrrA protein may be reduced. The phrase "the activity of HrrS protein is reduced" may mean that the function of the sensor kinase of the HrrSA system is reduced. The phrase "the activity of HrrA protein is reduced" may mean that the function of the response regulator of the HrrSA system is reduced. Hence, a reduction in the activity of HrrSA system, HrrS protein, or HrrA protein can be measured by, specifically, for example, using a reduction or increase in the expression of genes of which the expression is induced or repressed by the HrrSA system in the presence of haem as an index. Also, the phrase "the activity of HrrSA system is reduced" may particularly mean that the number of molecules of the HrrSA system per cell is reduced. Similarly, the phrase "the activity of HrrS protein and/or HrrA protein is reduced" may particularly mean that the number of molecules of the HrrS protein and/or HrrA protein per cell is reduced. Methods for reducing the activity of a protein such as the HrrSA proteins will be explained later. The activity of HrrSA proteins can be reduced by, for example, reducing the expression of genes encoding the proteins (hrrSA genes), or by disrupting the hrrSA genes. Furthermore, in a two-component regulatory system, when a sensor kinase senses a stimulus, a specific histidine residue thereof is autophosphorylated, and a signal is transduced via transfer of the phosphate group to a specific aspartic acid residue of a response regulator. Hence, the activity of HrrSA system, specifically the activity of HrrS protein, can also be reduced by, for example, replacing or deleting the histidine residue to be autophosphorylated of the HrrS protein. Furthermore, the activity of HrrSA system, the activity of HrrA protein, can also be reduced by, for example, replacing or deleting the aspartic acid residue of the HrrA protein, to which the phosphate group is transferred from the autophosphorylated histidine residue of the HrrS protein. This histidine residue is the histidine residue at position 217 (H217) of the HrrS protein. The term "H217 of the HrrS protein" specifically means the histidine residue corresponding to H217 of SEQ ID NO: 44. This aspartic acid residue is the aspartic acid residue at position 54 (D54) of the HrrA protein. The term "D54 of the HrrA protein" specifically means the aspartic acid residue corresponding to D54 of SEQ ID NO: 46. The descriptions concerning the position of the "amino acid residue at position X of the wild-type PhoS protein" described later can be applied similarly to the position of the "H217 of the HrrS protein" or "D54 of the HrrA protein" in any chosen HrrSA proteins. This histidine or aspartic acid residue may be replaced or deleted solely or in combination with a surrounding region. That is, for example, only this histidine or aspartic acid residue may be replaced or deleted, or a region including this histidine or aspartic acid residue may be replaced or deleted.

<1-2-3> Decrease in the Activity of HrcA Protein

Hereinafter, the HrcA protein and the hrcA gene encoding it will be explained. The HrcA protein is a transcription repressor of heat-shock proteins.

The nucleotide sequences of hrcA genes possessed by coryneform bacteria and the amino acid sequences of HrcA proteins encoded by them can be obtained from, for example, public databases such as NCBI (National Center for Biotechnology Information). The nucleotide sequence of the hrcA gene of C. glutamicum ATCC 13869 is shown as SEQ ID NO: 47, and the amino acid sequence of the HrcA protein encoded by this gene is shown as SEQ ID NO: 48. That is, the hrcA gene may be, for example, a gene having the nucleotide sequence shown as SEQ ID NO: 47. Also, the HrcA protein may be, for example, a protein having the amino acid sequence shown as SEQ ID NO: 48.

The hrcA gene may be a variant of any of the hrcA genes exemplified above (such as a gene having the nucleotide sequence shown as SEQ ID NO: 47), so long as the original function thereof is maintained. Similarly, the HrcA protein may be a variant of any of the HrcA proteins exemplified above (such as a protein having the amino acid sequence shown as SEQ ID NO: 48), so long as the original function thereof is maintained. That is, the term "hrcA gene" includes not only the hrcA genes exemplified above, but also includes conservative variants thereof. Similarly, the term "HrcA protein" includes not only the HrcA proteins exemplified above, but also includes conservative variants thereof. The aforementioned descriptions concerning conservative variants of the regX3 gene and the RegX3 protein can also be applied similarly to the hrcA gene and the HrcA protein. For example, the hrcA gene may be a gene encoding a protein having any of the aforementioned amino acid sequences, but which includes substitution, deletion, insertion, and/or addition of one or several amino acid residues at one or several positions, so long as the original function thereof is maintained.

The expression "the original function is maintained" used for the hrcA gene may mean that a variant of the gene encodes a protein that maintains the original function (i.e., an HrcA protein). Furthermore, the expression "the original function is maintained" used for the HrcA protein may mean that a variant of the protein has a function as an HrcA protein (such as a function of a protein having the amino acid sequence shown as SEQ ID NO: 48). Furthermore, the expression "the original function is maintained" used for the HrcA protein may also mean that a variant of the protein has a function as a transcription repressor of heat-shock proteins. That is, the term "function as an HrcA protein" may specifically refer to a function as a transcription repressor of heat-shock proteins. The term "function as transcription repressor of heat-shock proteins" may specifically refer to a function of repressing the expression of genes encoding heat-shock proteins (heat-shock genes). Examples of the heat-shock genes of which the expression is repressed by the HrcA protein include groEL gene, such as groEL1 gene and groEL2 gene, and groES gene.

Whether or not a variant of the HrcA protein has a function as a transcription repressor of heat-shock proteins can be confirmed by, for example, reducing the activity of the variant in a coryneform bacterium, and confirming whether or not the transcription (expression) of heat-shock genes such as groEL gene and groES gene is increased. Whether or not a variant of the HrcA protein has a function as a transcription repressor of heat-shock proteins can also be confirmed by, for example, introducing a gene encoding the variant into an hrcA-gene-deletion strain of a coryneform bacterium, and confirming whether or not the transcription (expression) of heat-shock genes such as groEL gene and groES gene is reduced. As the hrcA-gene-deletion strain of a coryneform bacterium, for example, an hrcA-gene-deletion strain of C. glutamicum YDK010 can be used.

The phrase "the activity of HrcA protein is reduced" may mean that the function of the transcription repressor of heat-shock proteins is reduced. Hence, a reduction in the activity of HrcA protein can be measured by, specifically, for example, using an increase in the transcription (expression) of heat-shock genes such as groEL gene and groES gene as an index. Also, the phrase "the activity of HrcA protein is reduced" may particularly mean that the number of molecules of the HrcA protein per cell is reduced. Methods for reducing the activity of a protein such as the HrcA protein will be explained later. The activity of HrcA protein can be reduced by, for example, reducing the expression of a gene encoding the protein (hrcA gene), or by disrupting the hrcA gene.

<1-3> Other Characteristics

The bacterium of the present disclosure may have desired characteristics, so long as it can produce a heterologous protein by secretory production. For example, the activity of a cell surface layer protein may have been reduced in the bacterium of the present disclosure (WO 2013/065869, WO 2013/065772, WO 2013/118544, and WO 2013/062029). For example, the bacterium of the present disclosure may have been modified so that the activity of a penicillin-binding protein is reduced (WO 2013/065869). For example, the bacterium of the present disclosure may have been modified so that the expression of a gene encoding a metallopeptidase is increased (WO 2013/065772). For example, the bacterium of the present disclosure may have been modified to have a mutant ribosomal protein S1 gene (mutant rpsA gene) (WO 2013/118544). For example, the bacterium of the present disclosure may have been modified to have a mutant phoS gene (WO 2016/171224). For example, the Tat secretion system may be enhanced in the bacterium of the present disclosure. These characteristics or modifications can be used solely or in any appropriate combination.

<1-3-1> Introduction of Mutant phoS Gene

The bacterium of the present disclosure may have been modified to harbor a mutant phoS gene. The expression "to harbor a mutant phoS gene" is also referred to as "to have a mutant phoS gene" or "to have a mutation in a phoS gene". In addition, the expression "to harbor a mutant phoS gene" is also referred to as "to have a mutant PhoS protein" or "to have a mutation in a PhoS protein".

Hereinafter, the phoS gene and the PhoS protein will be explained. The phoS gene is a gene encoding a PhoS protein, which is a sensor kinase of the PhoRS system. The PhoRS system is one of two-component regulatory systems, and induces a response against phosphate depletion. The PhoRS system is formed of a sensor kinase PhoS encoded by a phoS gene and a response regulator PhoR encoded by a phoR gene.

In the present disclosure, a PhoS protein having the "specific mutation" is also referred to as "mutant PhoS protein", and a gene encoding it is also referred to as "mutant phoS gene". The mutant phoS gene is, in other words, a phoS gene having the "specific mutation". Furthermore, in the present disclosure, a PhoS protein not having the "specific mutation" is also referred to as "wild-type PhoS protein", and a gene encoding it is also referred to as "wild-type phoS gene". The wild-type phoS gene is, in other words, a phoS gene not having the "specific mutation". The term "wild-type" referred to herein is used for convenience to distinguish "wild-type" ones from "mutant" ones, and "wild-type" ones are not limited to those obtained as natural substances, so long as those do not have the "specific mutation". The "specific mutation" will be described later.

Examples of the wild-type phoS gene include, for example, phoS genes of coryneform bacteria. Specific examples of the phoS genes of coryneform bacteria include, for example, the phoS genes of C. glutamicum YDK010, C. glutamicum ATCC 13032, C. glutamicum ATCC 14067, C. callunae, C. crenatum, and C. efficiens. The nucleotide sequence of the phoS gene of C. glutamicum YDK010 is shown as SEQ ID NO: 1. The amino acid sequences of the wild-type PhoS proteins encoded by these phoS genes are shown as SEQ ID NOS: 2 to 7, respectively.

The wild-type phoS gene may be a variant of any of the wild-type phoS genes exemplified above, so long as it does not have the "specific mutation" and the original function thereof is maintained. Similarly, the wild-type PhoS protein may be a variant of any of the wild-type PhoS proteins exemplified above, so long as it does not have the "specific mutation" and the original function thereof is maintained. That is, the term "wild-type phoS gene" includes not only the wild-type phoS genes exemplified above, but also includes conservative variants thereof that do not have the "specific mutation". Similarly, the term "wild-type PhoS protein" includes not only the wild-type PhoS proteins exemplified above, but also includes conservative variants thereof that do not have the "specific mutation". The afore-mentioned descriptions concerning conservative variants of the RegX3 protein and the regX3 gene can be applied similarly to variants of the wild-type PhoS protein and the wild-type phoS gene. For example, the wild-type phoS gene may also be a gene encoding a protein having any of the aforementioned amino acid sequences, but which includes substitution, deletion, insertion, and/or addition of one or several amino acid residues at one or several positions, so long as it does not have the "specific mutation" and the original function thereof is maintained.

The expression "the original function is maintained" used for the wild-type PhoS may mean that a variant of the protein has a function as a PhoS protein (such as a function of a protein formed of any of the amino acid sequences shown as SEQ ID NOS: 2 to 7). Furthermore, the expression "the original function is maintained" used for the wild-type PhoS protein may also mean that a variant of the protein has a function as a sensor kinase of the PhoRS system. That is, the term "function as a PhoS protein" may specifically refer to a function as a sensor kinase of the PhoRS system. The term "function as a sensor kinase of the PhoRS system" may specifically refer to a function of inducing a response against phosphate depletion in the environment in combination with a response regulator PhoR protein. The term "function as a sensor kinase of the PhoRS system" may more specifically refer to a function of sensing phosphate depletion in the environment to be autophosphorylated, and activating the PhoR protein via transfer of phosphate group.

Whether or not a variant of the PhoS protein has a function as a sensor kinase of the PhoRS system can be confirmed by, for example, introducing a gene encoding the variant into a phoS-gene-deletion strain of a coryneform bacterium, and confirming whether or not responsiveness against phosphate depletion is complemented. Complementation of responsiveness against phosphate depletion can be detected, for example, as improvement of growth under phosphate depletion conditions, or as induction of the expression of genes of which the expression is known to be induced under phosphate depletion conditions (J. Bacteriol., 188, 724-732 (2006)). As the phoS-gene-deletion strain of a coryneform bacterium, for example, a phoS-gene-deletion strain of *C. glutamicum* YDK010 or a phoS-gene-deletion strain of *C. glutamicum* ATCC 13032 can be used.

A histidine residue that is autophosphorylated may be conserved in the wild-type PhoS protein. That is, a conservative mutation may occur at an amino acid residue other than the histidine residue that is autophosphorylated. The term "histidine residue that is autophosphorylated" refers to a histidine residue at position 276 of the wild-type PhoS protein. Furthermore, for example, the wild-type PhoS protein may have a conservative sequence of the wild-type PhoS proteins exemplified above. That is, a conservative mutation may occur at, for example, an amino acid residue not conserved in the wild-type PhoS proteins exemplified above.

The mutant PhoS protein has the "specific mutation" in the amino acid sequence of such a wild-type PhoS protein as described above.

That is, in other words, the mutant PhoS protein may be identical to any of the wild-type PhoS proteins exemplified above or conservative variants thereof except that the mutant PhoS protein has the "specific mutation". Specifically, the mutant PhoS protein may be, for example, a protein having any of the amino acid sequences shown in SEQ ID NOS: 2 to 7 except that the mutant PhoS protein has the "specific mutation". Specifically, the mutant PhoS protein may also be, for example, a protein having any of the amino acid sequences shown in SEQ ID NOS: 2 to 7 but including substitution, deletion, insertion, and/or addition of one or several amino acid residues, except that the mutant PhoS protein has the "specific mutation". Specifically, the mutant PhoS protein may also be, for example, a protein showing an identity of 80% or more, 90% or more, 95% or more, 97% or more, or 99% or more, to any of the amino acid sequences shown in SEQ ID NOS: 2 to 7 except that the mutant PhoS protein has the "specific mutation".

Furthermore, in other words, the mutant PhoS protein may be a variant of any of the wild-type PhoS proteins exemplified above having the "specific mutation", and further including a conservative mutation at a site other than that of the "specific mutation". Specifically, the mutant PhoS protein may be, for example, a protein having any of the amino acid sequences shown in SEQ ID NOS: 2 to 7 but having the "specific mutation", and further including substitution, deletion, insertion, and/or addition of one or several amino acid residues at a site other than that of the "specific mutation".

The mutant phoS gene is not particularly limited so long as it encodes such a mutant PhoS protein as described above.

Hereinafter, the "specific mutation" of the mutant PhoS protein will be explained.

The "specific mutation" is not particularly limited, so long as it is a mutation that changes the amino acid sequence of such a wild-type PhoS protein described above, and that is effective for secretory production of a heterologous protein.

It is preferred that the "specific mutation" is a mutation that improves the secretory production amount of a heterologous protein. The expression "to improve the secretory production amount of a heterologous protein" means that a coryneform bacterium modified so as to have a mutant phoS gene (modified strain) is able to produce the heterologous protein by secretory production in an amount larger than that obtainable with a non-modified strain. The "non-modified strain" refers to a control strain not having the "specific mutation" in the phoS gene, i.e., a control strain not having any mutant phoS gene, and it may be, for example, a wild-type strain or a parent strain. Although the degree of increase meant by the expression "to produce a heterologous protein by secretory production in an amount larger than that obtainable with a non-modified strain" is not particularly limited so long as the secretory production amount of the heterologous protein is increased compared with that obtainable with a non-modified strain, the expression may mean that the heterologous protein is produced by secretory production in an amount of, for example, 1.1 times or more, 1.2 times or more, 1.3 times or more, 2 times or more, or 5 times or more, of that obtainable with a non-modified strain, in terms of the accumulation amount in the medium and/or on the cell surface layer. In addition, the expression "to produce a heterologous protein by secretory production in an amount larger than that obtainable with a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB. The expression "to improve the secretory production amount of a heterologous protein" does not necessarily mean that the secretory production amount of every heterologous protein is improved, and it is sufficient that the secretory production amount of a heterologous protein chosen as the target of secretory production is improved. The expression "to improve the secretory production amount of a heterologous protein" may specifically mean, for example, that the secretory production amount of a heterologous protein described in the Example section herein is improved.

Whether a certain mutation is a mutation that improves the secretory production amount of a heterologous protein can be confirmed by, for example, preparing a strain modified so as to have a gene encoding the PhoS protein having the certain mutation from a strain belonging to a coryneform bacterium, quantifying the amount of the heterologous protein produced by secretory production when the strain is cultured in a medium, and comparing it with the amount of the heterologous protein produced by secretory production when the strain before the modification (non-modified strain) is cultured in the medium.

Preferred examples of the change of the amino acid sequence include substitution of an amino acid residue. That is, it is preferred that the "specific mutation" is a mutation of replacing an amino acid residue of the wild-type PhoS protein with another amino acid residue. The amino acid residue substituted by the "specific mutation" may be one residue, or may be a combination of two or more residues. The amino acid residue substituted by the "specific mutation" may be an amino acid residue other than the histidine residue that is autophosphorylated. The amino acid residue substituted by the "specific mutation" may be an amino acid residue in the HisKA domain other than the histidine residue that is autophosphorylated. The term "histidine residue that is autophosphorylated" refers to a histidine residue at position 276 of the wild-type PhoS protein. The term "HisKA domain" refers to a region formed of amino acid residues at positions 266-330 of the wild-type PhoS protein. The amino acid residue substituted by the "specific mutation" may be a tryptophan residue at position 302 of the wild-type PhoS protein (W302).

In the aforementioned mutation, examples of the amino acid residue after substitution include K(Lys), R(Arg), H(His), A(Ala), V(Val), L(Leu), I(Ile), G(Gly), S(Ser), T(Thr), P(Pro), F(Phe), W(Trp), Y(Tyr), C(Cys), M(Met), D(Asp), E(Glu), N(Asn), and Q(Gln), provided that the amino acid residue after substitution is other than the original one. As the amino acid residue after substitution, for example, one resulting in improvement in the secretory production amount of a heterologous protein can be chosen.

When substitution occurs at W302, examples of the amino acid residue after substitution include amino acid residues other than aromatic amino acid and histidine residues. Specific examples of the "amino acid residues other than aromatic amino acid and histidine residues" include K(Lys), R(Arg), A(Ala), V(Val), L(Leu), I(Ile), G(Gly), S(Ser), T(Thr), P(Pro), C(Cys), M(Met), D(Asp), E(Glu), N(Asn), and Q(Gln). More specific examples of the "amino acid residues other than aromatic amino acid and histidine residues" include K(Lys), A(Ala), V(Val), S(Ser), C(Cys), M(Met), D(Asp), and N(Asn).

The term "specific mutation" used for the phoS gene refers to a mutation on the nucleotide sequence thereof that results in such a "specific mutation" as described above into the encoded PhoS protein.

In the present disclosure, the "amino acid residue at position X of the wild-type PhoS protein" refers to an amino acid residue corresponding to the amino acid residue at position X in SEQ ID NO: 2. For example, "W302" refers to an amino acid residue corresponding to the tryptophan residue at position 302 in SEQ ID NO: 2. The aforementioned positions of amino acid residues indicate relative positions, and the absolute positions thereof may shift due to deletion, insertion, addition, or the like of an amino acid residue or residues. For example, if one amino acid residue is deleted or inserted at a position on the N-terminal side of position X in the amino acid sequence shown as SEQ ID NO: 2, the amino acid residue originally at position X is relocated at position X−1 or X+1 counted from the N-terminus, however, it is still regarded as the "amino acid residue at position X of the wild-type PhoS protein". Specifically, for example, "W302" refers to the tryptophan residue at positions 302, 302, 302, 321, 275, and 286, respectively, in the amino acid sequences of wild-type PhoS proteins shown in SEQ ID NOS: 2 to 7. Furthermore, the "histidine residue at position 276 of the wild-type PhoS protein (histidine residue that is autophosphorylated)" refers to the histidine residue at positions 276, 276, 276, 295, 249, and 260, respectively, in the amino acid sequences of wild-type PhoS proteins shown in SEQ ID NOS: 2 to 7. Furthermore, the "region formed of amino acid residues at positions 266-330 of the wild-type PhoS protein (HisKA domain)" refers to the region formed of amino acid residues at positions 266-330, 266-330, 266-330, 285-349, 239-303, and 250-314, respectively, in the amino acid sequences of wild-type PhoS proteins shown in SEQ ID NOS: 2 to 7.

Incidentally, while "W302" referred to herein is typically a tryptophan residue, it may also be other than a tryptophan residue. That is, when the wild-type PhoS protein has an amino acid sequence other than the amino acid sequences shown in SEQ ID NOS: 2 to 7, "W302" can be other than a tryptophan residue. Hence, for example, the "mutation replacing W302 with a cysteine residue" includes not only a mutation, when "W302" is a tryptophan residue, for replacing this tryptophan residue with a cysteine residue, but also includes a mutation, when "W302" is K(Lys), R(Arg), H(His), A(Ala), V(Val), L(Leu), I(Ile), G(Gly), S(Ser), T(Thr), P(Pro), F(Phe), Y(Tyr), M(Met), D(Asp), E(Glu), N(Asn), or Q(Gln), for replacing this residue with a cysteine residue. The same can be applied similarly to the other mutations.

Which amino acid residue is the "amino acid residue corresponding to the amino acid residue at position X in SEQ ID NO: 2" in the amino acid sequence of an arbitrary PhoS protein can be determined by alignment between the amino acid sequence of the arbitrary PhoS protein and the amino acid sequence of SEQ ID NO: 2. The alignment can be performed by, for example, using known gene analysis software. Specific examples of such software include DNA-SIS produced by Hitachi Solutions, GENETYX produced by Genetyx, and so forth (Elizabeth C. Tyler et al., Computers and Biomedical Research, 24 (1) 72-96, 1991; Barton G J et al., Journal of Molecular Biology, 198 (2), 327-37, 1987).

The mutant phoS gene can be obtained by, for example, modifying a wild-type phoS gene so that the encoded PhoS protein has the aforementioned "specific mutation". The wild-type phoS gene to be modified can be obtained by, for example, cloning from an organism having the wild-type phoS gene, or chemical synthesis. Furthermore, the mutant phoS gene can also be obtained without using a wild-type phoS gene. For example, the mutant phoS gene may be directly obtained by chemical synthesis. The obtained mutant phoS gene may be further modified before use.

Genes can be modified by known methods. For example, an objective mutation can be introduced into a target site of DNA by the site-specific mutagenesis method. Examples of the site-specific mutagenesis method include a method of using PCR (Higuchi, R., 61, in PCR Technology, Erlich, H. A. Eds., Stockton Press (1989); Carter P., Meth. In Enzymol., 154, 382 (1987)), and a method of using a phage (Kramer, W. and Frits, H. J., Meth. in Enzymol., 154, 350 (1987); Kunkel, T. A. et al., Meth. in Enzymol., 154, 367 (1987)).

Hereinafter, methods for modifying a coryneform bacterium to have a mutant phoS gene will be explained.

A coryneform bacterium can be modified to have a mutant phoS gene by introducing the mutant phoS gene into the coryneform bacterium. A coryneform bacterium can be modified to have a mutant phoS gene also by introducing a mutation into the phoS gene on the chromosome of the coryneform bacterium. A mutation can be introduced into a gene on a chromosome by natural mutation, mutagenesis treatment, or genetic engineering means.

Methods for introducing a mutant phoS gene into a coryneform bacterium are not particularly limited. It is sufficient that the mutant phoS gene is harbored by the bacterium of the present disclosure so that it can be expressed under control of a promoter that functions in a coryneform bacterium. The promoter may be a promoter derived from the host, or a heterogenous promoter. The promoter may be the native promoter of the phoS gene, or a promoter of another gene. In the bacterium of the present disclosure, the mutant phoS gene may be present on a vector that autonomously replicates out of the chromosome, such as a plasmid, or may be incorporated into the chromosome. The bacterium of the present disclosure may have only one copy of the mutant phoS gene, or two or more copies of the mutant phoS gene. The bacterium of the present disclosure may have only one kind of mutant phoS gene, or two or more kinds of mutant phoS genes. The mutant phoS gene can be introduced, for example, in the same manner as that for introduction of a gene in methods for increasing the expression of a gene described below, or for introduction of the genetic construct used for the present disclosure described below.

The bacterium of the present disclosure may or may not have the wild-type phos gene. It is preferred that the bacterium of the present disclosure does not have the wild-type phoS gene.

A coryneform bacterium not having the wild-type phoS gene can be obtained by disrupting the wild-type phoS gene on the chromosome. The wild-type phoS gene can be disrupted by known methods. Specifically, the wild-type phoS gene can be disrupted by, for example, deleting a part or the whole of the promoter region and/or the coding region of the wild-type phoS gene.

Furthermore, by replacing the wild-type phoS gene on the chromosome with a mutant phoS gene, a coryneform bacterium modified so that it does not have the wild-type phoS gene and has the mutant phoS gene can be obtained. Examples of methods for performing such gene substitution include, for example, a method of using a linear DNA such as a method called "Red driven integration" (Datsenko, K. A, and Wanner, B. L., Proc. Natl. Acad. Sci. USA, 97:6640-6645 (2000)), a method of utilizing the Red driven integration in combination with an excision system derived from λ phage (Cho, E. H., Gumport, R. I., Gardner, J. F., J. Bacteriol., 184:5200-5203 (2002)) (refer to WO 2005/010175), a method of using a plasmid including a temperature sensitive replication origin, a method of using a plasmid capable of conjugative transfer, a method of utilizing a suicide vector not including a replication origin that functions in a host (U.S. Pat. No. 6,303,383, Japanese Patent Laid-open (Kokai) No. 05-007491), and so forth.

The PhoS protein functions, i.e., induces a response against phosphate depletion in the environment, in combination with a response regulator PhoR protein. Hence, the bacterium of the present disclosure has a phoR gene so that the mutant PhoS protein functions. The phoR gene is a gene encoding a PhoR protein, which is a response regulator of the PhoRS system. The expression "to have a phoR gene" is also referred to as "to have a PhoR protein". Typically, it is sufficient that the PhoR protein inherently possessed by the bacterium of the present disclosure functions in combination with the mutant PhoS protein. Alternatively, the bacterium of the present disclosure may be introduced with an appropriate phoR gene, in addition to or instead of the phoR gene inherently possessed by the bacterium of the present disclosure. The phoR gene to be introduced is not particularly limited, as long as it encodes a PhoR protein that functions in combination with the mutant PhoS protein.

Examples of the phoR gene include, for example, phoR genes of coryneform bacteria. Specific examples of the phoR genes of coryneform bacteria include, for example, the phoR genes of *C. glutamicum* YDK010, *C. glutamicum* ATCC 13032, *C. glutamicum* ATCC 14067, *C. callunae, C. crenatum*, and *C. efficiens*. The nucleotide sequence of the phoR gene of *C. glutamicum* ATCC 13032 and the amino acid sequence of the PhoR protein of the same are shown as SEQ ID NO: 8 and 9, respectively.

The phoR gene may be a variant of any of the phoR genes exemplified above, so long as the original function thereof is maintained. Similarly, the PhoR protein may be a variant of any of the PhoR proteins exemplified above, so long as the original function thereof is maintained. That is, the term "phoR gene" includes not only the phoR genes exemplified above, but also includes conservative variants thereof. Similarly, the term "PhoR protein" includes not only the PhoR proteins exemplified above, but also includes conservative variants thereof. The aforementioned descriptions concerning conservative variants of the RegX3 protein and the regX3 gene can be applied similarly to variants of the phoR gene and PhoR protein. For example, the phoR gene may be a gene encoding a protein having the aforementioned amino acid sequence, but including substitution, deletion, insertion, and/or addition of one or several amino acid residues at one or several positions, so long as the original function is maintained. The expression "the original function is maintained" used for the PhoR protein may mean that a variant of the protein has a function as a PhoR protein (such as a function of a protein consisting of the amino acid sequence shown as SEQ ID NO: 9). Furthermore, the expression "the original function is maintained" used for the PhoR protein may also mean that a variant of the protein has a function as a response regulator of the PhoRS system. That is, the term "function as a PhoR protein" may specifically refer to a function as a response regulator of the PhoRS system. The term "function as a response regulator of the PhoRS system" may specifically refer to a function of inducing a response against phosphate depletion in the environment in combination with a sensor kinase PhoS protein. The term "function as a response regulator of the PhoRS system" may more specifically refer to a function of being activated via transfer of phosphate group from the PhoS protein that sensed phosphate depletion in the environment to be autophosphorylated, and regulating the expression of genes that respond to phosphate depletion in the environment.

Whether or not a variant of the PhoR protein has a function as a response regulator of the PhoRS system can be confirmed by, for example, introducing a gene encoding the variant into a phoR-gene-deletion strain of a coryneform bacterium, and confirming whether or not responsiveness against phosphate depletion is complemented. Complementation of responsiveness against phosphate depletion can be detected, for example, as improvement of growth under phosphate depletion conditions, or as induction of the expression of genes of which the expression is known to be induced under phosphate depletion conditions (J. Bacteriol., 188, 724-732 (2006)). As the phoR-gene-deletion strain of a coryneform bacterium, for example, a phoR-gene-deletion strain of *C. glutamicum* YDK010 or a phoR-gene-deletion strain of *C. glutamicum* ATCC 13032 can be used.

<1-3-2> Reduction in Activity of Cell Surface Layer Protein

The bacterium of the present disclosure may be a bacterium of which the activity(s) of cell surface layer protein(s) is/are reduced. Specifically, the bacterium of the present disclosure may be a bacterium of which the activity(s) of cell surface layer protein(s) is/are reduced as compared with a non-modified strain. The phrase "the activity of a cell surface layer protein is reduced" may particularly mean that the number of molecules of the cell surface layer protein per cell is reduced. Hereinafter, the cell surface layer proteins and genes encoding them will be explained.

The cell surface layer protein is a protein constituting the surface layer (S layer) of bacteria or archaea. Examples of cell surface layer proteins of coryneform bacteria include PS1 and PS2 (CspB) of *C. glutamicum* (Japanese Patent Laid-open (Kohyo) No. 6-502548), and SlpA (CspA) of *C. stationis* (Japanese Patent Laid-open (Kokai) No. 10-108675). It is preferable to reduce the activity of the PS2 protein among these.

The nucleotide sequence of the cspB gene of *C. glutamicum* ATCC 13869 and the amino acid sequence of the PS2 protein (CspB protein) encoded by the gene are shown in SEQ ID NOS: 10 and 11, respectively.

Furthermore, for example, amino acid sequences of CspB homologues were reported for 28 strains of *C. glutamicum* (J. Biotechnol., 112, 177-193 (2004)). These 28 strains of *C. glutamicum* and the GenBank accession numbers of the cspB gene homologues in NCBI database are exemplified below (the GenBank accession numbers are shown in parentheses).

C. *glutamicum* ATCC 13058 (AY524990)
C. *glutamicum* ATCC 13744 (AY524991)
C. *glutamicum* ATCC 13745 (AY524992)
C. *glutamicum* ATCC 14017 (AY524993)
C. *glutamicum* ATCC 14020 (AY525009)
C. *glutamicum* ATCC 14067 (AY524994)
C. *glutamicum* ATCC 14068 (AY525010)
C. *glutamicum* ATCC 14747 (AY525011)
C. *glutamicum* ATCC 14751 (AY524995)
C. *glutamicum* ATCC 14752 (AY524996)
C. *glutamicum* ATCC 14915 (AY524997)
C. *glutamicum* ATCC 15243 (AY524998)
C. *glutamicum* ATCC 15354 (AY524999)
C. *glutamicum* ATCC 17965 (AY525000)
C. *glutamicum* ATCC 17966 (AY525001)
C. *glutamicum* ATCC 19223 (AY525002)
C. *glutamicum* ATCC 19240 (AY525012)
C. *glutamicum* ATCC 21341 (AY525003)
C. *glutamicum* ATCC 21645 (AY525004)
C. *glutamicum* ATCC 31808 (AY525013)
C. *glutamicum* ATCC 31830 (AY525007)
C. *glutamicum* ATCC 31832 (AY525008)
C. *glutamicum* LP-6 (AY525014)
C. *glutamicum* DSM20137 (AY525015)
C. *glutamicum* DSM20598 (AY525016)
C. *glutamicum* DSM46307 (AY525017)
C. *glutamicum* 22220 (AY525005)
C. *glutamicum* 22243 (AY525006)

Since the nucleotide sequence of a gene encoding a cell surface layer protein may differ depending on the species or strain to which the coryneform bacterium belongs, the gene encoding a cell surface layer protein may be a variant of any genes encoding the cell surface layer proteins exemplified above, so long as the original function thereof is maintained. Similarly, the cell surface layer protein may be a variant of any of the cell surface layer proteins exemplified above, so long as the original function thereof is maintained. That is, the term "cspB gene" includes not only the cspB genes exemplified above, but also includes conservative variants thereof. Similarly, the term "CspB protein" includes not only the CspB proteins exemplified above, but also includes conservative variants thereof. The aforementioned descriptions concerning conservative variants of the RegX3 protein and the regX3 gene can be applied similarly to variants of the cell surface layer protein and the gene encoding it. For example, the gene encoding the cell surface layer protein may be a gene encoding a protein having the aforementioned amino acid sequence, but including substitution, deletion, insertion, and/or addition of one or several amino acid residues at one or several positions, so long as the original function is maintained. The expression "original function is maintained" used for the cell surface layer protein may mean that the protein has a property that if the activity of the protein is reduced in a coryneform bacterium, the secretory production amount of a heterologous protein is increased compared with that obtainable with a non-modified strain.

The "property that if the activity of the protein is reduced in a coryneform bacterium, the secretory production amount of a heterologous protein is increased compared with that obtainable with a non-modified strain" refers to a property imparting an ability to produce a heterologous protein by secretory production in an amount larger than that obtainable with a non-modified strain to a coryneform bacterium when the activity thereof is reduced in the coryneform bacterium. The "non-modified strain" refers to a control strain of which the activity(s) of cell surface layer protein(s) is/are not reduced, and it may be, for example, a wild-type strain or a parent strain. Although the degree of increase meant by the expression "to produce a heterologous protein by secretory production in an amount larger than that obtainable with a non-modified strain" is not particularly limited so long as the secretory production amount of the heterologous protein is increased compared with that obtainable with a non-modified strain, the expression may mean that the heterologous protein is produced by secretory production in an amount of, for example, 1.1 times or more, 1.2 times or more, 1.3 times or more, or 2 times or more, of that obtainable with a non-modified strain, in terms of the accumulation amount in the medium and/or on the cell surface layer. In addition, the expression "to produce a heterologous protein by secretory production in an amount larger than that obtainable with a non-modified strain" may also mean that whereas the heterologous protein cannot be detected when a non-concentrated culture supernatant of a non-modified strain is applied to SDS-PAGE and stained with CBB, the heterologous protein can be detected when a non-concentrated culture supernatant of a modified strain is applied to SDS-PAGE and stained with CBB.

Whether a protein has a property that if the activity of the protein is reduced in a coryneform bacterium, the secretory production amount of a heterologous protein is increased compared with that obtainable with a non-modified strain, can be confirmed by preparing a strain modified so that the activity of the protein is reduced from a strain belonging to the coryneform bacteria, quantifying the secretory production amount of the heterologous protein observed when the modified strain is cultured in a medium, and comparing the quantified amount with the secretory production amount of the heterologous protein observed when the strain before being modified (un-modified strain) is cultured in the medium.

In the present disclosure, the expression "activity of a cell surface layer protein is reduced" includes a case where a coryneform bacterium has been modified so that the activity of a cell surface layer protein is reduced and a case where the activity of a cell surface layer protein is inherently reduced in a coryneform bacterium. The "case where activity of a cell surface layer protein is inherently reduced in a coryneform bacterium" includes a case where a coryneform bacterium is inherently deficient in a cell surface layer protein. That is, examples of a coryneform bacterium in which the activity of a cell surface layer protein is reduced include a coryneform bacterium that is inherently deficient in a cell surface layer protein. Examples of the "case where a coryneform bacterium is inherently deficient in a cell surface layer protein" include a case where a coryneform bacterium is inherently deficient in the gene encoding a cell surface layer protein. The expression "a coryneform bacterium is inherently deficient in a cell surface layer protein" may mean that a coryneform bacterium is inherently deficient in one or more proteins selected from cell surface layer protein(s) found in other strain(s) of the species to which the coryneform bacterium belongs. For example, "*C. glutamicum* is inherently deficient in a cell surface layer protein" may mean that a *C. glutamicum* strain is inherently deficient in one or more cell surface layer protein(s) found in other *C. glutamicum* strain(s), i.e., for example, deficient in PS1 and/or PS2 (CspB). Examples of the coryneform bacterium that is inherently deficient in a cell surface layer protein include *C. glutamicum* ATCC 13032, which is inherently deficient in the cspB gene.

<1-3-3> Protein Secretion System

The bacterium of the present disclosure has a protein secretion system. The protein secretion system is not particularly limited, so long as it can secrete an objective heterologous protein. Examples of the protein secretion system include Sec system (Sec secretion system) and Tat system (Tat secretion system). The bacterium of the present disclosure may have been modified so that the protein secretion system is enhanced. For example, the bacterium of the present disclosure may have been modified so that the expression of one or more genes encoding the Tat secretion system is increased. In the present disclosure, such a modification is also referred to as "enhancement of the Tat secretion system". Enhancement of the Tat secretion system is preferable particularly for cases of producing a heterologous protein by secretory production using a Tat-dependent signal peptide. Methods for increasing the expression of genes encoding the Tat secretion system are described in Japanese Patent No. 4730302.

Examples of the genes encoding the Tat secretion system include tatA, tatB, tatC, and tatE genes.

Specific examples of the genes encoding the Tat secretion system include tatA, tatB, and tatC genes of *C. glutamicum*. The tatA, tatB, and tatC genes of *C. glutamicum* ATCC 13032 correspond to the complementary sequence of positions 1571065-1571382, the sequence of positions 1167110-1167580, and the complementary sequence of positions 1569929-1570873 in the genome sequence registered as GenBank accession NC_003450 (VERSION NC_003450.3 GI: 58036263) in NCBI database, respectively. The TatA, TatB, and TatC proteins of *C. glutamicum* ATCC 13032 have been registered as GenBank accession NP_600707 (version NP_600707.1 GI: 19552705, locus_tag="NCgl1434"), Gen-Bank accession NP_600350 (version NP_600350.1 GI: 19552348, locus_tag="NCgl1077"), and GenBank accession NP_600706 (version NP_600706.1 GI: 19552704, locus_tag="NCgl1433"), respectively. The nucleotide sequences of the tatA, tatB, and tatC genes of *C. glutamicum* ATCC 13032 and the amino acid sequences of the TatA, TatB, and TatC proteins of the same are shown as SEQ ID NOS: 12 to 17.

Specific examples of the genes encoding the Tat secretion system also include tatA, tatB, tatC, and tatE genes of *E. coli*. The tatA, tatB, tatC, and tatE genes of *E. coli* K-12 MG1655 correspond to the sequence of positions 4019968-4020237, the sequence of positions 4020241-4020756, the sequence of positions 4020759-4021535, and the sequence of positions 658170-658373 in the genome sequence registered as GenBank accession NC_000913 (VERSION NC_000913.2 GI: 49175990) in NCBI database, respectively. The TatA, TatB, TatC, and TatE proteins of *E. coli* K-12 MG1655 have been registered as GenBank accession NP_418280 (version NP_418280.4 GI: 90111653, locus_tag="b3836"), GenBank accession YP_026270 (version YP_026270.1 GI: 49176428, locus_tag="b3838"), GenBank accession NP_418282 (version NP_418282.1 GI: 16131687, locus_tag="b3839"), and GenBank accession NP_415160 (version NP_415160.1 GI: 16128610, locus_tag="b0627"), respectively.

The gene encoding the Tat secretion system may be a variant of any of the genes encoding the Tat-secretion-system exemplified above, so long as the original function thereof is maintained. Similarly, the Tat-secretion-system may be a variant of any of the Tat-secretion-systems exemplified above, so long as the original function thereof is maintained. That is, the terms "tatA gene", "tatB gene", "tatC gene", and "tatE gene" include not only the tatA, tatB, tatC, and tatE genes exemplified above, respectively, but also includes conservative variants thereof. Similarly, the terms "TatA protein", "TatB protein", "TatC protein", and "TatE protein" include not only the TatA, TatB, TatC, and TatE proteins exemplified above, respectively, but also includes conservative variants thereof. The aforementioned descriptions concerning conservative variants of the RegX3 protein and the regX3 gene can be applied similarly to variants of the Tat-secretion-system and the gene encoding it. For example, the gene encoding the Tat-secretion-system may be a gene encoding a protein having any of the aforementioned amino acid sequences, but including substitution, deletion, insertion, and/or addition of one or several amino acid residues at one or several positions, so long as the original function is maintained. The expression "original function is maintained" used for the Tat-secretion-system may mean that the system has a function of secreting a protein fused with a Tat-dependent signal peptide at the N-terminus out of the cell.

<1-4> Method for Reducing Activity of Protein

Hereinafter, methods for reducing the activity of a protein such as the RegX3 protein, HrrSA protein, and HrcA protein will be explained. The methods for reducing the activity of a protein described below can also be utilized for disruption of the wild-type PhoS protein.

The expression "the activity of a protein is reduced" means that the activity of the protein is reduced as compared with a non-modified strain. Specifically, the expression "the activity of a protein is reduced" means that the activity of the protein per cell is reduced as compared with that of a non-modified strain. The term "non-modified strain" used herein refers to a control strain that has not been modified so that the activity of an objective protein is reduced. Examples of the non-modified strain include a wild-type strain and parent strain. Specific examples of the non-modified strain include the respective type strains of the species of bacteria. Specific examples of the non-modified strain also include strains exemplified above in relation to the description of coryneform bacteria. That is, in an embodiment, the activity of a protein may be reduced as compared with a type strain, i.e., the type strain of the species to which the bacterium of the present disclosure belongs. In another embodiment, the activity of a protein may also be reduced as compared with *C. glutamicum* ATCC 13032. In another embodiment, the activity of a protein may also be reduced as compared with *C. glutamicum* ATCC 13869. In another embodiment, the activity of a protein may also be reduced as compared with *C. glutamicum* AJ12036 (FERM BP-734). In another embodiment, the activity of a protein may also be reduced as compared with *C. glutamicum* YDK010. The state that "the activity of a protein is reduced" also includes a state that the activity of the protein has completely disappeared. More specifically, the expression "the activity of a protein is reduced" may mean that the number of molecules of the protein per cell is reduced, and/or the function of each molecule of the protein is reduced as compared with those of a non-modified strain. That is, the term "activity" in the expression "the activity of a protein is reduced" is not limited to the catalytic activity of the protein, but may also mean the transcription amount of a gene (i.e., the amount of mRNA) encoding the protein or the translation amount of the gene (i.e., the amount of the protein). The phrase "the number of molecules of a protein per cell" may mean an average value per cell of the number of molecules of the protein. The state that "the number of molecules of the protein per cell is reduced" also includes a state that the protein does not exist at all. The state that "the function of each molecule of the protein is reduced" also includes a state that the function of each protein molecule has completely disappeared. The degree of the reduction in the activity of a protein is not particularly limited, so long as the activity is reduced as compared with that of a non-modified strain. The activity of a protein may be reduced to, for example, 50% or less, 20% or less, 10% or less, 5% or less, or 0% of that of a non-modified strain.

The modification for reducing the activity of a protein can be attained by, for example, reducing the expression of a gene encoding the protein. The phrase "the expression of a gene is reduced" means that the expression of the gene is reduced as compared with a non-modified strain. Specifically, the phrase "the expression of a gene is reduced" means that the expression amount of the gene per cell is reduced as compared with that of a non-modified strain. The phrase "the expression amount of a gene per cell" may mean an average value per cell of the expression amount of the gene. More specifically, the phrase "the expression of a gene is reduced" may mean that the transcription amount of the gene (i.e., the amount of mRNA) is reduced, and/or the translation amount of the gene (i.e., the amount of the protein expressed from the gene) is reduced. The state that "the expression of a gene is reduced" also includes a state that the gene is not expressed at all. The state that "the expression of a gene is reduced" is also referred to as "the expression of a gene is attenuated". The expression of a gene may be reduced to, for example, 50% or less, 20% or less, 10% or less, 5% or less, or 0% of that of a non-modified strain.

The reduction in gene expression may be due to, for example, a reduction in the transcription efficiency, a reduction in the translation efficiency, or a combination of them. The expression of a gene can be reduced by modifying an expression control sequence of the gene such as a promoter, Shine-Dalgarno (SD) sequence (also referred to as ribosome-binding site (RBS)), and spacer region between RBS and the start codon of the gene. When an expression control sequence is modified, one or more nucleotides, two or more nucleotides, or three or more nucleotides, of the expression control sequence are modified. The transcription efficiency of a gene can be reduced by, for example, replacing the promoter of the gene on a chromosome with a weaker promoter. The term "weaker promoter" means a promoter providing an attenuated transcription of a gene compared with an inherently existing wild-type promoter of the gene. Examples of weaker promoters include, for example, inducible promoters. That is, an inducible promoter may function as a weaker promoter under a non-induced condition, such as in the absence of the corresponding inducer. Furthermore, a part or the whole of an expression control sequence may be deleted. The expression of a gene can also be reduced by, for example, manipulating a factor responsible for expression control. Examples of the factor responsible for expression control include low molecules responsible for transcription or translation control (inducers, inhibitors, etc.), proteins responsible for transcription or translation control (transcription factors etc.), nucleic acids responsible for transcription or translation control (siRNA etc.), and so forth. Furthermore, the expression of a gene can also be reduced by, for example, introducing a mutation that reduces the expression of the gene into the coding region of the gene. For example, the expression of a gene can be reduced by replacing a codon in the coding region of the gene with a synonymous codon used less frequently in a host. Furthermore, for example, the gene expression may be reduced due to disruption of a gene as described later.

The modification for reducing the activity of a protein can also be attained by, for example, disrupting a gene encoding the protein. The expression "a gene is disrupted" means that a gene is modified so that a protein that can normally function is not produced. The state that "a protein that normally functions is not produced" includes a state that the protein is not produced at all from the gene, and a state that the protein of which the function (such as activity or property) per molecule is reduced or eliminated is produced from the gene.

Disruption of a gene can be attained by, for example, deleting the gene on a chromosome. The term "deletion of a gene" refers to deletion of a partial or entire region of the coding region of the gene. Furthermore, the whole of a gene including sequences upstream and downstream from the coding region of the gene on a chromosome may be deleted. The sequences upstream and downstream from the coding region of the gene may include, for example, an expression control sequence of the gene. The region to be deleted may be any region such as an N-terminal region (region encoding an N-terminal region of a protein), an internal region, or a C-terminal region (region encoding a C-terminal region of a protein), so long as the activity of the protein can be reduced. Deletion of a longer region can usually more surely inactivate the gene. The region to be deleted may be, for example, a region having a length of 10% or more, 20% or more, 30% or more, 40% or more, 50% or more, 60% or more, 70% or more, 80% or more, 90% or more, or 95% or more of the total length of the coding region of the gene. Furthermore, it is preferred that reading frames of the sequences upstream and downstream from the region to be deleted are not the same. Inconsistency of reading frames may cause a frame-shift downstream of the region to be deleted.

Disruption of a gene can also be attained by, for example, introducing a mutation for an amino acid substitution (missense mutation), a stop codon (nonsense mutation), addition or deletion of one or two nucleotide residues (frame shift mutation), or the like into the coding region of the gene on a chromosome (Journal of Biological Chemistry, 272:8611-8617 (1997); Proceedings of the National Academy of Sciences, USA, 95 5511-5515 (1998); Journal of Biological Chemistry, 26 116, 20833-20839 (1991)).

Disruption of a gene can also be attained by, for example, inserting another nucleotide sequence into a coding region of the gene on a chromosome. A site of the insertion may be in any region of the gene, and insertion of a longer nucleo-tide sequence can usually more surely inactivate the gene. It is preferred that reading frames of the sequences upstream and downstream from the insertion site are not the same. Inconsistency of reading frames may cause a frameshift downstream of the region to be deleted. The other nucleotide sequence is not particularly limited so long as a sequence that reduces or eliminates the activity of the encoded protein is chosen, and examples thereof include, for example, a marker gene such as antibiotic resistance genes, and a gene useful for production of an objective substance.

Particularly, disruption of a gene may be carried out so that the amino acid sequence of the encoded protein is deleted. In other words, the modification for reducing the activity of a protein can be attained by, for example, deleting the amino acid sequence of the protein, specifically, modi-fying a gene so as to encode a protein of which the amino acid sequence is deleted. The term "deletion of the amino acid sequence of a protein" refers to deletion of a partial or entire region of the amino acid sequence of the protein. In addition, the term "deletion of the amino acid sequence of a protein" means that the original amino acid sequence disappears in the protein, and also includes cases where the original amino acid sequence is changed to another amino acid sequence. That is, for example, a region that was changed to another amino acid sequence by frameshift may be regarded as a deleted region. When the amino acid sequence of a protein is deleted, the total length of the protein is typically shortened, but there can also be cases where the total length of the protein is not changed or is extended. For example, by deletion of a partial or entire region of the coding region of a gene, a region encoded by the deleted region can be deleted in the encoded protein. In addition, for example, by introduction of a stop codon into the coding region of a gene, a region encoded by the downstream region of the introduction site can be deleted in the encoded protein. In addition, for example, by frameshift in the coding region of a gene, a region encoded by the frameshift region can be deleted in the encoded protein. The aforementioned descriptions concerning the position and length of the region to be deleted in deletion of a gene can be applied similarly to the position and length of the region to be deleted in deletion of the amino acid sequence of a protein.

Such modification of a gene on a chromosome as described above can be attained by, for example, preparing a disruption-type gene modified so that it is unable to produce a protein that normally functions, and transforming a host with a recombinant DNA containing the disruption-type gene to cause homologous recombination between the disruption-type gene and the wild-type gene on a chromo-some and thereby substitute the disruption-type gene for the wild-type gene on the chromosome. In this procedure, if a marker gene selected according to the characteristics of the host such as auxotrophy is included in the recombinant DNA, the operation becomes easier. Examples of the disruption-type gene include a gene of which a partial or entire region of the coding region is deleted, gene including a missense mutation, gene including a nonsense mutation, gene including a frame shift mutation, and gene inserted with an insertion sequence such as a transposon or marker gene. The structure of the recombinant DNA to be used for homologous recombination is not particularly limited as long as it causes homologous recombination in a desired manner. For example, a host can be transformed with a linear DNA containing the disruption-type gene and further con-taining upstream and downstream sequences of the wild-type gene on the chromosome at the respective ends, so that homologous recombination occurs at each of upstream and downstream sides of the wild-type gene, to thereby replace the wild-type gene with the disruption-type gene in one step. The protein encoded by the disruption-type gene has a conformation different from that of the wild-type protein, even if it is produced, and thus the function thereof is reduced or eliminated. Such gene disruption based on gene substitution utilizing homologous recombination has already been established, and there are methods of using a linear DNA such as a method called "Red driven integration" (Datsenko, K. A, and Wanner, B. L., Proc. Natl. Acad. Sci. USA, 97:6640-6645 (2000)), and a method utilizing the Red driven integration in combination with an excision system derived from λ phage (Cho, E. H., Gumport, R. I., Gardner, J. F., J. Bacteriol., 184:5200-5203 (2002)) (refer to WO 2005/010175), a method of using a plasmid having a tem-perature sensitive replication origin, a method of using a plasmid capable of conjugative transfer, a method of utiliz-ing a suicide vector not having a replication origin that functions in a host (U.S. Pat. No. 6,303,383, Japanese Patent Laid-open (Kokai) No. 05-007491), and so forth.

Modification for reducing activity of a protein can also be attained by, for example, a mutagenesis treatment. Examples of the mutagenesis treatment include irradiation of X-ray or ultraviolet and treatment with a mutation agent such as N-methyl-N'-nitro-N-nitrosoguanidine (MNNG), ethyl methanesulfonate (EMS), and methyl methanesulfonate (MMS).

Such methods for reducing the activity of a protein as mentioned above may be used independently or in an arbitrary combination.

A reduction in the activity of a protein can be confirmed by measuring the activity of the protein.

A reduction in the activity of a protein can also be confirmed by confirming a reduction in the expression of a gene encoding the protein. A reduction in the expression of a gene can be confirmed by confirming a reduction in the transcription amount of the gene or a reduction in the amount of the protein expressed from the gene.

A reduction in the transcription amount of a gene can be confirmed by comparing the amount of mRNA transcribed from the gene with that of a non-modified strain. Examples of the method for evaluating the amount of mRNA include Northern hybridization, RT-PCR, microarray, RNA-Seq, and so forth (Molecular Cloning, Cold Spring Harbor Labora-tory Press, Cold Spring Harbor (USA), 2001). The amount of mRNA may be reduced to, for example, 50% or less, 20% or less, 10% or less, 5% or less, or 0% of that of a non-modified strain.

A reduction in the amount of a protein can be confirmed by performing SDS-PAGE and confirming the intensity of the separated protein band. A reduction in the amount of a protein can be confirmed by Western blotting using antibodies (Molecular Cloning, Cold Spring Harbor Laboratory Press, Cold Spring Harbor (USA) 2001). The amount of the protein (such as the number of molecules of the protein per cell) may be reduced to, for example, 50% or less, 20% or less, 10% or less, 5% or less, or 0% of that of a non-modified strain.

Disruption of a gene can be confirmed by determining nucleotide sequence of a part or the whole of the gene, restriction enzyme map, full length, or the like of the gene depending on the means used for the disruption.

<1-5> Method for Increasing Expression of Gene

Hereinafter, methods for increasing the expression of a gene, such as genes encoding the Tat secretion system, will be explained.

The phrase "the expression of a gene is increased" means that the expression of the gene is increased as compared with that of a non-modified strain. Specifically, the phrase "the expression of a gene is increased" means that the expression amount of the gene per cell is increased as compared with that of a non-modified strain. The phrase "the expression amount of a gene per cell" may mean an average value per cell of the expression amount of the gene. The term "non-modified strain" used herein refers to a control strain that has not been modified so that the expression of an objective gene is increased. Examples of the non-modified strain include a wild-type strain and parent strain. Specific examples of the non-modified strain include the respective type strains of the species of bacteria. Specific examples of the non-modified strain also include strains exemplified above in relation to the description of coryneform bacteria. That is, in an embodiment, the expression of a gene may be increased as compared with a type strain, i.e. the type strain of the species to which the bacterium of the present disclosure belongs. In another embodiment, the expression of a gene may also be increased as compared with *C. glutamicum* ATCC 13032. In another embodiment, the expression of a gene may also be increased as compared with *C. glutamicum* ATCC 13869. In another embodiment, the expression of a gene may also be increased as compared with *C. glutamicum* AJ12036 (FERM BP-734). In another embodiment, the expression of a gene may also be increased as compared with *C. glutamicum* YDK010. The phrase "the expression of a gene is increased" may more specifically mean that the transcription amount of the gene (i.e., the amount of mRNA) is increased, and/or the translation amount of the gene (i.e., the amount of the protein expressed from the gene) is increased. The state that "the expression of a gene is increased" may also be referred to as "the expression of a gene is enhanced". The degree of the increase in the expression of a gene is not particularly limited, so long as the expression of the gene is increased as compared with that of a non-modified strain. The expression of a gene may be increased to 1.5 times or more, 2 times or more, or 3 times or more, of that of a non-modified strain. Furthermore, the state that "the expression of a gene is increased" includes not only a state that the expression amount of an objective gene is increased in a strain that inherently expresses the objective gene, but also a state that the gene is introduced into a strain that does not inherently express the objective gene, and expressed therein. That is, the phrase "the expression of a gene is increased" also includes, for example, a state that an objective gene is introduced into a strain that does not possess the gene, and is expressed therein.

The expression of a gene can be increased by, for example, increasing the copy number of the gene.

The copy number of a gene can be increased by introducing the gene into the chromosome of a host. A gene can be introduced into a chromosome by, for example, using homologous recombination (Miller, J. H., Experiments in Molecular Genetics, 1972, Cold Spring Harbor Laboratory). Examples of the gene transfer method utilizing homologous recombination include, for example, a method using a linear DNA such as Red-driven integration (Datsenko, K. A., and Wanner, B. L., Proc. Natl. Acad. Sci. USA, 97:6640-6645 (2000)), a method of using a plasmid containing a temperature sensitive replication origin, a method of using a plasmid capable of conjugative transfer, a method of using a suicide vector not having a replication origin that functions in a host, or a transduction method using a phage. The structure of the recombinant DNA to be used for homologous recombination is not particularly limited as long as it causes homologous recombination in a desired manner. For example, a coryneform bacterium can be transformed with a linear DNA containing an objective gene and further containing upstream and downstream sequences of the substitution target region on the chromosome at the respective ends, so that homologous recombination occurs at each of upstream and downstream sides of the target region, to thereby replace the target region with the objective gene. The recombinant DNA to be used for homologous recombination may contain a marker gene for selection of transformants. Only one copy of, or two or more copies of a gene may be introduced. For example, by performing homologous recombination using a sequence which is present in multiple copies on a chromosome as a target, multiple copies of a gene can be introduced into the chromosome. Examples of such a sequence which is present in multiple copies on a chromosome include repetitive DNAs, and inverted repeats located at both ends of a transposon. Alternatively, homologous recombination may be performed by using an appropriate sequence on a chromosome such as a gene unnecessary for the production of an objective substance as a target. Furthermore, a gene can also be randomly introduced into a chromosome by using a transposon or Mini-Mu (Japanese Patent Laid-open (Kokai) No. 2-109985, U.S. Pat. No. 5,882,888, EP 805867 B1). As the transposon, an artificial transposon may also be used (Japanese Patent Laid-open (Kokai) No. 9-70291).

Introduction of a target gene into a chromosome can be confirmed by Southern hybridization using a probe having a sequence complementary to the whole gene or a part thereof, PCR using primers prepared on the basis of the sequence of the gene, or the like.

Furthermore, the copy number of a gene can also be increased by introducing a vector containing the gene into a host. For example, the copy number of a target gene can be increased by ligating a DNA fragment containing the target gene with a vector that functions in a host to construct an expression vector of the gene, and transforming the host with the expression vector. The DNA fragment containing the target gene can be obtained by, for example, PCR using the genomic DNA of a microorganism having the target gene as the template. As the vector, a vector autonomously replicable in the cell of the host can be used. The vector is preferably a multi-copy vector. Furthermore, the vector preferably has a marker such as an antibiotic resistance gene for selection of transformant. Furthermore, the vector may have a promoter and/or terminator for expressing the introduced gene. The vector may be, for example, a vector derived from a bacterial plasmid, a vector derived from a yeast plasmid, a vector derived from a bacteriophage, cosmid, phagemid, or the like. Specific examples of vector autonomously replicable in coryneform bacteria include, for example, pHM1519 (Agric. Biol. Chem., 48, 2901-2903 (1984)); pAM330 (Agric. Biol. Chem., 48, 2901-2903 (1984)); plasmids obtained by improving these and having a drug resistance gene; plasmid pCRY30 (Japanese Patent Laid-open (Kokai) No. 3-210184); plasmids pCRY21, pCRY2KE, pCRY2KX, pCRY31, pCRY3KE, and pCRY3KX (Japanese Patent Laid-open (Kokai) No. 2-72876 and U.S. Pat. No. 5,185,262); plasmids pCRY2 and pCRY3 (Japanese Patent Laid-open (Kokai) No. 1-191686); pAJ655, pAJ611, and pAJ1844 (Japanese Patent Laid-open (Kokai) No. 58-192900); pCG1 (Japanese Patent Laid-open (Kokai) No. 57-134500); pCG2 (Japanese Patent Laid-open (Kokai) No. 58-35197); pCG4 and pCG11 (Japanese Patent Laid-open (Kokai) No. 57-183799); pVK7 (Japanese Patent Laid-open (Kokai) No. 10-215883); pVK9 (US2006-0141588); pVC7 (Japanese Patent Laid-open (Kokai) No. 9-070291); pVS7 (WO2013/069634).

When a gene is introduced, it is sufficient that the gene is expressibly harbored by a host. Specifically, it is sufficient that the gene is harbored by the host so that it is expressed under control by a promoter that functions in the host. The promoter is not particularly limited so long as it functions in the host. The term "promoter that functions in a host" refers to a promoter that shows a promoter activity in the host. The promoter may be a promoter derived from the host, or a heterogenous promoter. The promoter may be the native promoter of the gene to be introduced, or a promoter of another gene. As the promoter, such a promoter as mentioned later which functions in a coryneform bacterium can be used.

A terminator for terminating the gene transcription can be provided downstream of the gene. The terminator is not particularly limited so long as it functions in the host. The terminator may be a terminator derived from the host or may be a heterogenous terminator. The terminator may be the native terminator of the gene to be introduced or may be a terminator of another gene.

Vectors, promoters, and terminators available in various microorganisms are disclosed in detail in "Fundamental Microbiology Vol. 8, Genetic Engineering, KYORITSU SHUPPAN CO., LTD, 1987", and those can be used.

Furthermore, when two or more genes are introduced, it is sufficient that the genes each are expressibly harbored by the bacterium of the present disclosure. For example, all the genes may be carried by a single expression vector or a chromosome. Furthermore, the genes may be separately carried by two or more expression vectors, or separately carried by a single or two or more expression vectors and a chromosome. An operon constituted by two or more genes may also be introduced.

The gene to be introduced is not particularly limited so long as it codes for a protein that functions in a host. The gene to be introduced may be a gene derived from the host or may be a heterogenous gene. The gene to be introduced can be obtained by, for example, PCR using primers designed on the basis of the nucleotide sequence of the gene, and using the genomic DNA of an organism having the gene, a plasmid carrying the gene, or the like as the template. The gene to be introduced may also be totally synthesized, for example, on the basis of the nucleotide sequence of the gene (Gene, 60 (1), 115-127 (1987)). The obtained gene can be used as it is, or after being modified as required. A gene can be modified by a known technique. For example, an objective mutation can be introduced into an objective site of DNA by the site-specific mutation method. That is, the coding region of a gene can be modified by the site-specific mutation method so that a specific site of the encoded protein include(s) substitution, deletion, insertion, and/or addition of amino acid residue(s).

Furthermore, the expression of a gene can be increased by improving the transcription efficiency of the gene. In addition, the expression of a gene can also be increased by improving the translation efficiency of the gene. The transcription efficiency of the gene and the translation efficiency of the gene can be improved by, for example, modifying an expression control sequence of the gene. The term "expression control sequence" collectively refers to sites that affect the expression of a gene. Examples of the expression control sequence include, for example, promoter, Shine-Dalgarno (SD) sequence (also referred to as ribosome binding site (RBS)), and spacer region between RBS and the start codon. Expression control sequences can be identified by using a promoter search vector or gene analysis software such as GENETYX. These expression control sequences can be modified by, for example, homologous recombination. Examples of methods for modification using homologous recombination include a method of using a temperature sensitive vector, or the Red driven integration method (WO2005/010175).

The transcription efficiency of a gene can be improved by, for example, replacing the promoter of the gene on a chromosome with a stronger promoter. The "stronger promoter" means a promoter providing an improved transcription of a gene compared with an inherently existing wild-type promoter of the gene. Examples of stronger promoters usable in coryneform bacteria include the artificially modified P54-6 promoter (Appl. Microbiol. Biotechnol., 53, 674-679 (2000)), pta, aceA, aceB, adh, and amyE promoters inducible in coryneform bacteria with acetic acid, ethanol, pyruvic acid, or the like, cspB, SOD, and tuf (EF-Tu) promoters, which are strong promoters capable of providing a large expression amount in coryneform bacteria (Journal of Biotechnology, 104 (2003) 311-323; Appl. Environ. Microbiol., 2005 December; 71 (12): 8587-96), as well as lac promoter, tac promoter, and trc promoter. Furthermore, as the stronger promoter, a highly-active type of an existing promoter may also be obtained by using various reporter genes. For example, by making the −35 and −10 regions in a promoter region closer to the consensus sequence, the activity of the promoter can be enhanced (WO 00/18935). Methods for evaluating the strength of promoters and examples of strong promoters are described in Goldstein et al. (Prokaryotic Promoters in Biotechnology, Biotechnol. Annu. Rev., 1, 105-128 (1995)), and so forth.

The translation efficiency of a gene can be improved by, for example, replacing the Shine-Dalgarno (SD) sequence (also referred to as ribosome binding site (RBS)) for the gene on a chromosome with a stronger SD sequence. The "stronger SD sequence" means a SD sequence that provides an improved translation of mRNA compared with the inherently existing wild-type SD sequence of the gene. Examples of stronger SD sequences include, for example, RBS of the gene 10 derived from phage T7 (Olins P. O. et al, Gene, 1988, 73, 227-235). Furthermore, it is known that substitution, insertion, or deletion of several nucleotides in a spacer region between RBS and the start codon, especially in a sequence immediately upstream of the start codon (5'-UTR), significantly affects the stability and translation efficiency of mRNA, and hence, the translation efficiency of a gene can also be improved by modifying them.

The translation efficiency of a gene can also be improved by, for example, modifying codons. For example, the translation efficiency of a gene can be improved by replacing a rare codon present in the gene with a synonymous codon more frequently used. That is, the gene to be introduced may be modified, for example, to contain optimal codons according to the frequencies of codons observed in a host to be used. Codons can be replaced by, for example, the site-specific mutation method. Alternatively, a gene fragment in which objective codons are replaced may be totally synthesized. Frequencies of codons in various organisms are disclosed in the "Codon Usage Database" (www.kazusa.or.jp/codon; Nakamura, Y. et al, Nucl. Acids Res., 28, 292 (2000)).

Furthermore, the expression of a gene can also be increased by amplifying a regulator that increases the expression of the gene, or deleting or attenuating a regulator that reduces the expression of the gene.

Such methods for increasing the gene expression as mentioned above may be used independently or in an arbitrary combination.

The method for the transformation is not particularly limited, and conventionally known methods can be used. There can be used, for example, a method of treating recipient cells with calcium chloride so as to increase the permeability thereof for DNA, which has been reported for the *Escherichia coli* K-12 strain (Mandel, M. and Higa, A., J. Mol. Biol., 1970, 53, 159-162), and a method of preparing competent cells from cells which are in the growth phase, followed by transformation with DNA, which has been reported for *Bacillus subtilis* (Duncan, C. H., Wilson, G. A. and Young, F. E., Gene, 1977, 1:153-167). Alternatively, there can also be used a method of making DNA-recipient cells into protoplasts or spheroplasts, which can easily take up recombinant DNA, followed by introducing a recombinant DNA into the DNA-recipient cells, which is known to be applicable to *Bacillus subtilis*, actinomycetes, and yeasts (Chang, S. and Choen, S. N., 1979, Mol. Gen. Genet., 168:111-115; Bibb, M. J., Ward, J. M. and Hopwood, O. A., 1978, Nature, 274:398-400; Hinnen, A., Hicks, J. B. and Fink, G. R., 1978, Proc. Natl. Acad. Sci. USA, 75:1929-1933). Transformation of coryneform bacteria can be carried out by, specifically, for example, the protoplast method (Gene, 39, 281-286 (1985)), the electroporation method (Bio/Technology, 7, 1067-1070 (1989)), the electric pulse method (Japanese Patent Laid-open (Kokai) No. 2-207791), or the like.

An increase in the expression of a gene can be confirmed by, for example, confirming an increase in the activity of the protein expressed from the gene. An increase in the activity of a protein can be confirmed by measuring the activity of the protein. For example, an increase in the activity of the Tat secretion system can be confirmed by confirming an increase in the secretory production amount of a protein fused with a Tat-dependent signal peptide at the N-terminus. In such a case, it is preferred that the secretory production amount of the protein fused with a Tat-dependent signal peptide at the N-terminus is increased to 1.5 times or more, 2 times or more, or 3 times or more, of that of a non-modified strain.

An increase in the expression of a gene can also be confirmed by, for example, confirming an increase in the transcription amount of the gene, or by confirming an increase in the amount of a protein expressed from the gene.

An increase of the transcription amount of a gene can be confirmed by comparing the amount of mRNA transcribed from the gene with that of a non-modified strain such as a wild-type strain or parent strain. Examples of the method for evaluating the amount of mRNA include Northern hybridization, RT-PCR, microarray, RNA-Seq, and so forth (Sambrook, J., et al., Molecular Cloning A Laboratory Manual/

Third Edition, Cold Spring Harbor Laboratory Press, Cold Spring Harbor (USA), 2001). The amount of mRNA may be increased to, for example, 1.5 times or more, 2 times or more, or 3 times or more, of that of a non-modified strain.

An increase in the amount of a protein can be confirmed by performing SDS-PAGE and confirming the intensity of the separated protein band. An increase in the amount of a protein can be confirmed by Western blotting using antibodies (Molecular Cloning, Cold Spring Harbor Laboratory Press, Cold Spring Harbor (USA), 2001). The amount of the protein (such as the number of molecules of the protein per cell) may be increased to, for example, 1.5 times or more, 2 times or more, or 3 times or more, of that of a non-modified strain.

<1-6> Genetic Construct for Secretory Expression of Heterologous Protein and Introduction of the Same It is known that a secretory protein is generally translated as a preprotein (also referred to as prepeptide) or a preproprotein (also referred to as prepropeptide), and then becomes a mature protein through processing. Specifically, a secretory protein is generally translated as a preprotein or preproprotein, then a signal peptide as the pre-moiety is cleaved with a protease (generally called signal peptidase), and the secretory protein is thereby converted into a mature protein or proprotein. As for the proprotein, the pro-moiety thereof is further cleaved by a protease, and the proprotein thereby becomes a mature protein. Therefore, a signal peptide is used for the secretory production of a heterologous protein in the method of the present disclosure. In the present disclosure, a preprotein and a preproprotein of a secretory protein may be collectively referred to as "secretory protein precursor". In the present disclosure, the "signal peptide" (also referred to as "signal sequence") refers to an amino acid sequence present at the N-terminus of a secretory protein precursor, and not usually present in the natural mature protein.

The genetic construct used for the present disclosure includes, in the direction from 5' to 3', a promoter sequence that functions in a coryneform bacterium, a nucleic acid sequence encoding a signal peptide that functions in a coryneform bacterium, and a nucleic acid sequence encoding a heterologous protein. The nucleic acid sequence encoding the signal peptide may be ligated downstream from the promoter sequence so that the signal peptide is expressed under the control of the promoter. The nucleic acid sequence encoding the heterologous protein may be ligated downstream from the nucleic acid sequence encoding the signal peptide so that the heterologous protein is expressed as a fusion protein with the signal peptide. This fusion protein is also referred to as "fusion protein of the present disclosure". In the fusion protein of the present disclosure, the signal peptide and the heterologous protein may be or may not be adjacent to each other. That is, the expression "a heterologous protein is expressed as a fusion protein with a signal peptide" includes not only cases where a heterologous protein is expressed as a fusion protein with a signal peptide, in which the signal peptide and the heterologous protein are adjacent to each other, but also include cases where a heterologous protein is expressed as a fusion protein in which the signal peptide and the heterologous protein are fused with each other via another amino acid sequence. For example, as described later, the fusion protein of the present disclosure can contain an insertion sequence, such as an amino acid sequence including Gln-Glu-Thr and an amino acid sequence used for enzymatic digestion, between the signal peptide and the heterologous protein. As described later, it is acceptable that the eventually-obtained heterologous protein does not possess the signal peptide. That is, the expression "a heterologous protein is expressed as a fusion protein with a signal peptide" means that it is sufficient that the heterologous protein constitutes a fusion protein with a signal peptide at the time of expression, and it does not necessarily mean that the eventually-obtained heterologous protein constitutes a fusion protein with a signal peptide. A nucleic acid sequence may also be read as "gene". For example, a nucleic acid sequence encoding a heterologous protein is also referred to as a "gene encoding a heterologous protein" or "heterologous protein gene". Examples of the nucleic acid sequence include DNA. The genetic construct used for the present disclosure may also include a control sequence (operator, SD sequence, terminator, etc.) effective for expression of the fusion protein of the present disclosure in a coryneform bacterium at such an appropriate position that it can function.

The promoter used in the present disclosure is not particularly limited so long as a promoter that functions in a coryneform bacterium is chosen. The promoter may be a promoter derived from a coryneform bacterium, such as one derived from the host, or it may be a heterologous promoter. The promoter may be the native promoter of the heterologous protein, or a promoter of another gene. The "promoter that functions in a coryneform bacterium" refers to a promoter that possesses promoter activity in a coryneform bacterium.

Specific examples of the heterologous promoter include, for example, promoters derived from *E. coli* such as tac promoter, lac promoter, trp promoter, and araBAD promoter. Among these, strong promoters such as tac promoter and inducible promoters such as araBAD promoter are preferred.

Examples of the promoter derived from a coryneform bacterium include, for example, promoters of the genes of the cell surface layer proteins PS1, PS2 (also referred to as CspB), and SlpA (also referred to as CspA), and promoters of various amino acid biosynthesis system genes. Specific examples of the promoters of various amino acid biosynthesis system genes include, for example, promoters of the glutamate dehydrogenase gene of the glutamic acid biosynthesis system, the glutamine synthetase gene of the glutamine synthesis system, the aspartokinase gene of the lysine biosynthesis system, the homoserine dehydrogenase gene of the threonine biosynthesis system, the acetohydroxy acid synthetase gene of the isoleucine and valine biosynthesis system, 2-isopropylmalate synthetase gene of the leucine biosynthesis system, the glutamate kinase gene of the proline and arginine biosynthesis system, the phosphoribosyl-ATP pyrophosphorylase gene of the histidine biosynthesis system, the deoxyarabinoheptulonate phosphate (DAHP) synthetase gene of the aromatic amino acid biosynthesis systems such as those for tryptophan, tyrosine, and phenyl-alanine, the phosphoribosyl pyrophosphate (PRPP) amido-transferase gene of the nucleic acid biosynthesis systems such as those for inosinic acid and guanylic acid, the inosinic acid dehydrogenase gene, and the guanylic acid synthetase gene.

Examples of the promoter that functions in a coryneform bacterium include such strong promoters as described above usable in coryneform bacteria. As the promoter, a high activity type of an existing promoter may be obtained by using various reporter genes, and used. For example, by making the −35 and −10 regions in a promoter region closer to a consensus sequence, activity of the promoter can be enhanced (International Patent Publication WO 00/18935). Examples of the method for evaluating strength of a promoter and strong promoters are described in Goldstein et al.

(Prokaryotic promoters in biotechnology, Biotechnol. Annu. Rev., 1, 105-128 (1995)) and so forth. Furthermore, it is known that substitution, insertion, or deletion of several nucleotides in a spacer region between the ribosome-binding site (RBS) and the start codon, especially in a sequence immediately upstream of the start codon (5'-UTR), significantly affects stability and translation efficiency of mRNA, and these sequences can also be modified.

The signal peptide used in the present disclosure is not particularly limited so long as a signal peptide that functions in a coryneform bacterium is chosen. The signal peptide may be a signal peptide derived from a coryneform bacterium, such as one derived from the host, or it may be a heterologous signal peptide. The signal peptide may be the native signal peptide of the heterologous protein, or a signal peptide of another gene. The "signal peptide that functions in a coryneform bacterium" refers to a peptide that, when it is ligated to the N-terminus of an objective protein, allows the coryneform bacterium to secrete the protein. Whether a signal peptide functions in a coryneform bacterium can be confirmed by, for example, expressing an objective protein in a form of being fused with the signal peptide, and confirming whether the protein is secreted.

Examples of the signal peptide include Tat-dependent signal peptides and Sec-dependent signal peptides.

The term "Tat-dependent signal peptide" refers to a signal peptide recognized by the Tat system. The term "Tat-dependent signal peptide" may specifically refer to a signal peptide that, upon being linked at the N-terminus of an objective protein, results in secretion of the protein by the Tat secretion system.

Examples of the Tat-dependent signal peptide include the signal peptide of the TorA protein (trimethylamine-N-oxidoreductase) of *E. coli*, the signal peptide of SufI protein (suppressor of ftsI) of *E. coli*, the PhoD protein (phosphodiesterase) of *Bacillus subtilis*, the signal peptide of LipA protein (lipoic acid synthase) of *Bacillus subtilis*, and the signal peptide of IMD protein (isomaltodextranase) of *Arthrobacter globiformis*. The amino acid sequences of these signal peptides are as follows.

```
TorA signal peptide:
                                      (SEQ ID NO: 18)
MNNNDLFQASRRRFLAQLGGLTVAGMLGPSLLTPRRATA SufI signal peptide:
                                      (SEQ ID NO: 19)
MSLSRRQFIQASGIALCAGAVPLKASA PhoD signal peptide:
                                      (SEQ ID NO: 20)
MAYDSRFDEWVQKLKEESFQNNTFDRRKFIQGAGKIAGLSLGLTIAQS LipA signal peptide:
                                      (SEQ ID NO: 21)
MKFVKRRTTALVTTLMLSVTSLFALQPSAKAAEH IMD signal peptide:
                                      (SEQ ID NO: 22)
MMNLSRRTLLTTGSAATLAYALGMAGSAQA
```

The Tat-dependent signal peptide has a twin-arginine motif. Examples of the twin-arginine motif include S/T-R-R-X-F-L-K (SEQ ID NO: 23) and R-R-X-#-#(#: hydrophobic residue) (SEQ ID NO: 24).

The term "Sec-dependent signal peptide" refers to a signal peptide recognized by the Sec system. The term "Sec-dependent signal peptide" may specifically refer to a signal peptide that, upon being linked at the N-terminus of an objective protein, results in secretion of the protein by the Sec secretion system.

Examples of the Sec-dependent signal peptide include a signal peptide of a cell surface layer protein of a coryneform bacterium. The cell surface layer protein of coryneform bacteria is as described above. Examples of the cell surface layer protein of coryneform bacteria include PS1 and PS2 (CspB) derived from *C. glutamicum* (Japanese Patent Laid-open (Kohyo) No. 6-502548), and SlpA (CspA) derived from *C. ammoniagenes* (*C. stationis*) (Japanese Patent Laid-open (Kokai) No. 10-108675). The amino acid sequence of the signal peptide of PS1 (PS1 signal peptide) of *C. gluta-micum* is shown in SEQ ID NO: 25, the amino acid sequence of the signal peptide of PS2 (CspB) (PS2 signal peptide) of *C. glutamicum* is shown in SEQ ID NO: 26, and the amino acid sequence of the signal peptide of SlpA (CspA) (SlpA signal peptide) of *C. stationis* is shown in SEQ ID NO: 27.

The Tat-dependent signal peptide may be a variant of any of the Tat-dependent signal peptides exemplified above, so long as it contains a twin-arginine motif and the original function thereof is maintained. The Sec-dependent signal peptide may be a variant of any of the Sec-dependent signal peptides exemplified above, so long as the original function thereof is maintained. The above descriptions concerning conservative variants of the RegX3 protein and the regX3 gene can be applied similarly to variants of the signal peptide and the gene encoding it. For example, the signal peptide may be a peptide having any of the aforementioned amino acid sequences, but including substitution, deletion, insertion, and/or addition of one or several amino acid residues at one or several positions. The number meant by the term "one or several" used for a variant of the signal peptide is specifically 1 to 7, 1 to 5, 1 to 3, or 1 to 2. In the present disclosure, the terms "TorA signal peptide", "SufI signal peptide", "PhoD signal peptide", "LipA signal pep-tide", "IMD signal peptide", "PS1 signal peptide", "PS2 signal peptide", and "SlpA signal peptide" include not only the peptides of SEQ ID NOS: 18 to 27, respectively, but also includes conservative variants thereof.

The expression "original function is maintained" used for the Tat-dependent signal peptide means that the peptide is recognized by the Tat system, and specifically may mean that the peptide has a function of, upon being linked at the N-terminus of an objective protein, resulting in secretion of the protein by the Tat secretion system. Whether a peptide functions as the Tat-dependent signal peptide can be con-firmed by, for example, confirming an increase in the secre-tory production amount of a protein linked with the peptide at the N-terminus due to enhancement of the Tat secretion system, or confirming a reduction in the secretory produc-tion amount of a protein linked with the peptide at the N-terminus due to deletion of the Tat secretion system.

The expression "original function is maintained" used for the Sec-dependent signal peptide means that the peptide is recognized by the Sec system, and specifically, may mean that the peptide has a function of, upon being linked at the N-terminus of an objective protein, resulting in secretion of the protein by the Sec secretion system. Whether a peptide functions as the Sec-dependent signal peptide can be con-firmed by, for example, confirming an increase in the secre-tory production amount of a protein linked with the peptide at the N-terminus due to enhancement of the Sec secretion system, or confirming a reduction in the secretory produc-tion amount of a protein linked with the peptide at the N-terminus due to deletion of the Sec secretion system.

The signal peptide is generally cleaved by a signal pep-tidase, when the translation product is secreted out of the cell. That is, it is acceptable that the eventually-obtained heterologous protein does not possess the signal peptide. As a gene encoding a signal peptide, although a naturally occurring gene may be used as it is, it may be modified so that it has the optimal codons according to codon frequen-cies in a host to be used.

In the genetic construct used for the present disclosure, a nucleic acid sequence encoding an amino acid sequence including Gln-Glu-Thr may be inserted between the nucleic acid sequence encoding the signal peptide and the nucleic acid sequence encoding the heterologous protein (WO 2013/062029). The "amino acid sequence including Gln-Glu-Thr" is also referred to as "insertion sequence used for the present disclosure". Examples of the insertion sequence used for the present disclosure include amino acid sequences including Gln-Glu-Thr described in WO 2013/062029. Particularly, the insertion sequence used for the present disclosure can be used preferably in combination with the Sec-dependent signal peptide.

The insertion sequence used for the present disclosure is preferably a sequence consisting of 3 or more amino acid residues from the N-terminus of the mature protein of the cell surface layer protein CspB of a coryneform bacterium (henceforth also referred to as "mature CspB" or "CspB mature protein"). The term "sequence consisting of 3 or more amino acid residues from the N-terminus" refers to an amino acid sequence starting from the amino acid residue at position 1 of the N-terminus to an amino acid residue at position 3 or a more remote position.

The cell surface layer protein CspB of coryneform bac-teria is as described above. Specific examples of CspB include, for example, CspB of *C. glutamicum* ATCC 13869, CspB of 28 strains of *C. glutamicum* exemplified above, and variants thereof. In the amino acid sequence of the CspB protein of *C. glutamicum* ATCC 13869 shown in SEQ ID NO: 11, the amino acid residues at positions 1 to 30 correspond to the signal peptide, and the amino acid residues at positions 31 to 499 correspond to the CspB mature protein. The amino acid sequence of the CspB mature protein of *C. glutamicum* ATCC 13869, except for the 30 amino acid residues as the signal peptide moiety, is shown in SEQ ID NO: 28. In the mature CspB of *C. glutamicum* ATCC 13869, the amino acid residues at positions 1 to 3 of the N-terminus correspond to Gln-Glu-Thr.

The insertion sequence used for the present disclosure is preferably an amino acid sequence starting from the amino acid residue at position 1 to an amino acid residue at any of the positions 3 to 50 of the mature CspB. The insertion sequence used for the present disclosure is more preferably an amino acid sequence starting from the amino acid residue at position 1 to an amino acid residue at any of the positions 3 to 8, 17, and 50 of the mature CspB. The insertion sequence used for the present disclosure may be an amino acid sequence starting from the amino acid residue at position 1 to an amino acid residue at any of the positions 4, 6, 17 and 50 of the mature CspB.

The insertion sequence used for the present disclosure may be an amino acid sequence from among the following amino acid sequences (A) to (H):

```
(A)
Gln-Glu-Thr
```

45

```
                    -continued
(B)
                                    (SEQ ID NO: 29)
    Gln-Glu-Thr-Xaa1

(C)
                                    (SEQ ID NO: 30)
    Gln-Glu-Thr-Xaa1-Xaa2

(D)
                                    (SEQ ID NO: 31)
    Gln-Glu-Thr-Xaa1-Xaa2-Xaa3
```

(E) an amino acid sequence consisting of Gln-Glu-Thr fused with the amino acid residues at positions 4 to 7 of a mature CspB, (F) an amino acid sequence consisting of Gln-Glu-Thr fused with the amino acid residues at positions 4 to 8 of a mature CspB, (G) an amino acid sequence consisting of Gln-Glu-Thr fused with the amino acid residues at positions 4 to 17 of a mature CspB, (H) an amino acid sequence consisting of Gln-Glu-Thr fused with the amino acid residues at positions 4 to 50 of a mature CspB.

In the amino acid sequences (A) to (H), Xaa1 is Asn, Gly, Thr, Pro, or Ala, Xaa2 is Pro, Thr, or Val, and Xaa3 is Thr or Tyr. As for the amino acid sequences (A) to (H), "Gln-Glu-Thr fused with the amino acid residues at positions 4 to X of a mature CspB" means that the amino acid residues at positions 4 to X of the N-terminus of a mature CspB is fused to Thr of Gln-Glu-Thr. The first to third amino acid residues of the N-terminus of a mature CspB are usually Gln-Glu-Thr, and in such a case, "an amino acid sequence consisting of Gln-Glu-Thr fused with the amino acid residues at positions 4 to X of a mature CspB" is synonymous with an amino acid sequence formed of the amino acid residues at position 1 to X of the mature CspB.

Furthermore, specifically, the insertion sequence used for the present disclosure may be an amino acid sequence from among Gln-Glu-Thr-Asn-Pro-Thr (SEQ ID NO: 32), Gln-Glu-Thr-Gly-Thr-Tyr (SEQ ID NO: 33), Gln-Glu-Thr-Thr-Val-Thr (SEQ ID NO: 34), Gln-Glu-Thr-Pro-Val-Thr (SEQ ID NO: 35), and Gln-Glu-Thr-Ala-Val-Thr (SEQ ID NO: 36).

In the present disclosure, the "amino acid residue at position X of the mature CspB" refers to an amino acid residue corresponding to the amino acid residue at position X in SEQ ID NO: 28. Which amino acid residue is the "amino acid residue corresponding to the amino acid residue at position X in SEQ ID NO: 28" in the amino acid sequence of an arbitrary mature CspB can be determined by alignment between the amino acid sequence of the arbitrary mature CspB and the amino acid sequence of SEQ ID NO: 28.

Examples of the heterologous protein to be produced by secretory production according to methods of the present disclosure include, for example, physiologically active proteins, receptor proteins, antigenic proteins to be used as vaccines, enzymes, and any other proteins.

Examples of the enzymes include, for example, transglutaminase, protein glutaminase, isomaltodextranase, protease, endopeptidase, exopeptidase, aminopeptidase, carboxypeptidase, collagenase, chitinase, and so forth. Examples of transglutaminase include, for example, secretory-type transglutaminases of Actinomycetes such as *Streptoverticillium mobaraense* IFO 13819 (WO 01/23591), *Streptoverticillium cinnamoneum* IFO 12852, *Streptoverticillium griseocarneum* IFO 12776, and *Streptomyces lydicus* (WO 96/06931), and of filamentous fungi such as Oomycetes (WO 96/22366). Examples of protein glutaminase include, for example, protein glutaminase of *Chryseobacterium proteolyticum* (WO 2005/103278). Examples of isomaltodextranase include, for example, isomaltodextranase of *Arthrobacter globiformis* (WO 2005/103278).

Examples of the physiologically active proteins include, for example, growth factors, hormones, cytokines, and antibody-related molecules.

Specific examples of the growth factors include, for example, epidermal growth factor (EGF), insulin-like growth factor-1 (IGF-1), transforming growth factor (TGF), nerve growth factor (NGF), brain-derived neurotrophic factor (BDNF), vascular endothelial growth factor (VEGF), granulocyte-colony stimulating factor (G-CSF), granulocyte-macrophage-colony stimulating factor (GM-CSF), platelet-derived growth factor (PDGF), erythropoietin (EPO), thrombopoietin (TPO), acidic fibroblast growth factor (aFGF or FGF1), basic fibroblast growth factor (bFGF or FGF2), keratinocyte growth factor (KGF-1 or FGF7, and, KGF-2 or FGF10), and hepatocyte growth factor (HGF).

Specific examples of the hormones include, for example, insulin, glucagon, somatostatin, human growth hormone (hGH), parathyroid hormone (PTH), calcitonin, and exenatide.

Specific examples of the cytokines include, for example, interleukins, interferons, and tumor necrosis factors (TNFs).

The growth factors, hormones, and cytokines may not be strictly distinguished from one another. For example, a physiologically active protein may be a protein belonging to a single group from among growth factors, hormones, and cytokines, or may be a protein belonging to a plurality of groups selected from those.

Furthermore, a physiologically active protein may be an intact protein, or may be a part of a protein. Examples of a part of a protein include, for example, a part having physiological activity. Specific examples of a part having physiological activity include, for example, Teriparatide, a physiologically active peptide formed of the N-terminal 34 amino acid residues of parathyroid hormone (PTH).

The term "antibody-related molecule" refers to a protein containing a molecular species formed of a single domain or a combination of two or more domains from among the domains constituting a complete antibody. Examples of the domains constituting a complete antibody include heavy chain domains VH, CH1, CH2, and CH3, and light chain domains VL and CL. The antibody-related molecule may be a monomeric protein, or may be a multimeric protein, so long as it contains the above-mentioned molecular species. When the antibody-related molecule is a multimeric protein, it may be a homo-multimer formed of a single kind of subunit, or may be a hetero-multimer formed of two or more kinds of subunits. Specific examples of the antibody-related molecules include, for example, complete antibody, Fab, F(ab'), F(ab')$_2$, Fc, dimer formed of a heavy chain (H chain) and a light chain (L chain), Fc-fusion protein, heavy chain (H chain), light chain (L chain), light chain Fv (scFv), sc (Fv) 2, disulfide-bonded Fv (sdFv), diabody, and VHH fragment (Nanobody (registered trademark)). More specific examples of the antibody-related molecules include, for example, Trastuzumab.

The receptor proteins are not particularly limited. A receptor protein may be, for example, a receptor protein for any of physiologically active proteins and other physiologically active substances. Examples of the other physiologically active substances include, for example, neurotransmitters such as dopamine. Furthermore, a receptor protein may be an orphan receptor of which the corresponding ligand is not known.

The antigen proteins to be used as vaccines are not particularly limited, so long as they are proteins that can induce an immune response. An antigen protein can be appropriately selected depending on the intended object of the immune response.

In addition, examples of other proteins include Liver-type fatty acid-binding protein (LFABP), fluorescent protein, immunoglobulin-binding protein, albumin, and extracellular protein. Examples of the fluorescent protein include Green Fluorescent Protein (GFP). Examples of the immunoglobulin-binding protein include Protein A, Protein G, and Protein L. Examples of albumin include human serum albumin.

Examples of the extracellular protein include fibronectin, vitronectin, collagen, osteopontin, laminin, and partial sequences thereof. Laminin is a protein having a heterotrimeric structure consisting of an a chain, a β chain, and a γ chain. Examples of laminin include laminin of mammals. Examples of the mammals include primates such as human, monkey, and chimpanzee; rodents such as mouse, rat, hamster, and guinea pig; and other various mammals such as rabbit, horse, cattle, sheep, goat, pig, dog, and cat. Particular examples of the mammals include human. Examples of the subunit chains of laminin (i.e. α, β, and γ chains) include 5 kinds of α chains (α1 to α5), 3 kinds of β chains (β1 to β3), and 3 kinds of γ chains (γ1 to γ3). Laminin constitutes various isoforms depending on combinations of these subunits. Specific examples of laminin include, for example, laminin 111, laminin 121, laminin 211, laminin 213, laminin 221, laminin 311, laminin 321, laminin 332, laminin 411, laminin 421, laminin 423, laminin 511, laminin 521, and laminin 523. Examples of the partial sequence of laminin include laminin E8, which is an E8 fragment of laminin. Laminin E8 is a protein having a heterotrimeric structure formed of an E8 fragment of α chain (α chain E8), an E8 fragment of β chain (β chain E8), and an E8 fragment of γ chain (γ chain E8). The subunit chains of laminin E8 (i.e. a chain E8, β chain E8, and γ chain E8) are also collectively referred to as "E8 subunit chains". Examples of the E8 subunit chains includes E8 fragments of the laminin subunit chains exemplified above. Laminin E8 constitutes various isoforms depending on combinations of these E8 subunit chains. Specific examples of laminin E8 include, for example, laminin 111E8, laminin 121E8, laminin 211E8, laminin 221E8, laminin 332E8, laminin 421E8, laminin 411E8, laminin 511E8, and laminin 521E8.

A gene encoding the heterologous protein such as these proteins can be used as it is, or after being modified as required. A gene encoding the heterologous protein can be modified, for example, depending on a host to be used and/or for obtaining a desired activity. For example, a gene encoding the heterologous protein may be modified so that the amino acid sequence of the encoded heterologous protein includes substitution, deletion, insertion, and/or addition of one or several amino acid residues. The above descriptions concerning variants of the RegX3 protein and the regX3 gene can be applied similarly to the heterologous protein to be produced by secretory production by the method of the present disclosure and the gene encoding it. A protein specified with the type of organism from which the protein is derived is not limited to proteins per se found in that organism, and shall also include proteins having any of the amino acid sequences of proteins found in that organism and variants thereof. That is, for example, the term "protein derived from human" is not limited to proteins per se found in human, and shall also include proteins having any of the amino acid sequences of proteins found in human and variants thereof. Furthermore, in the gene encoding the heterologous protein, any codon(s) may be replaced with respective equivalent codon(s) thereof. For example, the gene encoding the heterologous protein may be modified so that it has optimal codons according to codon frequencies in the host to be used.

The genetic construct of the present disclosure may further include a nucleic acid sequence encoding an amino acid sequence used for enzymatic digestion between the nucleic acid sequence encoding the amino acid sequence including Gln-Glu-Thr and the nucleic acid sequence encoding the heterologous protein. If the amino acid sequence used for enzymatic digestion is inserted in the fusion protein of the present disclosure, the expressed fusion protein can be enzymatically digested to obtain the objective heterologous protein.

The amino acid sequence used for enzymatic digestion is not particularly limited so long as it is a sequence that can be recognized and digested by an enzyme that hydrolyzes a peptide bond, and a usable sequence can be appropriately chosen according to the amino acid sequence of the objective heterologous protein. The nucleic acid sequence encoding the amino acid sequence used for enzymatic digestion can be appropriately designed on the basis of that amino acid sequence. For example, the nucleic acid sequence encoding the amino acid sequence used for enzymatic digestion can be designed so that it has optimal codons according to codon frequencies observed in the host.

The amino acid sequence used for enzymatic digestion is preferably a recognition sequence of a protease showing high substrate specificity. Specific examples of such an amino acid sequence include, for example, a recognition sequence of factor Xa protease and a recognition sequence of proTEV protease. The factor Xa protease and the proTEV protease recognize the amino acid sequence of Ile-Glu-Gly-Arg (=IEGR, SEQ ID NO: 37) and the amino acid sequence of Glu-Asn-Leu-Tyr-Phe-Gln (=ENLYFQ, SEQ ID NO: 38) in a protein, respectively, to specifically digest the protein at the C-terminal side of each recognition sequence.

The N-terminal region of the heterologous protein eventually obtained by the methods of the present disclosure may be the same as that of the natural protein, or may not be the same as that of the natural protein. For example, the N-terminal region of the eventually obtained heterologous protein may be that of the natural protein including addition or deletion of one or several amino acid residues. Although the number of the "one or several" amino acid residues may differ depending on the full length or structure of the objective heterologous protein, specifically, it may be 1 to 20, 1 to 10, 1 to 5, or 1 to 3.

Furthermore, the heterologous protein to be produced by secretory production may be a protein including a pro-structure moiety (proprotein). When the heterologous protein to be produced by secretory production is a proprotein, the heterologous protein to be eventually obtained may be the proprotein or may not be the proprotein. That is, the proprotein may be processed into the mature protein by cleavage of the pro-structure moiety. The cleavage can be attained with, for example, a protease. When a protease is used, generally, the proprotein is preferably cleaved at a position substantially the same as that of the natural protein, or more preferably at exactly the same position as that of the natural protein so that the same mature protein as the natural mature protein is obtained, in view of the activity of the eventually obtained protein. Therefore, generally, a specific protease that cleaves the proprotein at such a position that the same protein as the naturally occurring mature protein is generated is most preferred. However, the N-terminal region of the heterologous protein to be eventually obtained may not be the same as that of the natural protein as described above. For example, depending on type, purpose of use, etc., of the heterologous protein to be produced, a protein having an N-terminus longer or shorter by one to several amino acid residues compared with the natural protein may have more appropriate activity. Proteases usable in the present disclosure include, for example, commercially available proteases such as Dispase (TM; produced by Boehringer Mannheim) as well as those obtainable from culture broth of a microorganism such as culture broth of actinomycetes. Such proteases may be used in an un-purified state or may be used after purification to an appropriate purity as required. When the pro-structure moiety is cleaved to obtain a mature protein, the inserted amino acid sequence including Gln-Glu-Thr is removed together with the pro-structure moiety, and therefore the objective protein can be obtained without providing an amino acid sequence used for enzymatic digestion downstream from the amino acid sequence including Gln-Glu-Thr.

The method for introducing the genetic construct used for the present disclosure into the coryneform bacterium is not particularly limited. The term "introduction of the genetic construct used for the present disclosure" refers to making a host harbor the genetic construct. The term "introduction of the genetic construct used for the present disclosure" includes not only cases where the genetic construct that has been preliminarily constructed is collectively introduced into a host, but also includes cases where at least the heterologous protein gene is introduced into a host and the genetic construct is constructed in the host. In the bacterium of the present disclosure, the genetic construct used for the present disclosure may be present on a vector that autonomously replicates out of the chromosome such as a plasmid, or may be incorporated into the chromosome. The genetic construct used for the present disclosure can be introduced, for example, in the same manner as that for introduction of a gene in methods for increasing the expression of a gene described above. In addition, for constructing the bacterium of the present disclosure, introduction of the genetic structure used for the present disclosure, impartation of the specific feature, and other modifications can be performed in any order.

The genetic construct used for the present disclosure can be introduced into a host by using, for example, a vector including the genetic construct. For example, the genetic construct used for the present disclosure can be introduced into a host by ligating the genetic construct with a vector to construct an expression vector of the genetic construct, and transforming the host with the expression vector. Also, when the vector contains a promoter that functions in a coryneform bacterium, an expression vector of the genetic construct used for the present disclosure can be constructed by ligating the nucleic acid sequence encoding the fusion protein of the present disclosure downstream from the promoter. The vector is not particularly limited so long as a vector autonomously replicable in a coryneform bacterium is chosen. The vector usable in a coryneform bacterium is as described above.

Furthermore, the genetic construct used for the present disclosure can be introduced into the chromosome of a host by using, for example, a transposon such as an artificial transposon. When a transposon is used, the genetic construct used for the present disclosure is introduced into the chromosome by homologous recombination or translocation ability of the transposon itself. Furthermore, the genetic construct used for the present disclosure can also be introduced into the chromosome of a host by other introduction methods utilizing homologous recombination. Examples of the introduction methods utilizing homologous recombination include, for example, methods utilizing a linear DNA, a plasmid having a temperature sensitive replication origin, a plasmid capable of conjugative transfer, a suicide vector not having a replication origin that functions in a host, and so forth. In addition, at least the heterologous protein gene may be introduced into the chromosome so that the genetic construct used for the present disclosure is constituted on the chromosome. In this case, a part or all of the constituents contained in the genetic construct, other than the heterologous protein gene, may be inherently present on the chromosome of the host. Specifically, for example, by using a promoter sequence inherently present on the chromosome of the host and a nucleic acid sequence encoding a signal peptide inherently present on the chromosome of the host and ligated downstream from the promoter sequence as they are, and replacing only the gene ligated downstream from the nucleic acid sequence encoding the signal peptide with an objective heterologous protein gene, the genetic construct used for the present disclosure can be constituted on the chromosome, and the bacterium of the present disclosure can be thereby constructed. A part of the genetic construct used for the present disclosure, such as the heterologous protein gene, can be introduced into the chromosome in the same manner as that for introduction of the genetic construct used for the present disclosure into the chromosome.

The genetic construct used for the present disclosure or a constituent thereof, such as promoter sequence, nucleic acid sequence encoding a signal peptide, or nucleic acid sequence encoding a heterologous protein, can be obtained by, for example, cloning. Specifically, for example, the genetic construct used for the present disclosure can be obtained by obtaining an objective heterologous protein gene by cloning from an organism having the objective heterologous protein, and then subjecting the gene to modification such as introduction of the nucleic acid sequence encoding the signal peptide and introduction of the promoter sequence. Furthermore, the genetic construct used for the present disclosure or a constituent thereof can also be obtained by chemical synthesis (Gene, 60 (1), 115-127 (1987)). The obtained genetic construct used for the present disclosure or constituent thereof can be used as it is, or after being modified as required.

Furthermore, when two or more kinds of proteins are expressed, it is sufficient that the genetic constructs for secretory expression of the proteins are harbored by the bacterium of the present disclosure so that secretory expression of the objective heterologous proteins can be attained. Specifically, for example, all the genetic constructs for secretory expression of the proteins may be harbored on a single expression vector, or harbored on the chromosome. Alternatively, the genetic constructs for secretory expression of the proteins may be separately harbored on a plurality of expression vectors, or may be separately harbored on one or more expression vectors and the chromosome. The "case where two or more kinds of proteins are expressed" refers to, for example, a case where two or more kinds of heterologous proteins are produced by secretory production, or a case where a hetero-multimeric protein is produced by secretory production.

The method for introducing the genetic construct used for the present disclosure into the coryneform bacterium is not particularly limited, and a generally used method, for example, the protoplast method (Gene, 39, 281-286 (1985)), the electroporation method (Bio/Technology, 7, 1067-1070 (1989)), the electric pulse method (Japanese Patent Laid-open (Kokai) No. 2-207791), and so forth can be used.

<2>: Method for Producing Heterologous Protein

By culturing the bacterium of the present disclosure obtained as described above to express a heterologous protein, a large amount of the heterologous protein secreted out of the cells is obtained.

The bacterium of the present disclosure can be cultured according to a usually used method and conditions. For example, the bacterium of the present disclosure can be cultured in a usual medium containing a carbon source, a nitrogen source, and inorganic ions. In order to obtain still higher proliferation, organic micronutrients such as vitamins and amino acids can also be added as required.

As the carbon source, carbohydrates such as glucose and sucrose, organic acids such as acetic acid, alcohols, and others can be used. As the nitrogen source, ammonia gas, aqueous ammonia, ammonium salts, and others can be used. As the inorganic ions, calcium ions, magnesium ions, phosphate ions, potassium ions, iron ions, and so forth are appropriately used as required. The culture is performed within appropriate ranges of pH 5.0 to 8.5 and 15 to 37° C. under aerobic conditions for 1 to 7 days. Furthermore, the culture conditions for L-amino acid production by coryneform bacteria and other conditions described for the methods for producing a protein using a Sec- or Tat-dependent signal peptide can be used (refer to WO 01/23591 and WO 2005/103278). Furthermore, when an inducible promoter is used for expression of the heterologous protein, culture may also be performed with adding a promoter-inducing agent to the medium. By culturing the bacterium of the present disclosure under such conditions, a large amount of the objective protein is produced in cells and efficiently secreted out of the cells. In addition, according to methods of the present disclosure, the produced heterologous protein is secreted out of the cells, and therefore a protein that is generally lethal if it is accumulated in a large amount in cells of microorganisms, such as transglutaminases, can also be continuously produced without lethal effect.

The protein secreted in the medium according to methods of the present disclosure can be separated and purified from the medium after the culture by a method well known to those skilled in the art. For example, after the cells are removed by centrifugation or the like, the protein can be separated and purified by a known appropriate method such as salting out, ethanol precipitation, ultrafiltration, gel filtration chromatography, ion exchange column chromatography, affinity chromatography, medium or high pressure liquid chromatography, reverse phase chromatography, and hydrophobic chromatography, or a combination of these. Furthermore, in a certain case, culture or culture supernatant may be used as it is. The protein secreted in the cell surface layer according to methods of the present disclosure can also be separated and purified in the same manner as that for the case where the protein is secreted in the medium, after solubilizing it by a method well known to those skilled in the art such as elevation of salt concentration and use of a surfactant. Furthermore, in a certain case, the protein secreted in the cell surface layer may be used as, for example, an immobilized enzyme, without solubilizing it.

Secretory production of the objective heterologous protein can be confirmed by performing SDS-PAGE for the culture supernatant and/or a fraction containing the cell surface layer as a sample, and confirming the molecular weight of the separated protein band. Furthermore, secretory production of the objective heterologous protein can also be confirmed by performing Western blotting using antibodies for the culture supernatant and/or a fraction containing the cell surface layer as a sample (Molecular Cloning, Cold spring Harbor Laboratory Press, Cold Spring Harbor (USA), 2001). Furthermore, secretory production of the objective heterologous protein can also be confirmed by detecting an N-terminal amino acid sequence of the objective protein using a protein sequencer. Furthermore, secretory production of the objective heterologous protein can also be confirmed by determining the mass of the objective protein using a mass spectrometer. Furthermore, when the objective heterologous protein is an enzyme or a protein having a certain measurable physiological activity, secretory production of the objective heterologous protein can be confirmed by measuring enzymatic activity or the physiological activity of the objective protein in the culture supernatant and/or a fraction containing the cell surface layer as a sample.

EXAMPLES

The present disclosure will be further specifically explained with reference to the following examples. However, the present disclosure is not limited to these examples.

Example 1: Construction of *Corynebacterium glutamicum* Deficient in regX3 Gene (1) Construction of regX3-Gene-Deletion Vector pBS5TΔregX3

The genome sequence of the *C. glutamicum* ATCC 13869 strain and the nucleotide sequence of the regX3 gene encoding the response regulator RegX3 of the two-component regulatory system SenX3-RegX3 have already been determined (GenBank Accession No. AP017557, NCBI locus-_tag CGBL_0104880).

PCR was carried out by using genomic DNA of the *C. glutamicum* ATCC 13869 strain prepared with PurElute™ Genomic DNA Kit (EdgeBio) as the template, in combination with primers of SEQ ID NOS: 49 and 50, to amplify a 5'-side upstream region of the regX3 gene of about 1 kbp, and in combination with primers of SEQ ID NOS: 51 and 52 to amplify a 3'-side downstream region of the regX3 gene of about 1 kbp. Then, PCR was carried out by using both amplified DNA fragments as the templates, in combination with primers of SEQ ID NOS: 49 and 52, to obtain a DNA fragment of about 2 kbp formed of mutually-fused both DNA fragments. PCR was carried out with Pyrobest® DNA polymerase (Takara Bio), and the reaction conditions were according to the protocol recommended by the manufacturer. This DNA fragment was inserted at SmaI site of pBS5T disclosed in WO 2006/057450, to obtain a regX3-gene-deletion vector pBS5TΔregX3. The ligation reaction was carried out with DNA Ligation Kit <Mighty Mix> (Takara Bio), and the reaction conditions were according to the protocol recommended by the manufacturer.

(2) Construction of regX3-Gene-Deletion Strain of YDK010::phoS(W302C) Strain

The *C. glutamicum* YDK010::phoS(W302C) strain disclosed in WO 2016/171224 was transformed with the plasmid pBS5TΔregX3 constructed in Example 1 (1). Strain selection from the obtained transformants was carried out according to the method disclosed in WO 2006/057450, to obtain a strain YDK010::phoS(W302C) ΔregX3, which is deficient in the regX3 gene.

Example 2: Construction of *Corynebacterium glutamicum* Deficient in hrrA Gene (1) Construction of hrrA-Gene-Deletion Vector pBS5TΔhrrA The genome sequence of the *C. glutamicum* ATCC 13869 strain and the nucleotide sequence of the hrrA gene encoding the response regulator HrrA of the two-component regulatory system HrrSA have already been determined (GenBank Accession No. AP017557, NCBI locus_tag CGBL_0128750).

PCR was carried out by using genomic DNA of the *C. glutamicum* ATCC 13869 strain prepared with PurElute™ Genomic DNA Kit (EdgeBio) as the template, in combination with primers of SEQ ID NOS: 53 and 54, to amplify a 5'-side upstream region of the hrrA gene of about 1 kbp, and in combination with primers of SEQ ID NOS: 55 and 56 to amplify a 3'-side downstream region of the hrrA gene of about 1 kbp. PCR was carried out with Pyrobest® DNA polymerase (Takara Bio), and the reaction conditions were according to the protocol recommended by the manufacturer. Each amplified DNA fragment of about 1 kbp was subject to agarose gel electrophoresis, an objective band was excised, and the DNA fragment was collected from the gel with Wizard® SV Gel and PCR Clean-Up System (Promega). The collected 2 DNA fragments were inserted at SmaI site of pBS5T disclosed in WO 2006/057450 by infusion reaction, to obtain an hrrA-gene-deletion vector pBS5TΔhrrA. The infusion reaction was carried out with In-Fusion® HD Cloning Kit (Takara Bio), and the reaction conditions were according to the protocol recommended by the manufacturer.

(2) Construction of hrrA-Gene-Deletion Strain of YDK010::phoS(W302C) Strain

The *C. glutamicum* YDK010::phoS(W302C) strain disclosed in WO 2016/171224 was transformed with the plasmid pBS5TΔhrrA constructed in Example 2 (1). Strain selection from the obtained transformants was carried out according to the method disclosed in WO 2006/057450, to obtain a strain YDK010::phoS(W302C) ΔhrrA, which is deficient in the hrrA gene.

Example 3: Construction of *Corynebacterium glutamicum* Deficient in hrcA Gene (1) Construction of hrcA-Gene-Deletion Vector pBS5TΔhrcA The genome sequence of the *C. glutamicum* ATCC 13869 strain and the nucleotide sequence of the hrcA gene encoding the transcription repressor HrcA of heat-shock proteins have already been determined (GenBank Accession No. AP017557, NCBI locus_tag CGBL_0121890).

PCR was carried out by using genomic DNA of the *C. glutamicum* ATCC 13869 strain prepared with PurElute™ Genomic DNA Kit (EdgeBio) as the template, in combination with primers of SEQ ID NOS: 57 and 58, to amplify a 5'-side upstream region of the hrcA gene of about 1 kbp, and in combination with primers of SEQ ID NOS: 59 and 60 to amplify a 3'-side downstream region of the hrcA gene of about 1 kbp. Then, PCR was carried out by using both amplified DNA fragments as the templates, in combination with primers of SEQ ID NOS: 57 and 60, to obtain a DNA fragment of about 2 kbp formed of mutually-fused both DNA fragments. PCR was carried out with Pyrobest® DNA polymerase (Takara Bio), and the reaction conditions were according to the protocol recommended by the manufacturer. This DNA fragment was inserted at SmaI site of pBS5T disclosed in WO 2006/057450, to obtain an hrcA-gene-deletion vector pBS5TΔhrcA. The ligation reaction was carried out with DNA Ligation Kit <Mighty Mix> (Takara Bio), and the reaction conditions were according to the protocol recommended by the manufacturer.

(2) Construction of hrcA-Gene-Deletion Strain of YDK010::phoS(W302C) Strain

The *C. glutamicum* YDK010::phoS(W302C) strain disclosed in WO 2016/171224 was transformed with the plasmid pBS5TΔhrcA constructed in Example 3 (1). Strain selection from the obtained transformants was carried out according to the method disclosed in WO 2006/057450, to obtain a strain YDK010::phoS(W302C) ΔhrcA, which is deficient in the hrcA gene.

Example 4: Construction of *Corynebacterium glutamicum* Double Deficient in regX3 and hrcA Genes The *C. glutamicum* YDK010::phoS(W302C) ΔregX3 strain constructed in Example 1 (2) was transformed with the plasmid pBS5TΔhrcA constructed in Example 3 (1). Strain selection from the obtained transformants was carried out according to the method disclosed in WO 2006/057450, to obtain a strain YDK010::phoS(W302C) ΔregX3ΔhrcA, which is double deficient in the regX3 and hrcA genes.

Example 5: Construction of *Corynebacterium glutamicum* Double Deficient in hrrA and hrcA Genes The *C. glutamicum* YDK010::phoS(W302C) ΔhrrA strain constructed in Example 2 (2) was transformed with the plasmid pBS5TΔhrcA constructed in Example 3 (1). Strain selection from the obtained transformants was carried out according to the method disclosed in WO 2006/057450, to obtain a strain YDK010::phoS(W302C) ΔhrrAΔhrcA, which is double deficient in the hrrA and hrcA genes.

Example 6: Construction of *Corynebacterium glutamicum* Double Deficient in regX3 and hrrA Genes The *C. glutamicum* YDK010::phoS(W302C) ΔregX3 strain constructed in Example 1 (2) was transformed with the plasmid pBS5TΔhrrA constructed in Example 2 (1). Strain selection from the obtained transformants was carried out according to the method disclosed in WO 2006/057450, to obtain a strain YDK010::phoS(W302C) ΔregX3ΔhrrA, which is double deficient in the regX3 and hrrA genes.

Example 7: Construction of *Corynebacterium glutamicum* Triple Deficient in regX3, hrrA, and hrcA Genes The *C. glutamicum* YDK010::phoS(W302C) ΔregX3ΔhrcA strain constructed in Example 4 (2) was transformed with the plasmid pBS5TΔhrrA constructed in Example 2 (1). Strain selection from the obtained transformants was carried out according to the method disclosed in WO 2006/057450, to obtain a strain YDK010::phoS (W302C) ΔregX3ΔhrrAΔhrcA, which is triple deficient in the regX3, hrrA, and hrcA genes.

Example 8: Secretory Production of VHH Antibody N15 Using *Corynebacterium Glutamicum* Deficient in Two or More Genes of regX3, hrrA, and hrcA Genes (1) Construction of Secretory Expression Plasmid of VHH Antibody N15

The amino acid sequence of VHH antibody N15 against an N-terminal domain of a protein IZUMO1 has already been determined (DDBJ Accession number: AB926006). This amino acid sequence is shown as SEQ ID NO: 61. Considering the codon frequency of *C. glutamicum*, a nucleotide sequence encoding N15 was designed. The designed nucleotide sequence is shown as SEQ ID NO: 62. Then, an expression cassette of a fusion protein of a signal peptide and N15 (hereinafter, also simply referred to as N15), in which a DNA encoding 25 amino acid residues formed of a signal peptide of CspA (also referred to as SlpA) derived from the *C. ammoniagenes* ATCC 6872 strain (GenBank Accession No. BAB62413) and the DNA of SEQ ID NO: 62 were linked downstream of the promoter of cspB gene of the *C. glutamicum* ATCC 13869 strain, and KpnI site and BamHI site was further added at the 5'-side and 3'-side termini respectively, was totally synthesized. The synthesized DNA fragment was treated with the restriction enzymes KpnI and BamHI and inserted at KpnI-BamHI site of pPK4 disclosed in Japanese Patent Laid-open (Kokai) No. 9-322774, to construct pPK4_CspAss_N15, which is a secretory expression plasmid of N15. As a result of nucleotide sequencing of the inserted fragment, it was confirmed that the gene encoding N15 was constructed as intended. Nucleotide sequencing was carried out with BigDye® Terminator v3.1 Cycle Sequencing Kit (Applied Biosystems) and 3130 Genetic Analyzer (Applied Biosystems).

(2) Secretory Production of VHH Antibody N15 Using *Corynebacterium glutamicum* Deficient in Two or More Genes of regX3, hrrA, and hrcA Genes The *C. glutamicum* YDK010::phoS(W302C) strain, the YDK010::phoS(W302C) ΔregX3ΔhrcA strain obtained in Example 4, the YDK010::phoS(W302C) ΔhrrAΔhrcA strain obtained in Example 5, the YDK010::phoS(W302C) ΔregX3ΔhrrA strain obtained in Example 6, and the YDK010::phoS(W302C) ΔregX3ΔhrrAΔhrcA strain obtained in Example 7 were each transformed with pPK4_CspAss_N15 obtained in Example 8 (1), which is a secretory expression plasmid of N15, to obtain strains YDK010::phoS(W302C)/pPK4_CspAss_N15, YDK010::phoS(W302C) ΔregX3ΔhrcA/pPK4_CspAss_N15, YDK010::phoS(W302C) ΔhrrAΔhrcA/pPK4_CspAss_N15, YDK010::phoS(W302C) ΔregX3ΔhrrA/pPK4_CspAss_N15, and YDK010::phoS(W302C) ΔregX3ΔhrrAΔhrcA/pPK4_CspAss_N15.

The obtained transformants were each cultured on MMTG liquid medium (120 g of glucose, 3 g of MgSO$_4$·7H$_2$O, 30 g of (NH$_4$)$_2$SO$_4$, 1.5 g of KH$_2$PO$_4$, 0.03 g of FeSO$_4$·7H$_2$O, 0.03 g of MnSO$_4$·5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO$_3$, filled up with water to 1 L, and adjusted to pH7.0) containing 25 mg/L of kanamycin at 30° C. for 72 hr.

After completion of the culture, 6.5 µL of the culture supernatant obtained by centrifuging each culture broth was subjected to reduced SDS-PAGE, and then staining was carried out with SYPRO Orange (Life Technologies). As a result, the secretion amount of N15 was significantly improved in all the deficient strains, as compared with the YDK010::phoS(W302C) strain (FIG. 1).

After the staining, the band intensity of N15 was digitized with image analysis software Multi Gauge (FUJIFILM), and the band intensity observed upon expressing N15 in each of the deficient strains was calculated as a relative value based on the band intensity observed upon expressing N15 in the YDK010::phoS(W302C) strain which was taken as 1.00. As a result, it was confirmed that the secretion amount of N15 was improved in a range of 2.49 to 4.70-fold in the deficient strains (Table 1).

From this, it was revealed that deletion of two or more genes of regX3, hrrA, and hrcA genes is an effective mutation that leads to an improvement of the secretion amount in secretory production of N15 in the YDK010::phoS(W302C) strain.

TABLE 1

| Strain | Relative intensity |
| --- | --- |
| YDK010::phoS (W 302C)/pPK4_C spAss_N 15 | 1.00 |
| YDK010::phoS (W 302C) ΔregX3 ΔhrcA/ pPK4_C spAss_N 15 | 3.04 |
| YDK010::phoS (W 302C) ΔregX3 ΔhrrA/ pPK4_C spAss_N 15 | 3.18 |
| YDK010::phoS (W 302C) ΔhrrA ΔhrcA/ pPK4_C spAss_N 15 | 2.49 |
| YDK010::phoS (W 302C) ΔregX3 ΔhrrA ΔhrcA/ pPK4_C spAss_N 15 | 4.70 |

Example 9: Secretory Production of Liver-Type Fatty Acid-Binding Protein (LFABP) Using *Corynebacterium glutamicum* Deficient in Two or More Genes of regX3, hrrA, and hrcA Genes The *C. glutamicum* YDK010::phoS(W302C) strain, the YDK010::phoS(W302C) ΔregX3ΔhrcA strain obtained in Example 4, the YDK010::phoS(W302C) ΔhrrAΔhrcA strain obtained in Example 5, the YDK010::phoS(W302C) ΔregX3ΔhrrA strain obtained in Example 6, and the YDK010::phoS(W302C) ΔregX3ΔhrrAΔhrcA strain obtained in Example 7 were each transformed with pPK4_CspB6Xa-LFABP disclosed in WO2016/171224 to obtain strains YDK010::phoS(W302C)/pPK4_CspB6Xa-LFABP, YDK010:phoS(W302C) ΔregX3ΔhrcA/ pPK4_CspB6Xa-LFABP, YDK010::phoS(W302C) ΔhrrAΔhrcA/pPK4_CspB6Xa-LFABP, YDK010::phoS (W302C) ΔregX3ΔhrrA/pPK4_CspB6Xa-LFABP, and YDK010::phoS(W302C) ΔregX3ΔhrrAΔhrcA/ pPK4_CspB6Xa-LFABP. pPK4_CspB6Xa-LFABP is a secretory expression plasmid of Liver-type fatty acid-binding protein of human (hereinafter, referred to as LFABP). pPK4_CspB6Xa-LFABP includes the promoter of cspB gene (PS2 gene) of the *C. glutamicum* ATCC 13869 strain and a gene encoding a fusion protein (hereinafter, referred to as CspB6Xa-LFABP) of the CspB signal peptide 30 amino acid residues of the *C. glutamicum* ATCC 13869 strain, the N-terminal 6 amino acid residues of CspB mature protein of the same strain, the Factor Xa protease recognition sequence IEGR, and LFABP, wherein the gene is linked downstream of the promoter.

The obtained transformants were each cultured on MMTG liquid medium (120 g of glucose, 3 g of MgSO$_4$·7H$_2$O, 30 g of (NH$_4$)$_2$SO$_4$, 1.5 g of KH$_2$PO$_4$, 0.03 g of FeSO$_4$·7H$_2$O, 0.03 g of MnSO$_4$·5H$_2$O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO₃, filled up with water to 1 L, and adjusted to pH7.0) containing 25 mg/L of kanamycin at 30° C. for 72 hr.

Figure 2:
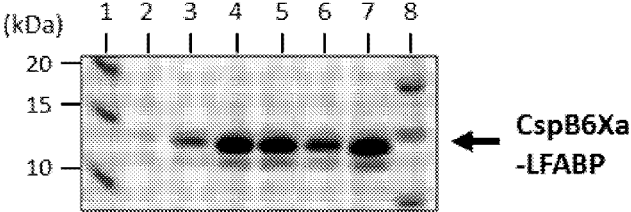
FIG. 2 is a photograph showing the results of SDS-PAGE observed upon expressing CspB6Xa-LFABP (LFABP fused with CspB signal peptide, mature CspB N-terminal sequence, and Factor Xa protease recognition sequence) in the *C. glutamicum* YDK010::phoS(W302C) strain and gene-deficient strains thereof.

After completion of the culture, 2.0 μL of the culture supernatant obtained by centrifuging each culture broth was subjected to reduced SDS-PAGE, and then staining was carried out with SYPRO Orange (Life Technologies). As a result, the secretion amount of CspB6Xa-LFABP was significantly improved in all the deficient strains, as compared with the YDK010::phoS(W302C) strain (FIG. 2).

After the staining, the band intensity of CspB6Xa-LFABP was digitized with image analysis software Multi Gauge (FUJIFILM), and the band intensity observed upon expressing CspB6Xa-LFABP in each of the deficient strains was calculated as a relative value based on the band intensity observed upon expressing CspB6Xa-LFABP in the YDK010::phoS(W302C) strain which was taken as 1.00. As a result, it was confirmed that the secretion amount of CspB6Xa-LFABP was improved in a range of 2.04 to 5.13-fold in the deficient strains (Table 2).

From this, it was revealed that deletion of two or more genes of regX3, hrrA, and hrcA genes is an effective mutation that leads to an improvement of the secretion amount also in secretory production of CspB6Xa-LFABP in the YDK010::phoS(W302C) strain.

TABLE 2

| Strain | Relative intensity |
| --- | --- |
| YDK010::phoS (W 302C)/pPK4_C spB6Xa-LFABP | 1.00 |
| YDK010::phoS (W 302C) ΔregX3 ΔhrcA/ pPK4_C spB6Xa-LFABP | 4.44 |
| YDK010::phoS (W 302C) ΔregX3 ΔhrrA/ pPK4_C spB6Xa-LFABP | 4.07 |
| YDK010::phoS (W 302C) ΔhrrA ΔhrcA/ pPK4_C spB6Xa-LFABP | 2.04 |
| YDK010::phoS (W 302C) ΔregX3 ΔhrrA ΔhrcA/ pPK4_C spB6Xa-LFABP | 5.13 |

Example 10: Secretory Production of Basic Fibroblast Growth Factor (bFGF) Using *Corynebacterium glutamicum* Deficient in Two or More Genes of regX3, hrrA, and hrcA Genes (1) Construction of co-expression plasmid of tatABC genes encoding Tat secretion system and gene encoding basic Fibroblast Growth Factor (bFGF) added with TorA signal sequence The amino acid sequence of basic Fibroblast Growth Factor (bFGF) of human has already been determined (DDBJ Accession number: E61144). This amino acid sequence is shown as SEQ ID NO: 63. Considering the codon frequency of *C. glutamicum*, a nucleotide sequence encoding bFGF was designed. The designed nucleotide sequence is shown as SEQ ID NO: 64.

Then, an expression cassette of a fusion protein of a signal peptide and bFGF (hereinafter, also simply referred to as bFGF), in which a DNA encoding 39 amino acid residues formed of a signal peptide of TorA protein derived from *E. coli* (UniProt Accession number: P33225) and the DNA of SEQ ID NO: 64 were linked downstream of the promoter of cspB gene of the *C. glutamicum* ATCC 13869 strain, and KpnI site was further added at both the 5'-side and 3'-side termini, was totally synthesized. The synthesized DNA fragment was treated with the restriction enzyme KpnI and inserted at KpnI site of pPK6 disclosed in WO 2016/171224, to construct pPK6_T_bFGF, which is a secretory expression plasmid of bFGF. As a result of nucleotide sequencing of the inserted fragment, it was confirmed that the gene encoding bFGF was constructed as intended. Nucleotide sequencing was carried out with BigDye® Terminator v3.1 Cycle Sequencing Kit (Applied Biosystems) and 3130 Genetic Analyzer (Applied Biosystems).

(2) Secretory production of basic Fibroblast Growth Factor (bFGF) using *Corynebacterium glutamicum* deficient in two or more genes of regX3, hrrA, and hrcA genes The *C. glutamicum* YDK010::phoS(W302C) strain, the YDK010::phoS(W302C) ΔregX3ΔhrcA strain obtained in Example 4, the YDK010::phoS(W302C) ΔhrrAΔhrcA strain obtained in Example 5, the YDK010::phoS(W302C) ΔregX3ΔhrrA strain obtained in Example 6, and the YDK010::phoS(W302C) ΔregX3ΔhrrAΔhrcA strain obtained in Example 7 were each transformed with pPK6_T_bFGF obtained in Example 10 (1), which is a secretory expression plasmid of bFGF, to obtain strains YDK010::phoS(W302C)/pPK6_T_bFGF, YDK010::phoS (W302C) ΔregX3ΔhrcA/pPK6_T_bFGF, YDK010::phoS (W302C) ΔhrrAΔhrcA/pPK6_T_bFGF, YDK010::phoS (W302C) ΔregX3ΔhrrA/pPK6_T_bFGF, and YDK010:: phoS(W302C) ΔregX3ΔhrrAΔhrcA/pPK6_T_bFGF.

The obtained transformants were each cultured on MMTG liquid medium (120 g of glucose, 3 g of MgSO₄·7H₂O, 30 g of (NH₄)₂SO₄, 1.5 g of KH₂PO₄, 0.03 g of FeSO₄·7H₂O, 0.03 g of MnSO₄·5H₂O, 0.45 mg of thiamine hydrochloride, 0.45 mg of biotin, 0.15 g of DL-methionine, 0.2 g (as total nitrogen) of soybean hydrolysate solution obtained with HCl, and 50 g of CaCO₃, filled up with water to 1 L, and adjusted to pH7.0) containing 25 mg/L of kanamycin at 30° C. for 72 hr.

Figure 3:
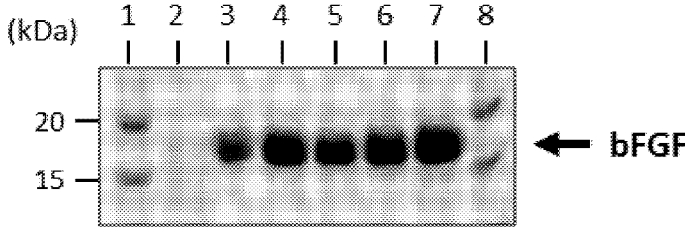
FIG. 3 is a photograph showing the results of SDS-PAGE observed upon expressing bFGF (bFGF fused with TorA signal peptide) in the *C. glutamicum* YDK010::phoS (W302C) strain and gene-deficient strains thereof.

After completion of the culture, 1.0 μL of the culture supernatant obtained by centrifuging each culture broth was subjected to reduced SDS-PAGE, and then staining was carried out with SYPRO Orange (Life Technologies). As a result, the secretion amount of bFGF was significantly improved in all the deficient strains, as compared with the YDK010::phoS(W302C) strain (FIG. 3).

After the staining, the band intensity of bFGF was digitized with image analysis software Multi Gauge (FUJIF-ILM), and the band intensity observed upon expressing bFGF in each of the deficient strains was calculated as a relative value based on the band intensity observed upon expressing bFGF in the YDK010::phoS(W302C) strain which was taken as 1.00. As a result, it was confirmed that the secretion amount of bFGF was improved in a range of 1.69 to 3.08-fold in the deficient strains (Table 3).

From this, it was revealed that deletion of two or more genes of regX3, hrrA, and hrcA genes is an effective mutation that leads to an improvement of the secretion amount also in secretory production of bFGF using the TorA signal sequence in the YDK010::phoS(W302C) strain. That is, it was revealed that deletion of two or more genes of regX3, hrrA, and hrcA genes is a mutation that leads to a significant improvement of the secretion amount a heterologous protein not only when using the Sec secretion system, but also when using the Tat secretion system.

TABLE 3

| Strain | Relative intensity |
| --- | --- |
| YDK010::phoS (W 302C)/pPK6_T_bFGF | 1.00 |
| YDK010::phoS (W 302C) ΔregX3 ΔhrcA/ pPK6_T_bFGF | 2.31 |
| YDK010::phoS (W 302C) ΔregX3 ΔhrrA/ pPK6_T_bFGF | 1.69 |
| YDK010::phoS (W 302C) ΔhrrA ΔhrcA/ pPK6_T_bFGF | 2.17 |
| YDK010::phoS (W 302C) ΔregX3 ΔhrrA ΔhrcA/ pPK6_T_bFGF | 3.08 |

INDUSTRIAL APPLICABILITY

According to the present disclosure, heterologous proteins can be efficiently produced by secretory production.

Explanation of Sequence Listing

SEQ ID NOS:
- 1: Nucleotide sequence of mutant phoS gene of *C. glutamicum* YDK010
- 2: Amino acid sequence of mutant PhoS protein of *C. glutamicum* YDK010
- 3: Amino acid sequence of PhoS protein of *C. glutamicum* ATCC 13032
- 4: Amino acid sequence of PhoS protein of *C. glutamicum* ATCC 14067
- 5: Amino acid sequence of PhoS protein of *C. callunae*
- 6: Amino acid sequence of PhoS protein of *C. crenatum*
- 7: Amino acid sequence of PhoS protein of *C. efficiens*
- 8: Nucleotide sequence of phoR gene of *C. glutamicum* ATCC 13032
- 9: Amino acid sequence of PhoR protein of *C. glutamicum* ATCC 13032
- 10: Nucleotide sequence of cspB gene of *C. glutamicum* ATCC 13869
- 11: Amino acid sequence of CspB protein of *C. glutamicum* ATCC 13869
- 12: Nucleotide sequence of tatA gene of *C. glutamicum* ATCC 13032
- 13: Amino acid sequence of TatA protein of *C. glutamicum* ATCC 13032
- 14: Nucleotide sequence of tatB gene of *C. glutamicum* ATCC 13032

- 15: Amino acid sequence of TatB protein of *C. glutamicum* ATCC 13032
- 16: Nucleotide sequence of tatC gene of *C. glutamicum* ATCC 13032
- 17: Amino acid sequence of TatC protein of *C. glutamicum* ATCC 13032
- 18: Amino acid sequence of TorA signal peptide
- 19: Amino acid sequence of SufI signal peptide
- 20: Amino acid sequence of PhoD signal peptide
- 21: Amino acid sequence of LipA signal peptide
- 22: Amino acid sequence of IMD signal peptide
- 23 and 24: Amino acid sequence of twin-arginine motif
- 25: Amino acid sequence of PS1 signal peptide
- 26: Amino acid sequence of PS2 signal peptide
- 27: Amino acid sequence of SlpA signal peptide
- 28: Amino acid sequence of CspB mature protein of *C. glutamicum* ATCC 13869
- 29 to 36: Amino acid sequences of insertion sequence used in the present disclosure in one embodiment
- 37: Recognition sequence of factor Xa protease
- 38: Recognition sequence of ProTEV protease
- 39: Nucleotide sequence of senX3 gene of *C. glutamicum* ATCC 13869
- 40: Amino acid sequence of SenX3 protein of *C. glutamicum* ATCC 13869
- 41: Nucleotide sequence of regX3 gene of *C. glutamicum* ATCC 13869
- 42: Amino acid sequence of RegX3 protein of *C. glutamicum* ATCC 13869
- 43: Nucleotide sequence of hrrS gene of *C. glutamicum* ATCC 13869
- 44: Amino acid sequence of HrrS protein of *C. glutamicum* ATCC 13869
- 45: Nucleotide sequence of hrrA gene of *C. glutamicum* ATCC 13869
- 46: Amino acid sequence of HrrA protein of *C. glutamicum* ATCC 13869
- 47: Nucleotide sequence of hrcA gene of *C. glutamicum* ATCC 13869
- 48: Amino acid sequence of HrcA protein of *C. glutamicum* ATCC 13869
- 49 to 60: Primers
- 61: Nucleotide sequence encoding VHH antibody N15
- 62: Amino acid sequence of VHH antibody N15
- 63: Nucleotide sequence encoding bFGF
- 64: Amino acid sequence of bFGF

The invention claimed is:

1. A method for producing a heterologous protein, the method comprising:

culturing a coryneform bacterium having a genetic construct for secretory expression of the heterologous protein, and wherein as a result of said culturing, said coryneform bacterium secretes said heterologous protein; and collecting the heterologous protein, wherein the coryneform bacterium has at least two modifications so that secretory production of the heterologous protein by the coryneform bacterium is increased, wherein said modifications are:

(A) the activity of a RegX3 protein has completely disappeared as compared with a non-modified strain of the coryneform bacterium, (B) the activity of an HrrSA system is reduced as compared with a non-modified strain of the coryneform bacterium, and (C) the activity of an HrcA protein has completely disappeared as compared with a non-modified strain of the coryneform bacterium;

wherein modification (A) is obtained by deleting a regX3 gene;

wherein modification (C) is obtained by deleting an hrcA gene;

wherein the genetic construct comprises, in the direction from 5' to 3', a promoter sequence that functions in the coryneform bacterium, a nucleic acid sequence encoding a signal peptide that functions in the coryneform bacterium, and a nucleic acid sequence encoding the heterologous protein;

wherein the coryneform bacterium has been further modified so as to harbor a phoS gene encoding a mutant PhoS protein, wherein the mutant PhoS protein comprises a mutation of replacing an amino acid residue corresponding to a tryptophan residue at position 302 in SEQ ID NO: 2 with a cysteine residue in a wild-type PhoS protein, wherein the wild-type PhoS protein is selected from the group consisting of:

(a) a protein comprising any of the amino acid sequences of SEQ ID NOS: 2 to 7;

(b) a protein comprising any of the amino acid sequences of SEQ ID NOS: 2 to 7, but which includes substitution, deletion, insertion, and/or addition of 1 to 10 amino acid residues, wherein said protein has a function as a sensor kinase of a PhoRS system; and (c) a protein comprising an amino acid sequence showing an identity of 90% or higher to any of the amino acid sequences of SEQ ID NOS: 2 to 7, wherein said protein has a function as a sensor kinase of a PhoRS system, wherein the signal peptide is a TorA signal peptide or a Sec-dependent signal peptide;

wherein the heterologous protein is expressed as a fusion protein with the signal peptide; and wherein the coryneform bacterium is *Corynebacterium glutamicum*.

2. The method according to claim 1, wherein a number of molecules of the RegX3 protein per cell is reduced as compared with a non-modified strain of the coryneform bacterium; the number of molecules of either or both of an HrrS protein and an HrrA protein per cell is reduced as compared with a non-modified strain of the coryneform bacterium; and/or the number of molecules of the HrcA protein per cell is reduced as compared with a non-modified strain of the coryneform bacterium.

3. The method according to claim 1, wherein the coryneform bacterium has a combination of modifications (A), (B), and (C).

4. The method according to claim 1, wherein the modification (B) is obtained by reducing the activity of one or both of an HrrS protein and an HrrA protein.

5. The method according to claim 4, wherein the modification (B) is obtained by reducing at least the activity of the HrrA protein.

6. The method according to claim 1, wherein the modification (B) is obtained by reducing the number of molecules of one or both of an HrrS protein and an HrrA protein per cell.

7. The method according to claim 6, wherein the modification (B) is obtained by reducing at least the number of molecules of the HrrA protein per cell.

8. The method according to claim 1, wherein the RegX3 protein is selected from the group consisting of:

(a) a protein comprising the amino acid sequence of SEQ ID NO: 42;

(b) a protein comprising the amino acid sequence of SEQ ID NO: 42, but which includes substitution, deletion, insertion, and/or addition of 1 to 10 amino acid residues, wherein said protein has a function as a response regulator of a SenX3-RegX3 system; and (c) a protein comprising an amino acid sequence showing an identity of 90% or higher to the amino acid sequence of SEQ ID NO: 42, wherein said protein has a function as a response regulator of a SenX3-RegX3 system.

9. The method according to claim 2, wherein the HrrS protein is selected from the group consisting of:

(a) a protein comprising the amino acid sequence of SEQ ID NO: 44;

(b) a protein comprising the amino acid sequence of SEQ ID NO: 44, but which includes substitution, deletion, insertion, and/or addition of 1 to 10 amino acid residues, wherein said protein has a function as a sensor kinase of an HrrSA system; and (c) a protein comprising an amino acid sequence showing an identity of 90% or higher to the amino acid sequence of SEQ ID NO: 44, wherein said protein has a function as a sensor kinase of an HrrSA system.

10. The method according to claim 2, wherein the HrrA protein is selected from the group consisting of:

(a) a protein comprising the amino acid sequence of SEQ ID NO: 46;

(b) a protein comprising the amino acid sequence of SEQ ID NO: 46, but which includes substitution, deletion, insertion, and/or addition of 1 to 10 amino acid residues, wherein said protein has a function as a response regulator of an HrrSA system; and (c) a protein comprising an amino acid sequence showing an identity of 90% or higher to the amino acid sequence of SEQ ID NO: 46, wherein said protein has a function as a response regulator of an HrrSA system.

11. The method according to claim 1, wherein the HrcA protein is selected from the group consisting of:

(a) a protein comprising the amino acid sequence of SEQ ID NO: 48;

(b) a protein comprising the amino acid sequence of SEQ ID NO: 48, but which includes substitution, deletion, insertion, and/or addition of 1 to 10 amino acid residues, wherein said protein has a function as a transcription repressor of heat-shock proteins; and (c) a protein comprising an amino acid sequence showing an identity of 90% or higher to the amino acid sequence of SEQ ID NO: 48, wherein said protein has a function as a transcription repressor of heat-shock proteins.

12. The method according to claim 1, wherein the coryneform bacterium has been further modified so that expression of one or more genes encoding a Tat secretion system is increased as compared with a non-modified strain of the coryneform bacterium.

13. The method according to claim 12, wherein the one or more genes encoding a Tat secretion system are a tatA gene, tatB gene, tatC gene, and tatE gene.

14. The method according to claim 1, wherein the Sec-dependent signal peptide is a signal peptide selected from the group consisting of a PS1 signal peptide, PS2 signal peptide, and SlpA signal peptide.

15. The method according to claim 1, wherein the genetic construct further comprises a nucleic acid sequence encoding an amino acid sequence comprising Gln-Glu-Thr between the nucleic acid sequence encoding the signal peptide that functions in the coryneform bacterium and the nucleic acid sequence encoding the heterologous protein.

16. The method according to claim 15, wherein the genetic construct further comprises a nucleic acid sequence encoding an amino acid sequence used for enzymatic digestion between the nucleic acid sequence encoding the amino acid sequence comprising Gln-Glu-Thr and the nucleic acid sequence encoding the heterologous protein.

17. The method according to claim 1, wherein the coryneform bacterium is *Corynebacterium glutamicum* AJ12036 or *Corynebacterium glutamicum* ATCC 13869.

18. The method according to claim 1, wherein a number of molecules of a cell surface layer protein per cell of the coryneform bacterium is reduced as compared with a non-modified strain of the coryneform bacterium.

19. The method according to claim 1, wherein the promoter is cspB promoter.

\* \* \* \* \*